US009453239B2

(12) United States Patent
Moss et al.

(10) Patent No.: US 9,453,239 B2
(45) Date of Patent: Sep. 27, 2016

(54) RECOMBINANT MVA VIRUSES EXPRESSING CLADE A/G, CLADE B, AND CLADE C MODIFIED HIV ENV, GAG AND POL GENES

(75) Inventors: Bernard Moss, Bethesda, MD (US); Linda Wyatt, Rockville, MD (US); Harriet L. Robinson, Atlanta, GA (US)

(73) Assignees: Emory University, Atlanta, GU (US); The Government of the United States of America, as represented by the Secretary Department of Health and Human Services, National Institutes of Health, Washington, DC (US)

( * ) Notice: Subject to any disclaimer, the term of this patent is extended or adjusted under 35 U.S.C. 154(b) by 1088 days.

(21) Appl. No.: 11/574,285

(22) PCT Filed: Aug. 29, 2005

(86) PCT No.: PCT/US2005/030977

§ 371 (c)(1), (2), (4) Date: Feb. 26, 2007

(87) PCT Pub. No.: WO2006/026667

PCT Pub. Date: Mar. 9, 2006

(65) Prior Publication Data

US 2008/0193483 A1 Aug. 14, 2008

Related U.S. Application Data

(60) Provisional application No. 60/604,918, filed on Aug. 27, 2004.

(51) Int. Cl.

| | |
|---|---|
| ***A61K 39/275*** | (2006.01) |
| ***A61K 39/12*** | (2006.01) |
| ***C12N 15/86*** | (2006.01) |
| ***C12N 7/00*** | (2006.01) |
| ***A61K 39/285*** | (2006.01) |
| ***C07K 14/005*** | (2006.01) |
| *A61K 39/00* | (2006.01) |

(52) U.S. Cl.

CPC ............. *C12N 15/86* (2013.01); *C07K 14/005* (2013.01); *A61K 2039/5256* (2013.01); *A61K 2039/53* (2013.01); *A61K 2039/57* (2013.01); *C12N 2710/24143* (2013.01); *C12N 2740/16023* (2013.01); *C12N 2740/16122* (2013.01); *C12N 2740/16134* (2013.01); *C12N 2740/16222* (2013.01); *C12N 2740/16234* (2013.01); *C12N 2830/00* (2013.01); *C12N 2830/15* (2013.01); *C12N 2830/60* (2013.01)

(58) Field of Classification Search

CPC ................. A61K 2039/5256; A61K 2039/53; C07K 14/005; C12N 15/86; C12N 2710/24143

USPC ............................................................ 435/6

See application file for complete search history.

(56) References Cited

FOREIGN PATENT DOCUMENTS

| | | | |
|---|---|---|---|
| WO | WO02072754 | 9/2002 | |
| WO | WO03076591 | * 9/2003 | |
| WO | WO2004/035006 | 4/2004 | |
| WO | WO2004008701 | 10/2004 | ............ A61K 39/12 |
| WO | WO2004087201 | * 10/2004 | |

OTHER PUBLICATIONS

Jacobsen et al., *Virology*., vol. 206:pp. 527-534, 1995.
Ellenberger et al., *Virology*., vol. 319:pp. 118-130, 2004.
Vogels et al., *Journal of Virology*., vol. 77, No. 15:pp. 8263-8271, Aug. 2003.
Hanke et al., *Vaccine*., vol. 16, No. 5:pp. 439-445, 1998.
Schneider et al., *Nature Medicine*., vol. 4, No. 4:pp. 397-402, Apr. 1998.
Schneider et al., *Vaccine*., vol. 19:pp. 4595-4602, 2001.
Allen et al., *Journal of Immunology*., vol. 164:pp. 4968-4978, 2000.
Horton et al., *Journal of Virology*., vol. 76, No. 14:pp. 7187-7202, Jul. 2002.
O'Neill et al., *AIDS Research and Human Retroviruses*., vol. 19, No. 10:pp. 883-890, Oct. 2003.
Loeb et al, *Journal of Virology*., vol. 63, No. 1:pp. 111-121, Jan. 1989.
O'Neill et al., *Journal of Medical Primatology*., vol. 31:pp. 217-227, 2002.
Amara et al., *Journal of Virology*., vol. 76, No. 12:pp. 6138-6146. Jun. 2002.
Barouch et al., *Nature*., vol. 415:pp. 335-339, Jan. 17, 2002.
Kang et al., *Bio. Chem*., vol. 380:pp. 353-364, Mar. 1999.
Montara et al., *Journal of Virology*., vol. 72, No. 2:pp. 1403-1410.
Goettlinger et al., *Proc. Natl. Acad. Sci.*, vol. 86, No. 15:pp. 5781-5785, Aug. 1, 1989.
Karacostas et al., *Virology*., vol. 193:pp. 661-671, 1993.
Peng et al., *Journal of Virology*., vol. 63, No. 6:pp. 2550-2556, Jun. 1989.
Huang et al., *Journal of Virology*., vol. 75, No. 10:pp. 4947-4951, May 2001.
Schneider et al., *Journal of Virology*., vol. 71, No. 7:pp. 4892-4903, Jul. 1997.
Kohl et al., *Proc. Natl. Acad. Sci.*, vol. 85, No. 13:pp. 4686-4690, Jul. 1, 1988.
Wyatt et al., *AIDS Research and Human Retroviruses*., vol. 20, No. 6:pp. 645-653, 2004.
Smith et al., *AIDS Research and Human Retroviruses*., vol. 20, No. 6:pp. 654-665, 2004.
Tang et al., *Nature*., vol. 356:pp. 152-154, Mar. 12, 1992.
Ulmer et al., *Science*., vol. 259:pp. 1745-1749, Mar. 19, 1993.
Wolff et al., *Science*., vol. 247, No. 4949:pp. 1465-1468, Mar. 23, 1990.
Boyer et al., *Nature Medicine*., vol. 3, No. 5:pp. 526-532, May 1997.
Letvin et al., *Proc. Natl. Acad. Sci.*, vol. 94:pp. 9378-9383, Aug. 1997.
Egan et al., *Journal of Virology*., vol. 74, No. 16:pp. 7485-7495, Aug. 2000.

(Continued)

*Primary Examiner* — Janet L Andres
*Assistant Examiner* — Barry A Chestnut
(74) *Attorney, Agent, or Firm* — King & Spalding LLP

(57) ABSTRACT

The invention provides modified vaccinia Ankara (MVA), a replication-deficient strain of vaccinia virus, expressing human immunodeficiency virus (HIV) env, gag, and pol genes.

16 Claims, 50 Drawing Sheets

(56) References Cited

OTHER PUBLICATIONS

Arthos et al., *Journal of Virology*., vol. 70, No. 6:pp. 3978-3991, Jun. 1996.
Amara et al., *Science*., vol. 292, No. 5514:pp. 69-74, Apr. 6, 2001.
Barouch et al., *Science*., vol. 290, No. 5491:pp. 486-492, Oct. 20, 2000.
Barouch et al., *Journal of Virology*., vol. 75, No. 11:pp. 5151-5158, Jun. 2001.
Rose et al., *Cell*., vol. 106:pp. 539-549, Sep. 7, 2001.
Shiver et al., *Nature*., vol. 415:pp. 331-335, Jan. 17, 2002.
Robinson et al., *AIDS Reviews*., vol. 2, No. 2:pp. 105-110, Apr.-Jun. 2000.
U.S. Appl. No. 09/798,675, Jul. 1, 2002, Restriction Requirement.
U.S. Appl. No. 09/798,675, Feb. 27, 2003, Non-Final Office Action.
U.S. Appl. No. 09/798,675, Dec. 5, 2003, Final Office Action.
U.S. Appl. No. 09/798,675, Jun. 9, 2004, Non-Final Office Action.
U.S. Appl. No. 10/093,953, Jul. 15, 2005, Non-Final Office Action.
U.S. Appl. No. 11/009,063, Apr. 13, 2007, Non-Final Office Action.
U.S. Appl. No. 11/333,770, Mar. 21, 2007, Restriction Requirement.
U.S. Appl. No. 10/336,566, Nov. 10, 2005, Restriction Requirement.
U.S. Appl. No. 10/336,566, Apr. 6, 2006, Non-Final Office Action.
U.S. Appl. No. 10/336,566, Jan. 8, 2007, Final Office Action.
U.S. Appl. No. 10/336,566, Sep. 21, 2007, Final Office Action.
U.S. Appl. No. 10/336,566, Jan. 28, 2008, Final Office Action.
U.S. Appl. No. 10/646,628, Dec. 20, 2004, Restriction Requirement.
U.S. Appl. No. 10/646,628, Sep. 20, 2005, Non-Final Office Action.
U.S. Appl. No. 10/646,628, Sep. 13, 2006, Final Office Action.
U.S. Appl. No. 10/646,628, Jul. 19, 2007, Non-Final Office Action.
U.S. Appl. No. 12/033,300, filed Feb. 19, 2008.
U.S. Appl. No. 11/574,285, filed Feb. 26, 2007.
Zhongde Wang et al., "Modified H5 promoter improves stability of insert genes while maintaining immunogenicity during extended passage of genetically engineered MVA vaccines," Vaccine 28:1547-1557 (2010).
Robinson H L et al., "Studies on GM-CSF DNA as an adjuvant for neutralizing Ab elicited by a DNA/MVA immunodeficiency virus vaccine," Virology 352:285-294 (2006).
Lai et al., "GM-CSF DNA: An adjuvant for higher avidity IgG, rectal IgA, and increased protection against the acute phase of a SHIV-89.6P challenge by a DNA/MVA immunodeficiency virus vaccine," Virology 369:153-167 (2007).
Earl P L et al., "Design and evaluation of multi-gene, multi-clade HIV-1 MVA vaccines," Vaccine 27:5885-5895 (2009).
Earl P L et al., "Comparison of Vaccine Strategies Using Recombinant env-gag-pol MVA with or without an Oligomeric Env Protein Boost in the SHIV Rhesus Macaque Model," Virology 294:270-281 (2002).

* cited by examiner

| Chemokine coreceptor used | PBMC replication | Macrophage replication | T-cell-line replication | REplicative phenotype | Syncytium-inducing phenotype |
|---|---|---|---|---|---|
| X4 | + | − | + | Rapid/high | ++ |
| R5 | + | + | − | Slow/low | − |
| R5/X4 | + | + | + | Rapid/high | + |

FIG. 3

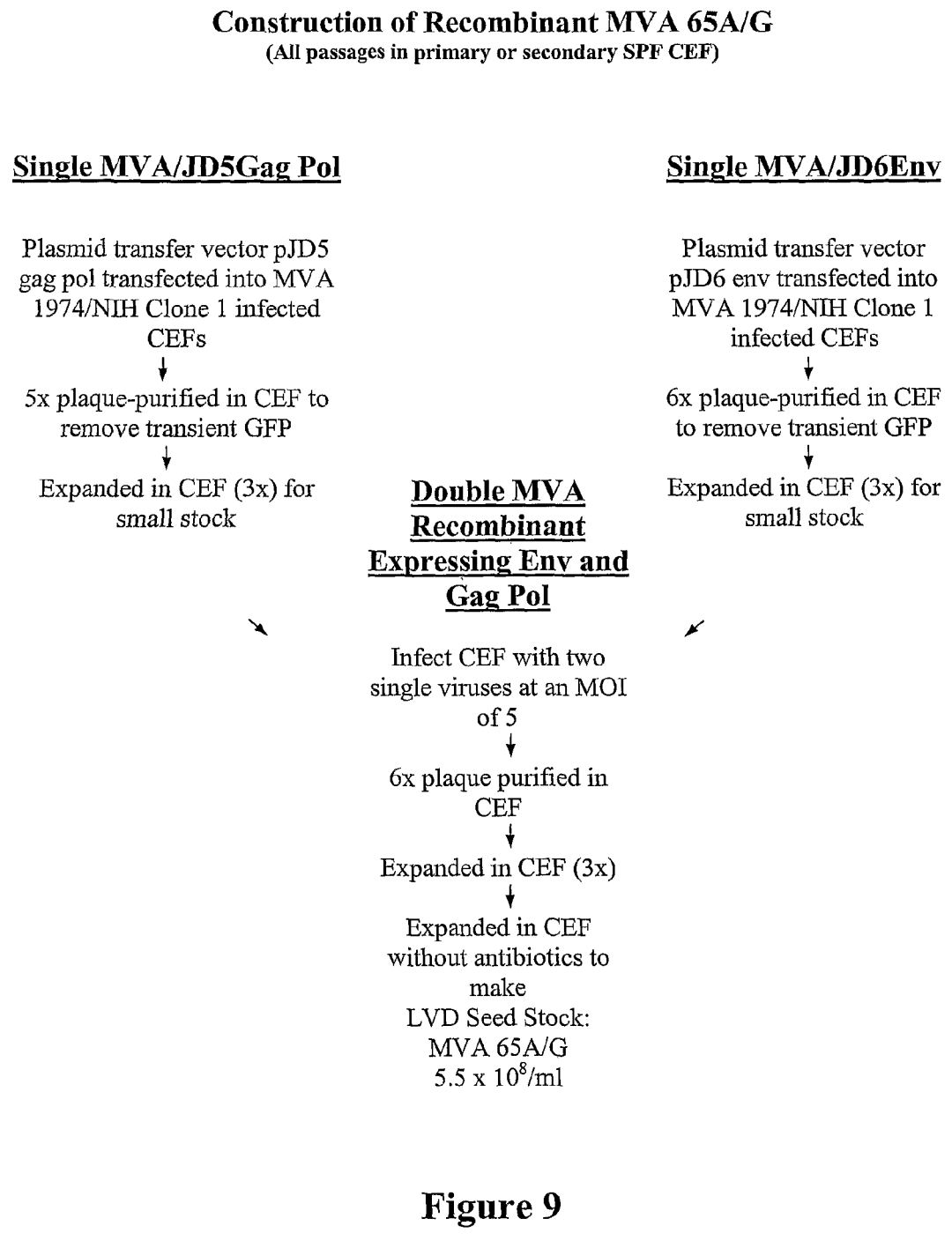

Construction of Recombinant MVA 65A/G

(All passages in primary or secondary SPF CEF)

Single MVA/JD5Gag Pol

Plasmid transfer vector pJD5 gag pol transfected into MVA 1974/NIH Clone 1 infected CEFs 5x plaque-purified in CEF to remove transient GFP Expanded in CEF (3x) for small stock

Single MVA/JD6Env

Plasmid transfer vector pJD6 env transfected into MVA 1974/NIH Clone 1 infected CEFs 6x plaque-purified in CEF to remove transient GFP Expanded in CEF (3x) for small stock

Double MVA Recombinant Expressing Env and Gag Pol

Infect CEF with two single viruses at an MOI of 5

6x plaque purified in CEF

Expanded in CEF (3x)

Expanded in CEF without antibiotics to make
LVD Seed Stock:
MVA 65A/G
5.5 x $10^8$/ml

Figure 9

MVA 65A/G Env Sequence

ATGAGAGTGATGGGGATACAGAAGAATTATCCACTCTTATGGAGAGGGGGTATGACAA
TATTTTGGTTAATGATGATTTGTAATGCTGAAAAGTTGTGGGTCACAGTCTACTATGGG
GTACCTGTGTGGAGAGACGCAGAGACCACCCTATTCTGTGCATCAGATGCTAAAGCAT
ATGACAAAGAAGCACACAATGTCTGGGCTACGCATGCCTGCGTACCCACAGACCCTGA
CCCACAAGAATTACCTTTGGTAAATGTAACAGAAGAGTTTAACATGTGGAAAAATAAT
ATGGTAGAACAGATGCATGAAGATATAATTAGTCTATGGGACCAAAGCTTAAAGCCAT
GTGTACAGCTAACCCCTCTCTGCGTTACTTTAGGGTGTGCTGACGCTCAAAACGTCACC
GACACCAACACCACCATATCTAATGAAATGCAAGGGGAAATAAAAAACTGCTCTTTCA
ATATGACCACAGAATTAAGAGATAAGAAGCAGAAAGTGTATGCACTTTTCTATAGACC
TGATGTAATAGAAATTAATAAAACTAAGATTAACAATAGTAATAGTAGTCAGTATATG
TTAATAAATTGTAATACCTCAACCATTACACAGACTTGTCCAAAGGTATCCTTTGAGCC
AATTCCCATACATTATTGTGCCCCAGCTGGTTTTGCAATTCTAAAGTGTAATGATACGG
AGTTCAGTGGAAAAGGGACATGCAAGAGTGTCAGCACAGTACAATGCACACATGGAA
TCAAGCCAGTAGTATCAACTCAACTGCTGTTAAATGGCAGTCTAGCAGAAGGAAAGAT
AGCGATTAGATCTGAGAATATCTCAAACAATGCCAAAACTATAATAGTACAATTGACT
GAGCCTGTAGAAATTAATTGTATCAGACCTGGCAACAATACAAGAAAAAGTGTACGCA
TAGGACCAGGACAAACATTCTATGCAACAGGTGACATAATAGGAGATATAAGACAAG
CACACTGTAATGTTAGTAAAATAGCATGGGAAGAAACTTTACAAAAGGTAGCTGCACA
ATTAAGGAAGCACTTTCAGAATGCCACAATAAAATTTACTAAACACTCAGGAGGGGAT
TTAGAAATTACAACACATAGTTTTAATTGTGGAGGAGAATTCTTCTATTGCAATACAAC
AAAGCTGTTTAATAGCACTTGGAATAATGATAACTCAAACCTCACAGAGGAAAAGAGA
AAGGAAAACATAACTCTCCACTGCAGAATAAAGCAAATTGTAAATATGTGGCAGAGA
GTAGGACAAGCAATATATGCCCCTCCCATCCCAGGAAACATAACTTGTGGATCAAACA
TTACTGGGCTACTATTAACAAGAGATGGAGGGAATAATGGTACAAATGATACTGAGAC
CTTCAGGCCTGGAGGAGGAGATATGAGGGACAATTGGAGAAGTGAATTATATAAATAT
AAAGTAGTAAAAATTGAACCACTAGGTGTAGCACCAACCCCTGCAAAAAGAAGAGTG
GTGGAAAGAGAAAAAAGAGCAGTTGGAATGGGAGCTTTGATCTTTGAGTTCTTAGGAG
CAGCAGGAAGCACTATGGGCGCGGCGTCAATGGCGCTGACGGTACAGGCCAGACAAT
TATTGTCTGGTATAGTGCAACAGCAGAGCAATCTGCTGAAGGCTATAGAGGCTCAACA
ACATCTGTTGAGACTCACGGTCTGGGGCATTAAACAGCTCCAGGCAAGAGTCCTGGCT
CTGGAAAGATACCTAAAGGATCAACAGCTCCTAGGAATTTGGGGCTGCTCTGGAAAAC
TCATTTGCACCACTGCTGTACCTTGGAACTCTAGCTGGAGTAATAAAAGTTATAATGAC
ATATGGGATAACATGACCTGGCTGCAATGGGATAAAGAAATTAACAATTACACATACA
TAATATATAATCTACTTGAAAAATCGCAGAACCAGCAGGAAATTAATGAACAAGACTT
ATTGGCATTAGACAAGTGGGCAAGTCTGTGGAATTGGTTTGACATAACAAGCTGGCTA
TGGTATATAAGATTAGGTATAATGATAGTAGGAGGCGTAATAGGCTTAAGAATAATTT
TTGCTGTGCTTACTATAGTGAATAGAGTTAGGCAGGGATACTCACCTTTGTCATTCCAG
ACCCTTGCCCACCACCAGAGGGAACCCGACAGGCCCGAAAGAATCGAAGAAGGAGGT
GGCGAGCAAGACTAA

Figure 12

MVA 65 A/G Gag Pol Sequence

ATGGGTGCGAGAGCGTCAGTGTTAACGGGGGAAAATTAGATTCATGGGAGAAAATT
AGGTTAAGGCCAGGGGGAAAGAAAAGATATAGACTAAAACACCTAGTATGGGCAAGC
AGGGAGCTGGAGAGATTCGCACTTAACCCTGGCCTATTAGAAACAGCAGAAGGATGTC
AACAACTAATGGGACAGTTACAACCAGCTCTCAGGACAGGATCAGAAGAGTTTAAATC
ATTATATAATATAGTAGCAACCCTTTGGTGCGTACATCAAAGAATAGACATAAAAGAC
ACCCAGGAGGCCTTAGATAAAGTAGAGGAAAAACAAAATAAGAGCAAGCAAAAGGCA
CAGCAGGCAGCAGCTGCAACAGCCGCCACAGGAAGCAGCAGCCAAAATTACCCTATA
GTGCAAAATGCACAAGGGCAAATGGTACATCAGTCCATGTCACCTAGGACTTTAAATG
CATGGGTGAAGGTAATAGAAGAAAAGGCTTTTAGCCCAGAGGTAATACCCATGTTTTC
AGCATTATCAGAGGGAGCCACCCCACAAGATTTAAATATGATGCTAAACATAGTGGGG
GGACACCAGGCAGCAATGCAGATGTTAAAAGATACCATCAATGATGAAGCTGCAGAA
TGGGACAGAGTACATCCAGTACATGCAGGGCCTATTCCACCAGGCCAAATGAGGGAAC
CAAGGGGAAGTGACATAGCAGGAACTACTAGTACCCTTCAAGAACAAATAGGATGGA
TGACAAGTAATCCACCTATCCCAGTGGGAGAAATCTATAAAAGATGGATAGTCCTGGG
ATTAAATAAAATAGTAAGAATGTATAGCCCTACCAGCATTTTGGACATAAGACAAGGG
CCAAAAGAACCCTTTAGAGATTATGTAGACAGGTTCTTTAAAACTTTGAGAGCTGAAC
AAGCTACGCAGGAGGTAAAAAACTGGATGACAGAAACCTTGTTGGTCCAAAATGCGA
ATCCAGACTGCAAGTCCATTTTAAGAGCATTAGGACCAGGGGCTACATTAGAAGAAAT
GATGACATCATGTCAGGGAGTGGGAGGACCTGGCCATAAAGCAAGGGTTTTGGCTGAG
GCAATGAGTCAAGTACAACAGACCAATGTAATGATGCAGAGAGGCAATTTTAGAGGCC
AGAGAATAATAAAGTGTTTCAACTGTGGCAAAGAAGGACACCTAGCCAGAAATTGCA
AGGCTCCTAGAAAGAGAGGCTGTTGGAAATGTGGAAAGGAAGGACACCAAATGAAAG
ACTGTACTGAAAGACAGGCTAATTTTTTAGGGAAAATTTGGCCTTCCCACAAGGGGAG
GCCAGGAAATTTTCCTCAGAGCAGACCAGAACCAACAGCCCCGCCAGCAGAGAGCTTT
GGAGTGGGGGAAGAGATACCCTCCTCTCCGAAGCAGGAGCCGAGGGACAAGGGACTA
TATCCTCCCTTAACTTCCCTCAAATCACTCTTTGGCAACGACCAGTAGTCACAGTAAGA
ATAGGGGGACAGCCAATAGAAGCCCTATTAGACACAGGAGCAGATGATACAGTATTA
GAAGAAATAAGTTTACCAGGAAAATGGAAACCAAAAATGATAGGGGGAATTGGAGGT
TTTATCAAAGTAAGACAGTATGATCAGATATCTATAGAAATTTGTGGAAAAAGGGCCA
TAGGTACAGTATTAGTAGGACCTACACCTGTCAACATAATTGGACGAAATATGTTGAC
TCAGATTGGTTGTACTTTAAATTTTCCAATTAGTCCTATTGAAACTGTGCCAGTAAAAT
TAAAGTCAGGAATGGATGGCCCAAAGGTTAAACAATGGCCATTGACAGAAGAAAAAA
TAAAAGCATTAAAAGAAATTTGTGCAGAGATGGAAAAGGAAGGAAAAATTTCAAAAA
TTGGGCCTGAAAACCCATACAATACTCCAATATTTGCCATAAAGAAAAAAGATAGTAC
TAAATGGAGAAAATTAGTAGATTTCAGAGAACTCAATAAGAGAACTCAAGACTTCTGG
GAGGTCCAATTAGGAATACCTCATCCTGCGGGATTAAAAAAGAAAAAATCAGTAACAG
TACTAGATGTGGGGGATGCATATTTTTCAGTTCCCTTAGATGAAGACTTTAGAAAATAT
ACTGCATTCACCATACCTAGTTTAAATAATGAGACACCAGGGATTAGATATCAGTACA
ATGTACTCCCACAGGGATGGAAAGGATCACCAGCAATATTTCAGGCAAGCATGACAAA
AATCTTAGAGCCCTTTAGAGCAAAAAATCCAGAGATAGTGATCTACCAATATATGAAC
GATTTATATGTAGGATCTGACTTAGAAATAGGGCAGCATAGAGCAAAAATAGAGGAGT
TGAGAGAACATCTATTGAAATGGGGATTTACCACACCAGACAAAAAACATCAGAAAG
AACCTCCATTTCTTTGGATGGGATATGAACTCCATCCTGACAAATGGACAGTCCAGCCT
ATACAGCTGCCAGAAAAAGACAGCTGGACTGTCAATGATATACAAAAATTAGTGGGA
AAACTAAATACCGCAAGTCAGATTTATGCAGGAATTAAAGTAAAGCAATTGTGTAGAC
TCCTCAGGGGAGCCAAAGCGCTAACAGATGTAGTAACACTGACTGAGGAAGCAGAATT
AGAATTGGCAGAGAACAGGGAAATTCTAAAAGAACCTGTACATGGAGTATATTATGAC

Figure 13

CCAACAAAAGACTTAGTGGCAGAAATACAGAAACAAGGGCAAGATCAATGGACATAT
CAAATTTATCAAGAGCCATTTAAAAATCTAAAGACAGGAAAATATGCAAAAAAGAGG
TCGGCCCACACTAATGATGTAAAACAATTAACAGAGGTAGTGCAGAAAATAGCCATAG
AAAGCATAGTAATATGGGGAAAGACCCCTAAATTTAGACTACCCATACAAAGAGAAA
CATGGGAAGCATGGTGGATGGAGTATTGGCAGGCTACCTGGATTCCTGAATGGGAGTT
TGTCAATACCCCTCCTCTAGTAAAATTATGGTACCAGTTAGAGAAGGACCCCATAATG
GGAGCAGAAACTTTCTATGTAGATGGGGCAGCTAATAGGGAGACTAAGCTAGGAAAA
GCAGGGTATGTCACTGACAGAGGAAGACAAAAGGTTGTTTCCCTAATTGAGACAACAA
ATCAAAAGACTCAGTTACATGCAATTCATCTAGCCTTGCAGGATTCAGGATCAGAAGT
AAATATAGTAACAGACTCACAGTATGCATTAGGAATCATTCAGGCACAACCAGACAGG
AGTGAATCAGAGTTAGTCAATCAAATAATAGAGAAACTAATAGAAAAGGACAAAGTC
TACCTGTCATGGGTACCAGCACACAAAGGGATTGGAGGAAATGAACAAGTAGATAAA
TTAGTCAGTAGTGGAATCAGAAAGGTACTATTTTTAGATGGAATAGATAAAGCCCAAG
ATGAACATTAG

FIGURE 13, contd.

Figure 19
P11
GFP
Direct Repeat 2
mH5 Promoter
Direct Repeat 1
MVA Del III Left Flank
pLAS-1 HXB2/BH10 Gag Pol
(8821 bp)
HXB2/BH10 gag pol
amp-R
MVA Del III Right Flank

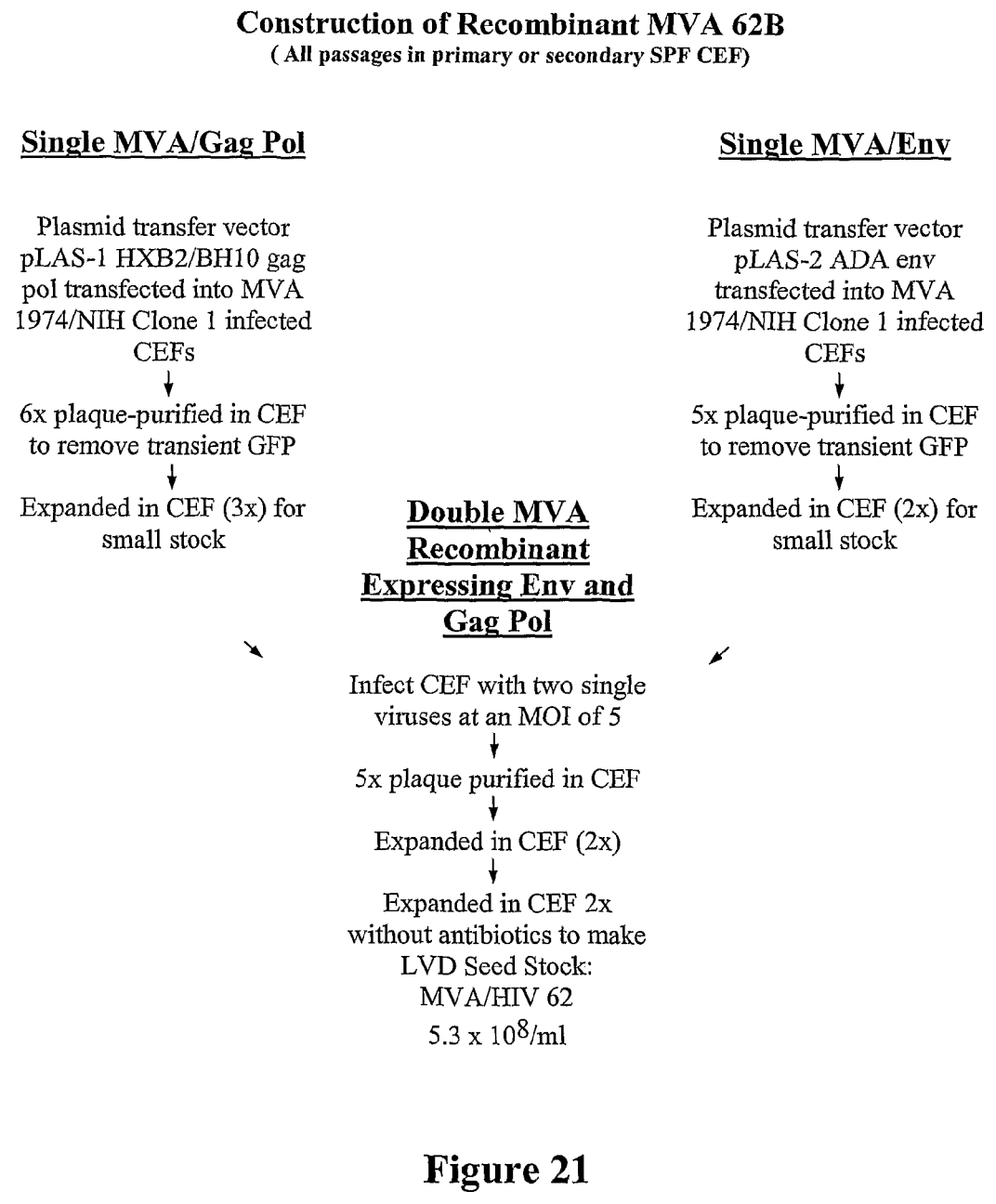

Construction of Recombinant MVA 62B
( All passages in primary or secondary SPF CEF)

Single MVA/Gag Pol

Plasmid transfer vector pLAS-1 HXB2/BH10 gag pol transfected into MVA 1974/NIH Clone 1 infected CEFs
↓
6x plaque-purified in CEF to remove transient GFP
↓
Expanded in CEF (3x) for small stock

Single MVA/Env

Plasmid transfer vector pLAS-2 ADA env transfected into MVA 1974/NIH Clone 1 infected CEFs
↓
5x plaque-purified in CEF to remove transient GFP
↓
Expanded in CEF (2x) for small stock

Double MVA Recombinant Expressing Env and Gag Pol

Infect CEF with two single viruses at an MOI of 5
↓
5x plaque purified in CEF
↓
Expanded in CEF (2x)
↓
Expanded in CEF 2x without antibiotics to make LVD Seed Stock: MVA/HIV 62 5.3 x $10^8$/ml

Figure 21

MVA 62B ADA env sequence

ATGAAAGTGAAGGGGATCAGGAAGAATTATCAGCACTTGTGGAAATGGGGCAT
CATGCTCCTTGGGATGTTGATGATCTGTAGTGCTGTAGAAAATTTGTGGGTCAC
AGTTTATTATGGGGTACCTGTGTGGAAAGAAGCAACCACCACTCTATTTTGTGC
ATCAGATGCTAAAGCATATGATACAGAGGTACATAATGTTTGGGCCACACATG
CCTGTGTACCCACAGACCCCAACCCACAAGAAGTAGTATTGGAAAATGTGACA
GAAAATTTTAACATGTGGAAAAATAACATGGTAGAACAGATGCATGAGGATAT
AATCAGTTTATGGGATCAAAGCCTAAAGCCATGTGTAAAATTAACCCCACTCTG
TGTTACTTTAAATTGCACTGATTTGAGGAATGTTACTAATATCAATAATAGTAG
TGAGGGAATGAGAGGAGAAATAAAAAACTGCTCTTTCAATATCACCACAAGCA
TAAGAGATAAGGTGAAGAAAGACTATGCACTTTTCTATAGACTTGATGTAGTA
CCAATAGATAATGATAATACTAGCTATAGGTTGATAAATTGTAATACCTCAACC
ATTACACAGGCCTGTCCAAAGGTATCCTTTGAGCCAATTCCCATACATTATTGT
ACCCCGGCTGGTTTTGCGATTCTAAAGTGTAAAGACAAGAAGTTCAATGGAAC
AGGGCCATGTAAAAATGTCAGCACAGTACAATGTACACATGGAATTAGGCCAG
TAGTGTCAACTCAACTGCTGTTAAATGGCAGTCTAGCAGAAGAAGAGGTAGTA
ATTAGATCTAGTAATTTCACAGACAATGCAAAAAACATAATAGTACAGTTGAA
AGAATCTGTAGAAATTAATTGTACAAGACCCAACAACAATACAAGGAAAAGTA
TACATATAGGACCAGGAAGAGCATTTTATACAACAGGAGAAATAATAGGAGAT
ATAAGACAAGCACATTGCAACATTAGTAGAACAAAATGGAATAACACTTTAAA
TCAAATAGCTACAAAATTAAAAGAACAATTTGGGAATAATAAAACAATAGTCT
TTAATCAATCCTCAGGAGGGGACCCAGAAATTGTAATGCACAGTTTTAATTGTG
GAGGGGAATTCTTCTACTGTAATTCAACACAACTGTTTAATAGTACTTGGAATT
TTAATGGTACTTGGAATTTAACACAATCGAATGGTACTGAAGGAAATGACACT
ATCACACTCCCATGTAGAATAAAACAAATTATAAATATGTGGCAGGAAGTAGG
AAAAGCAATGTATGCCCCTCCCATCAGAGGACAAATTAGATGCTCATCAAATA
TTACAGGGCTAATATTAACAAGAGATGGTGGAACTAACAGTAGTGGGTCCGAG
ATCTTCAGACCTGGGGGAGGAGATATGAGGGACAATTGGAGAAGTGAATTATA
TAAATATAAAGTAGTAAAAATTGAACCATTAGGAGTAGCACCCACCAAGGCAA
AAAGAAGAGTGGTGCAGAGAGAAAAAAGAGCAGTGGGAACGATAGGAGCTAT
GTTCCTTGGGTTCTTGGGAGCAGCAGGAAGCACTATGGGCGCAGCGTCAATAA
CGCTGACGGTACAGGCCAGACTATTATTGTCTGGTATAGTGCAACAGCAGAAC
AATTTGCTGAGGGCTATTGAGGCGCAACAGCATCTGTTGCAACTCACAGTCTGG
GGCATCAAGCAGCTCCAGGCAAGAGTCCTGGCTGTGGAAAGATACCTAAGGGA
TCAACAGCTCCTAGGGATTTGGGGTTGCTCTGGAAAACTCATCTGCACCACTGC
TGTGCCTTGGAATGCTAGTTGGAGTAATAAAACTCTGGATATGATTTGGGATAA
CATGACCTGGATGGAGTGGGAAAGAGAAATCGAAAATTACACAGGCTTAATAT
ACACCTTAATTGAGGAATCGCAGAACCAACAAGAAAAGAATGAACAAGACTT
ATTAGCATTAGATAAGTGGGCAAGTTTGTGGAATTGGTTTGACATATCAAATTG
GCTGTGGTATGTAAAAATCTTCATAATGATAGTAGGAGGCTTGATAGGTTTAAG
AATAGTTTTTACTGTACTTTCTATAGTAAATAGAGTTAGGCAGGGATACTCACC
ATTGTCATTTCAGACCCACCTCCCAGCCCCGAGGGGACCCGACAGGCCCGAAG
GAATCGAAGAAGAAGGTGGAGACAGAGACTAA

Figure 23

MVA 62B Gag Pol Sequence

ATGGGTGCGAGAGCGTCAGTATTAAGCGGGGGAGAATTAGATCGATGGGAAA
AAATTCGGTTAAGGCCAGGGGGAAAGAAAAAATATAAATTAAAACATATAGT
ATGGGCAAGCAGGGAGCTAGAACGATTCGCAGTTAATCCTGGCCTGTTAGAAA
CATCAGAAGGCTGTAGACAAATACTGGGACAGCTACAACCATCCCTTCAGACA
GGATCAGAAGAACTTAGATCATTATATAATACAGTAGCAACCCTCTATTGTGTG
CATCAAAGGATAGAGATAAAAGACACCAAGGAAGCTTTAGACAAGATAGAGG
AAGAGCAAAACAAAAGTAAGAAAAAAGCACAGCAAGCAGCAGCTGACACAGG
ACACAGCAATCAGGTCAGCCAAAATTACCCTATAGTGCAGAACATCCAGGGGC
AAATGGTACATCAGGCCATATCACCTAGAACTTTAAATGCATGGGTAAAAGTA
GTAGAAGAGAAGGCTTTCAGCCCAGAAGTGATACCCATGTTTTCAGCATTATC
AGAAGGAGCCACCCCACAAGATTTAAACACCATGCTAAACACAGTGGGGGGA
CATCAAGCAGCCATGCAAATGTTAAAAGAGACCATCAATGAGGAAGCTGCAGA
ATGGGATAGAGTGCATCCAGTGCATGCAGGGCCTATTGCACCAGGCCAGATGA
GAGAACCAAGGGGAAGTGACATAGCAGGAACTACTAGTACCCTTCAGGAACA
AATAGGATGGATGACAAATAATCCACCTATCCCAGTAGGAGAAATTTATAAAA
GATGGATAATCCTGGGATTAAATAAAATAGTAAGAATGTATAGCCCTACCAGC
ATTCTGGACATAAGACAAGGACCAAAAGAACCCTTTAGAGACTATGTAGACCG
GTTCTATAAAACTCTAAGAGCCGAGCAAGCTTCACAGGAGGTAAAAAATTGGA
TGACAGAAACCTTGTTGGTCCAAAATGCGAACCCAGATTGTAAGACTATTTTAA
AAGCATTGGGACCAGCGGCTACACTAGAAGAAATGATGACAGCATGTCAGGG
AGTAGGAGGACCCGGCCATAAGGCAAGAGTTTTGGCTGAAGCAATGAGCCAA
GTAACAAATTCAGCTACCATAATGATGCAGAGAGGCAATTTTAGGAACCAAAG
AAAGATTGTTAAGTGTTTCAATTGTGGCAAAGAAGGGCACACAGCCAGAAATT
GCAGGGCCCCTAGGAAAAAGGGCTGTTGGAAATGTGGAAAGGAAGGACACCA
AATGAAAGATTGTACTGAGAGACAGGCTAATTTTTTAGGGAAGATCTGGCCTT
CCTACAAGGGAAGGCCAGGGAATTTTCTTCAGAGCAGACCAGAGCCAACAGCC
CCACCAGAAGAGAGCTTCAGGTCTGGGGTAGAGACAACAACTCCCCCTCAGAA
GCAGGAGCCGATAGACAAGGAACTGTATCCTTTAACTTCCCTCAGATCACTCTT
TGGCAACGACCCCTCGTCACAATAAAGATAGGGGGGCAACTAAAGGAAGCTCT
ATTAGATACAGGAGCAGATGATACAGTATTAGAAGAAATGAGTTTGCCAGGAA
GATGGAAACCAAAAATGATAGGGGGAATTGGAGGTTTTATCAAAGTAAGACA
GTATGATCAGATACTCATAGAAATCTGTGGACATAAAGCTATAGGTACAGTAT
TAGTAGGACCTACACCTGTCAACATAATTGGAAGAAATCTGTTGACTCAGATTG
GTTGCACTTTAAATTTTCCCATTAGCCCTATTGAGACTGTACCAGTAAAATTAA
AGCCAGGAATGGATGGCCCAAAAGTTAAACAATGGCCATTGACAGAAGAAAA
AATAAAAGCATTAGTAGAAATTTGTACAGAAATGGAAAAGGAAGGGAAAATT
TCAAAAATTGGGCCTGAGAATCCATACAATACTCCAGTATTTGCCATAAAGAA
AAAAGACAGTACTAAATGGAGGAAATTAGTAGATTTCAGAGAACTTAATAAGA
GAACTCAAGACTTCTGGGAAGTTCAATTAGGAATACCACATCCCGCAGGGTTA
AAAAAGAAAAAATCAGTAACAGTACTGGATGTGGGTGATGCATATTTTTCAGT
TCCCTTAGATGAAGACTTCAGGAAGTATACTGCATTTACCATACCTAGTATAAA
CAATGAGACACCAGGGATTAGATATCAGTACAATGTGCTTCCACAGGGATGGA

Figure 24

AAGGATCACCAGCAATATTCCAAAGTAGCATGACAAAAATCTTAGAGCCTTTT
AAAAAACAAAATCCAGACATAGTTATCTATCAATACATGAACGATTTGTATGT
AGGATCTGACTTAGAAATAGGGCAGCATAGAACAAAAATAGAGGAGCTGAGA
CAACATCTGTTGAGGTGGGGACTTACCACACCAGACAAAAAACATCAGAAAGA
ACCTCCATTCCTTTGGATGGGTTATGAACTCCATCCTGATAAATGGACAGTACA
GCCTATAGTGCTGCCAGAAAAAGACAGCTGGACTGTCAATGACATACAGAAGT
TAGTGGGGAAATTGAATACCGCAAGTCAGATTTACCCAGGGATTAAAGTAAGG
CAATTATGTAAACTCCTTAGAGGAACCAAAGCACTAACAGAAGTAATACCACT
AACAGAAGAAGCAGAGCTAGAACTGGCAGAAAACAGAGAGATTCTAAAAGAA
CCAGTACATGGAGTGTATTATGACCCATCAAAAGACTTAATAGCAGAAATACA
GAAGCAGGGGCAAGGCCAATGGACATATCAAATTTATCAAGAGCCATTTAAAA
ATCTGAAAACAGGAAAATATGCAAGAATGAGGGGTGCCCACACTAATGATGTA
AAACAATTAACAGAGGCAGTGCAAAAAATAACCACAGAAAGCATAGTAATAT
GGGGAAAGACTCCTAAATTTAAACTACCCATACAAAAGGAAACATGGGAAAC
ATGGTGGACAGAGTATTGGCAAGCCACCTGGATTCCTGAGTGGGAGTTTGTTA
ATACCCCTCCTTTAGTGAAATTATGGTACCAGTTAGAGAAAGAACCCATAGTA
GGAGCAGAAACCTTCTATGTAGATGGGGCAGCTAACAGGGAGACTAAATTAGG
AAAAGCAGGATATGTTACTAACAAAGGAAGACAAAAGGTTGTCCCCCTAACTA
ACACAACAAATCAGAAAACTCAGTTACAAGCAATTTATCTAGCTTTGCAGGAT
TCAGGATTAGAAGTAAACATAGTAACAGACTCACAATATGCATTAGGAATCAT
TCAAGCACAACCAGATAAAAGTGAATCAGAGTTAGTCAATCAAATAATAGAGC
AGTTAATAAAAAAGGAAAAGGTCTATCTGGCATGGGTACCAGCACACAAAGG
AATTGGAGGAAATGAACAAGTAGATAAATTAGTCAGTGCTGGAATCAGGAAA
ATACTATTTTTAGATGGAATAGATAAGGCCCAAGATGAACATTAG

Figure 24, contd.

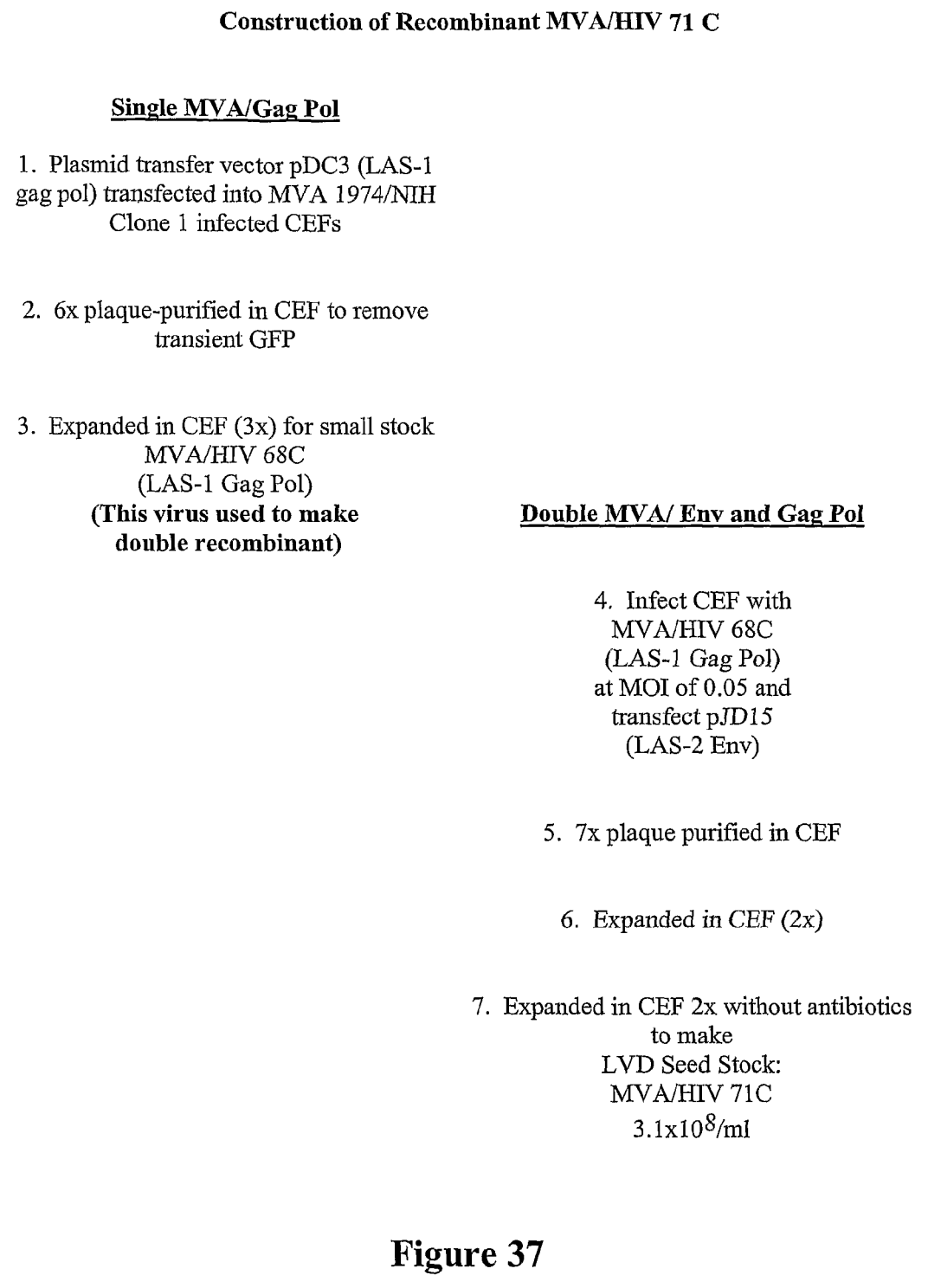

Construction of Recombinant MVA/HIV 71 C

Single MVA/Gag Pol

1. Plasmid transfer vector pDC3 (LAS-1 gag pol) transfected into MVA 1974/NIH Clone 1 infected CEFs 2. 6x plaque-purified in CEF to remove transient GFP 3. Expanded in CEF (3x) for small stock MVA/HIV 68C (LAS-1 Gag Pol) (This virus used to make double recombinant)

Double MVA/ Env and Gag Pol

4. Infect CEF with MVA/HIV 68C (LAS-1 Gag Pol) at MOI of 0.05 and transfect pJD15 (LAS-2 Env)

5. 7x plaque purified in CEF

6. Expanded in CEF (2x)

7. Expanded in CEF 2x without antibiotics to make LVD Seed Stock: MVA/HIV 71C $3.1x10^8$/ml

Figure 37

MVA/HIV 71C Env sequence:

ATGAGAGTGAAGGGGATACTGAGGAATTATCGACAATGGTGGATATGGGGCATCTTAG
GCTTTTGGATGTTAATGATTTGTAATGGAAACTTGTGGGTCACAGTCTATTATGGGGTA
CCTGTGTGGAAAGAAGCAAAAACTACTCTATTCTGTGCATCAAATGCTAAAGCATATG
AGAAAGAAGTACATAATGTCTGGGCTACACATGCCTGTGTACCCACAGACCCCAACCC
ACAAGAAATGGTTTTGGAAAACGTAACAGAAAATTTTAACATGTGGAAAAATGACATG
GTGAATCAGATGCATGAGGATGTAATCAGCTTATGGGATCAAAGCCTAAAGCCATGTG
TAAAGTTGACCCCACTCTGTGTCACTTTAGAATGTAGAAAGGTTAATGCTACCCATAAT
GCTACCAATAATGGGGATGCTACCCATAATGTTACCAATAATGGGCAAGAAATACAAA
ATTGCTCTTTCAATGCAACCACAGAAATAAGAGATAGGAAGCAGAGAGTGTATGCACT
TTTCTATAGACTTGATATAGTACCACTTGATAAGAACAACTCTAGTAAGAACAACTCTA
GTGAGTATTATAGATTAATAAATTGTAATACCTCAGCCATAACACAAGCATGTCCAAA
GGTCAGTTTTGATCCAATTCCTATACACTATTGTGCTCCAGCTGGTTATGCGATTCTAA
AGTGTAACAATAAGACATTCAATGGGACAGGACCATGCAATAATGTCAGCACAGTACA
ATGTACACATGGAATTAAGCCAGTGGTATCAACTCAGCTATTGTTAAACGGTAGCCTA
GCAGAAGGAGAGATAATAATTAGATCTGAAAATCTGACAGACAATGTCAAAACAATA
ATAGTACATCTTGATCAATCTGTAGAAATTGTGTGTACAAGACCCAACAATAATACAA
GAAAAAGTATAAGGATAGGGCCAGGACAAACATTCTATGCAACAGGAGGCATAATAG
GGAACATACGACAAGCACATTGTAACATTAGTGAAGACAAATGGAATGAAACTTTACA
AAGGGTGGGTAAAAAATTAGTAGAACACTTCCCTAATAAGACAATAAAATTTGCACCA
TCCTCAGGAGGGGACCTAGAAATTACAACACATAGCTTTAATTGTAGAGGAGAATTCT
TCTATTGCAGCACATCAAGACTGTTTAATAGTACATACATGCCTAATGATACAAAAAGT
AAGTCAAACAAAACCATCACAATCCCATGCAGCATAAAACAAATTGTAAACATGTGGC
AGGAGGTAGGACGAGCAATGTATGCCCCTCCCATTGAAGGAAACATAACCTGTAGATC
AAATATCACAGGAATACTATTGGTACGTGATGGAGGAGTAGATTCAGAAGATCCAGAA
AATAATAAGACAGAGACATTCCGACCTGGAGGAGGAGATATGAGGAACAATTGGAGA
AGTGAATTATATAAATATAAAGCGGCAGAAATTAAGCCATTGGGAGTAGCACCCACTC
CAGCAAAAAGGAGAGTGGTGGAGAGAGAAAAAAGAGCAGTAGGATTAGGAGCTGTGT
TCCTTGGATTCTTGGGAGCAGCAGGAAGCACTATGGGCGCAGCGTCAATAACGCTGAC
GGTACAGGCCAGACAATTGTTGTCTGGTATAGTGCAACAGCAAAGCAATTTGCTGAGG
GCTATCGAGGCGCAACAGCATCTGTTGCAACTCACGGTCTGGGGCATTAAGCAGCTCC
AGACAAGAGTCCTGGCTATCGAAAGATACCTAAAGGATCAACAGCTCCTAGGGCTTTG
GGGCTGCTCTGGAAAACTCATCTGCACCACTAATGTACCTTGGAACTCCAGTTGGAGTA
ACAAATCTCAAACAGATATTTGGGAAAACATGACCTGGATGCAGTGGGATAAAGAAGT
TAGTAATTACACAGACACAATATACAGGTTGCTTGAAGACTCGCAAACCCAGCAGGAA
AGAAATGAAAAGGATTTATTAGCATTGGACAATTGGAAAAATCTGTGGAATTGGTTTA
GTATAACAAACTGGCTGTGGTATATAAAAATATTCATAATGATAGTAGGAGGCTTGAT
AGGCTTAAGAATAATTTTTGCTGTGCTTTCTATAGTGAATAGAGTTAGGCAGGGATACT
CACCTTTGTCGTTTCAGACCCTTACCCCAAACCCAAGGGGACCCGACAGGCTCGGAAG
AATCGAAGAAGAAGGTGGAGGGCAAGACAGAGACTAA

Figure 39

MVA/HIV 71C Gag Pol sequence:

ATGGGTGCGAGAGCGTCAATATTAAGAGGGGGAAAATTAGATAAATGGGAAAAGATTAGGTTAAGGCCAG
GGGGAAAGAAACACTATATGCTAAAACACCTAGTATGGGCAAGCAGGGAGCTGGAAAGATTTGCACTTAA
CCCTGGCCTTTTAGAGACATCAGAAGGCTGTAAACAAATAATAAAACAGCTACAACCAGCTCTTCAGACAG
GAACAGAGGAACTTAGGTCATTATTCAATGCAGTAGCAACTCTCTATTGTGTACATGCAGACATAGAGGTA
CGAGACACCAAAGAAGCATTAGACAAGATAGAGGAAGAACAAAACAAAAGTCAGCAAAAAACGCAGCAG
GCAAAAGAGGCTGACAAAAAGGTCGTCAGTCAAAATTATCCTATAGTGCAGAATCTTCAAGGGCAAATGGT
ACACCAGGCACTATCACCTAGAACTTTGAATGCATGGGTAAAAGTAATAGAAGAAAAAGCCTTTAGCCCGG
AGGTAATACCCATGTTCACAGCATTATCAGAAGGAGCCACCCCACAAGATTTAAACACCATGTTAAATACC
GTGGGGGGACATCAAGCAGCCATGCAAATGTTAAAAGATACCATCAATGAGGAGGCTGCAGAATGGGATA
GATTACATCCAGTACATGCAGGGCCTGTTGCACCAGGCCAAATGAGAGAACCAAGGGGAAGTGACATAGC
AGGAACTACTAGTAACCTTCAGGAACAAATAGCATGGATGACAAGTAACCCACCTATTCCAGTGGGAGATA
TCTATAAAAGATGGATAATTCTGGGGTTAAATAAAATAGTAAGAATGTATAGCCCTGTCAGCATTTTAGAC
ATAAGACAAGGGCCAAAGGAACCCTTTAGAGATTATGTAGACCGGTTCTTTAAAACTTTAAGAGCTGAACA
AGCTTCACAAGATGTAAAAAATTGGATGGCAGACACCTTGTTGGTCCAAAATGCGAACCCAGATTGTAAGA
CCATTTTAAGAGCATTAGGACCAGGAGCTACATTAGAAGAAATGATGACAGCATGTCAAGGAGTGGGAGG
ACCTAGCCACAAAGCAAGAGTGTTGGCTGAGGCAATGAGCCAAACAGGCAGTACCATAATGATGCAGAGA
AGCAATTTTAAAGGCTCTAAAAGAACTGTTAAATGCTTCAACTGTGGCAAGGAAGGGCACATAGCTAGAAA
TTGCAGGGCCCCTAGGAAAAAAGGCTGTTGGAAATGTGGAAAGGAAGGACACCAAATGAAAGACTGTGCT
GAGAGGCAGGCTAATTTTTTAGGGAAAATTTGGCCTTCCCACAAGGGGAGGCCAGGGAATTTCCTTCAGAA
CAGGCCAGAGCCAACAGCCCCACCAGCAGAGAGCTTCAGGTTCGAGGAGACAACCCCTGCTCCGAAGCAG
GAGCTGAAAGACAGGGAACCCTTAACCTCCCTCAAATCACTCTTTGGCAGCGACCCCTTGTCTCAATAAAA
ATAGGGGGCCAGATAAAGGAGGCTCTCTTAGACACAGGAGCAGATGATACAGTATTAGAAGAAATGAATT
TGCCAGGAAAATGGAAACCAAAAATGATAGGAGGAATTGGAGGTTTTATCAAAGTAAGACAGTATGATCA
AATACTTATAGAAATTTGTGGAAAAAAGGCTATAGGTACAGTATTAGTAGGACCCACACCTGTCAACATAA
TTGGAAGAAATATGCTGACTCAGATTGGATGCACGCTAAATTTTCCAATTAGTCCCATTGAAACTGTACCAG
TAAAATTAAAGCCAGGAATGGATGGCCCAAAGGTTAAACAATGGCCATTGACAGAGGAGAAAATAAAAGC
ATTAACAGCAATTTGTGATGAAATGGAGAAGGAAGGAAAAATTACAAAAATTGGGCCTGAAAATCCATAT
AACACTCCAATATTCGCCATAAAAAAGAAGGACAGTACTAAGTGGAGAAAATTAGTAGATTTCAGAGAACT
TAATAAAAGAACTCAAGACTTCTGGGAAGTTCAATTAGGAATACCACACCCAGCAGGGTTAAAAAAGAAA
AAATCAGTGACAGTACTAGATGTGGGGGATGCATATTTTTCAGTTCCTTTAGATGAAAGCTTTAGGAGGTAT
ACTGCATTCACCATACCTAGTAGAAACAATGAAACACCAGGGATTAGATATCAATATAATGTGCTTCCACA
AGGATGGAAAGGATCACCAGCAATATTCCAGAGTAGCATGACAAAAATCTTAGAGCCCTTTAGAGCACAA
AATCCAGAAATAGTCATCTATCAATATATGAATGACTTGTATGTAGGATCTGACTTAGAAATAGGGCAACA
TAGAGCAAAGATAGAGGAATTAAGAGAACATCTATTAAGGTGGGGATTTACCACACCAGACAAGAAACAT
CAGAAAGAACCCCCATTTCTTTGGATGGGGTATGAACTCCATCCTGACAAATGGACAGTACAGCCTATACA
GCTGCCAGAAAAGGAGAGCTGGACTGTCAATGATATACAGAAGTTAGTGGGAAAATTAAACACGGCAAGC
CAGATTTACCCAGGGATTAAAGTAAGACAACTTTGTAGACTCCTTAGAGGGGCCAAAGCACTAACAGACAT
AGTACCACTAACTGAAGAAGCAGAATTAGAATTGGCAGAGAACAGGGAAATTCTAAAAGAACCAGTACAT
GGAGTATATTATGACCCTTCAAAAGACTTGATAGCTGAAATACAGAAACAGGGACATGACCAATGGACATA
TCAAATTTACCAAGAACCATTCAAAAATCTGAAAACAGGGAAGTATGCAAAAATGAGGACTGCCCACACTA
ATGATGTAAAACGGTTAACAGAGGCAGTGCAAAAAATAGCCTTAGAAAGCATAGTAATATGGGGAAAGAT
TCCTAAACTTAGGTTACCCATCCAAAAAGAAACATGGGAGACATGGTGGACTGACTATTGGCAAGCCACCT
GGATTCCTGAGTGGGAATTTGTTAATACTCCTCCCCTAGTAAAATTATGGTACCAGCTAGAGAAGGAACCC
ATAATAGGAGTAGAAACTTTCTATGTAGATGGAGCAGCTAATAGGGAAACCAAAATAGGAAAAGCAGGGT
ATGTTACTGACAGAGGAAGGCAGAAAATTGTTTCTCTAACTGAAACAACAAATCAGAAGACTCAATTACAA
GCAATTTATCTAGCTTTGCAAGATTCAGGATCAGAAGTAAACATAGTAACAGACTCACAGTATGCATTAGG
AATTATTCAAGCACAACCAGATAAGAGTGAATCAGGGTTAGTCAACCAAATAATAGAACAATTAATAAAA
AAGGAAAGGGTCTACCTGTCATGGGTACCAGCACATAAAGGTATTGGAGGAAATGAACAAGTAGACAAAT
TAGTAAGTAGTGGAATCAGGAGAGTGCTATAG

Figure 40

A
IC25 IC1-90 IC48
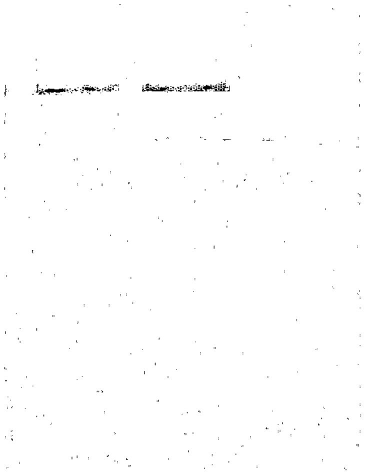
p55
p41
p24
B
| Plasmid | Protease mutations | Aggregates | VLP |
|---|---|---|---|
| IC25 | D25N | - | p55 |
| IC1-90 | R70G, M90L | - | p55 and p41 |
| IC48 | G48V | + | P55, p41 and p24 |
C
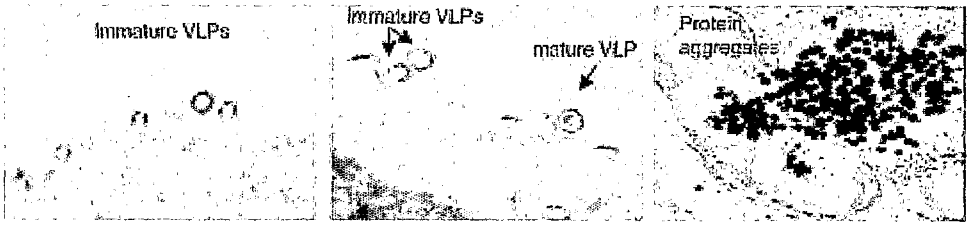
IC1-90 IC48 IC48
Figure 41

RECOMBINANT MVA VIRUSES EXPRESSING CLADE A/G, CLADE B, AND CLADE C MODIFIED HIV ENV, GAG AND POL GENES

CROSS-REFERENCE TO RELATED APPLICATIONS

This application claims the benefit of U.S. Provisional Patent Application No. 60/604,918 filed Aug. 27, 2004, the entire disclosure of which is hereby expressly incorporated by reference.

STATEMENT REGARDING FEDERALLY FUNDED RESEARCH

This invention was made with government support under Grant AI049364 awarded by the National Institutes of Health. The government has certain rights in the invention

FIELD OF THE INVENTION

The invention provides modified vaccinia Ankara (MVA), a replication-deficient strain of vaccinia virus, expressing human immunodeficiency virus (HIV) env, gag, and pol genes.

DESCRIPTION OF THE RELATED ART

Many novel candidates and approaches have been developed in the pursuit to identify an effective human immunodeficiency virus (HIV) vaccine. The induction of strong cell-mediated immunity and broadly reactive anti-envelope antibodies that can neutralize primary HIV-1 may be necessary in the making of an effective HIV-1 vaccine, and the ideal vaccine may need to induce both T and B cell responses. Plasmid DNA vaccination can elicit both humoral and cellular immune responses (Tang et al. 1992 *Nature* 356: 152-154; Ulmer et al. 1993 *Science* 259:1745-1749; and Wolff et al. 1990 *Science* 247:1465-1468) that protect non-human primates against challenges with nonpathogenic AIDS viruses (Boyer et al. 1997 *Nat. Med.* 3:526-532; and Letvin et al. 1997 *PNAS U.S.A.* 94:9378-9383.) and afford modest protection against disease from pathogenic simian immunodeficiency virus (SIV) (Egan et al. 2000 *J. Virol.* 74:7485-7495; and Lu et al. 1996 *J. Virol.* 70: 3978-3991).

Vaccines that have been designed to raise cellular immunity can in some cases control virulent viral challenges and prevent the development of AIDS in rhesus macaques (Amara et al. 2001 *Science* 292: 69-74; Barouch et al. 2000 *Science* 290: 486-492; Barouch et al. 2001 *J. Virol.* 75:5151-5158; Rose et al. 2001 *Cell* 106:539-549; and Shiver et al. 2002 *Nature* 415: 331-335). Priming the immune response with plasmid DNA followed by a recombinant poxvirus booster such as the modified vaccinia virus Ankara (Amara et al. 2001 *Science* 292:69-74 and Robinson et al. 2000 *AIDS Rev.* 2:105-110) or a VLP-protein boost plus IL-12/GM-CSF (O'Neill et al. 2003 *AIDS Res. Hum. Retrovir.* 19: 883-890 and O'Neill et al. 2002 *J. Med. Primatol.* 31: 217-227) are two of the many different approaches to raising cellular immunity. Including multiple HIV-1 gene regions on the same vector augments the DNA prime-MVA boost approach, as both gag and env responses are important to protection against virus challenge (Amara et al. 2002 *J. Virol.* 76:6138-6146). Lacking this potential advantage are HIV-1 DNA vaccines that encode only Gag or encode Gag, Env, and other viral proteins on separate DNA constructs (Barouch et al. 2000 *Science* 290: 486-492; Barouch et al. 2002 *Nature* 415:335-339 and Kang et al. 1999 *Biol. Chem.* 380: 353-364). Escape by HIV is possible when the immune response is driven by a single dominant epitope (Barouch et al. 2000 *Science* 290: 486-492; Barouch et al. 2002 *Nature* 415:335-339 and Mortara et al. 1998 *J. Virol.* 72: 1403-1410); thus, a multi-epitope or multi-protein response appears advantageous.

It is well established that VLP assembly and release from cells depend on proper intracellular protease regulation to preserve the Gag polyprotein (Gottlinger et al 1989 *PNAS USA* 86: 5781-5785; Karacostas et al. 1993 *Virology* 193: 661-671 and Peng et al. 1989 *J. Virol.* 63:2550-2556) and may be observed upon transfection of Gag-only expression systems (Huang et al. 2001 *J. Virol.* 75: 4947-4951; Kang et al. 1999 *Biol. Chem.* 380: 353-364 and Schneider et al. 1997 *J. Virol.* 71:4892-4903). Previous studies demonstrated that alteration of the 25th residue of protease, from Asp (D) to Asn (N), resulted in complete loss of protease activity (Gottlinger et al. 1989 *PNAS USA* 86: 5781-5785; Kohl et al. 1988 *PNAS USA* 85:4686-4690 and Loeb et al. 1989 *J. Virol.* 63: 111-121). Furthermore, Jacobsen et al. (1995 *Virology* 206:527-534) demonstrated that mutagenesis of protease at positions 48 (G48V) and 90 (M90L) led to less efficient enzymatic activity and delayed processing of the gag and gag-pol polyproteins. Protease mutations at either amino acid positions 48 and 90 delay, but do not abolish, protease enzymatic activity, unlike the D25N mutation, and permit production of infectious virus when present within an otherwise wild-type provirus. A recent study suggested that the two protease mutations at positions 48 and 90 are not limiting, not only in terms of high-level production of HIV-1 proteins, but also with regard to assembly of VLPs (Ellenberger et al. 2004 *Virology* 319: 118-130).

One of the most promising HIV vaccines is the heterologous prime-boost approach. The prime may consist of a recombinant plasmid DNA or viral vector-expressing HIV proteins. The heterologous boost would be a recombinant viral vector (poxvirus or adenovirus) or second viral vector, optimizing the boost for the vaccine insert immunogen and not the vector itself. Using the same recombinant viral vector for the prime and boost may lead to a diminished immune response similar to preexisting immunity to the recombinant vector (Vogels et al 2003 *J. Virol.* 77: 8263-8271). Priming with a recombinant plasmid DNA and boosting with a recombinant MVA enhances the cellular responses to a common immunogen contained in both vectors (Amara et al. 2001 *Science* 292: 69-74; Hanke et al. 1998 *Vaccine* 16: 439-445; Schneider et al. 1998 *Nat. Med.* 4: 397-402; and Schneider et al. 2001 *Vaccine* 19: 4595-4602). At the peak effector phase of the immune response to the vaccine protocol, induced CD8 cells can reach very high frequencies of total CD8 cells (Allen et al 2000 *J. Immunol.* 164:4968-4978; Amara et al. 2001 *Science* 292: 69-74; and Horton et al. 2002 *J. Virol.* 76: 7187-7202).

SUMMARY OF THE INVENTION

The invention is related to a pharmaceutical composition comprising a recombinant MVA virus expressing an HIV env, gag, and pol gene or modified gene thereof for production of an HIV Env, Gag, and Pol antigen by expression from said recombinant MVA virus, where the HIV env gene is modified to encode an HIV Env protein composed of gp120 and the membrane-spanning and ectodomain of gp41 but lacking part or all of the cytoplasmic domain of gp41, and a pharmaceutically acceptable carrier; where the HIV env, gag, or pol gene or modified gene thereof is taken from clade AG and said HIV env gene or modified gene thereof has SEQ ID NO: 1 or a sequence having at least about 97%, 98%, 99% or 99.9% identity thereto, and the HIV gag and pol gene(s) or modified gene(s) thereof has SEQ ID NO: 2 or a sequence having at least about 97%, 98%, 99% or 99.9% identity thereto; or the HIV env, gag, or pol gene or modified gene thereof is taken from clade B and the HIV env gene or modified gene thereof has SEQ ID NO: 3 or a sequence having at least about 97%, 98%, 99% or 99.9% identity thereto, and the HIV gag and pol gene(s) or modified gene(s) thereof has SEQ ID NO: 4 or a sequence having at least about 97%, 98%, 99% or 99.9% identity thereto; or the HIV env, gag, or pol gene or modified gene thereof is taken from clade C and the HIV env gene or modified gene thereof has SEQ ID NO: 5 or a sequence having at least about 97%, 98%, 99% or 99.9% identity thereto, and the HIV gag and pol gene(s) or modified gene(s) thereof has SEQ ID NO: 6 or a sequence having at least about 97%, 98%, 99% or 99.9% identity thereto; and related methods of making and methods of using thereof.

BRIEF DESCRIPTION OF THE DRAWINGS

FIG. 3. Tropic and biologic properties of HIV-1 isolates.

FIG. 9. Flow chart "Construction of recombinant MVA 65A/G".

FIG. 12. MVA 65A/G Env sequence (SEQ ID NO: 1).

FIG. 13. MVA 65A/G GagPol Sequence (SEQ ID NO: 2).

FIG. 21. Flow chart "Construction of recombinant MVA 62B".

FIG. 23. MVA 62B ADA Env sequence (SEQ ID NO: 3).

FIG. 24. HXB2/BH10 Gag Pol Sequence in MVA 62B (SEQ ID NO: 4).

FIG. 37. Flow chart "Construction of recombinant MVA/HIV 71C".

FIG. 39. MVA/HIV 71C Env sequence (SEQ ID NO: 5).

FIG. 40. MVA/HIV 71C Gag Pol sequence (SEQ ID NO: 6).

FIG. 41. Analysis of HIV-1-like particles. (A) immunoblot analysis of sucrose-gradient-purified VLP using rabbit polyclonal anti-p24. The positions of HIV precursors and products are indicated on the right. Fraction 9 from each gradient was separated by SDS-PAGE, transferred to nitrocellulose, and analyzed by immunoblotting. Vaccine construct pGA1/IC25 (complete ablation of HIV protease activity) is included as reference (Ellenberger, D. et al. 2004 *Virology* 319:118-130). (B) summary of protease mutations introduced in vaccine constructs and demonstrable expression products. (C) transmission electron microscopy of VLPs and intracellular protein aggregates in 293T cells transfected with vaccine constructs IC1-90 and IC48.

Env, and 1 Tat). ELISPOT responses recorded as positive for each peptide pool per animal are indicated.

Figure 45:
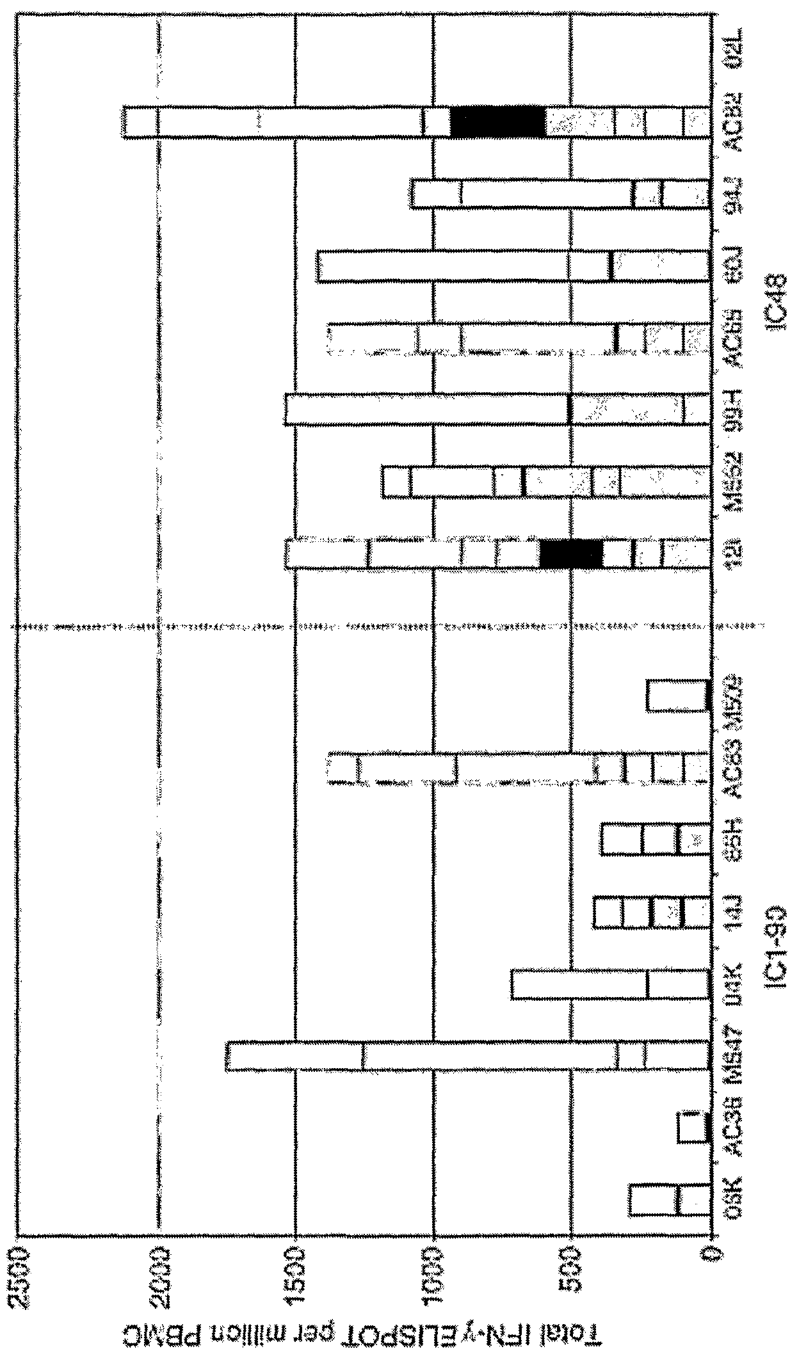

FIG. 45. ELISPOT responses determined 8 weeks after the MVA booster. Designations below the panels indicate individual animals and the DNA prime group (8 animals/group). Stacked bars indicate ELISPOT response to individual peptide pools for each animal. White bars represent Gag peptide pools, filled dark bars represent Pol peptide pools, and light-colored gray bars represent Env peptide pools. The background value was subtracted before conversion to 1 million PBMC.

Figure 46:
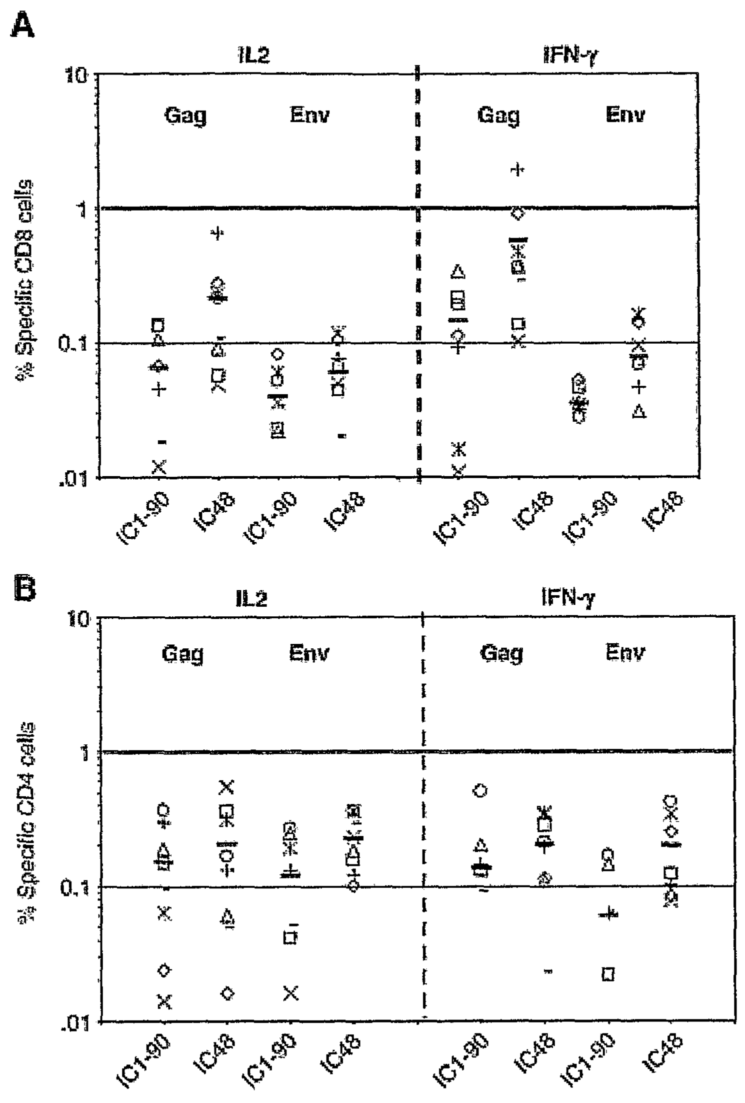

FIG. 46. Responding CD8 and CD4 cells determined by IFN-γ and IL2 intracellular cytokine staining. (A) Percent-specific CD8 cells responding to Gag and Env for individual animals at peak (1 week after the MVA booster). The bold bar indicates the arithmetic mean height for the response in each group. Designations above the panels specify the measured cytokine (IFN-γ or IL2) and designations below the panels specify the DNA prime group. Symbols indicate the individual animals. (B) Percent-specific CD4 cells responding to Gag and Env for individual animals at peak (1 week after the MVA booster). Designations above and below the panels are the same as in panel A.

Figure 47:
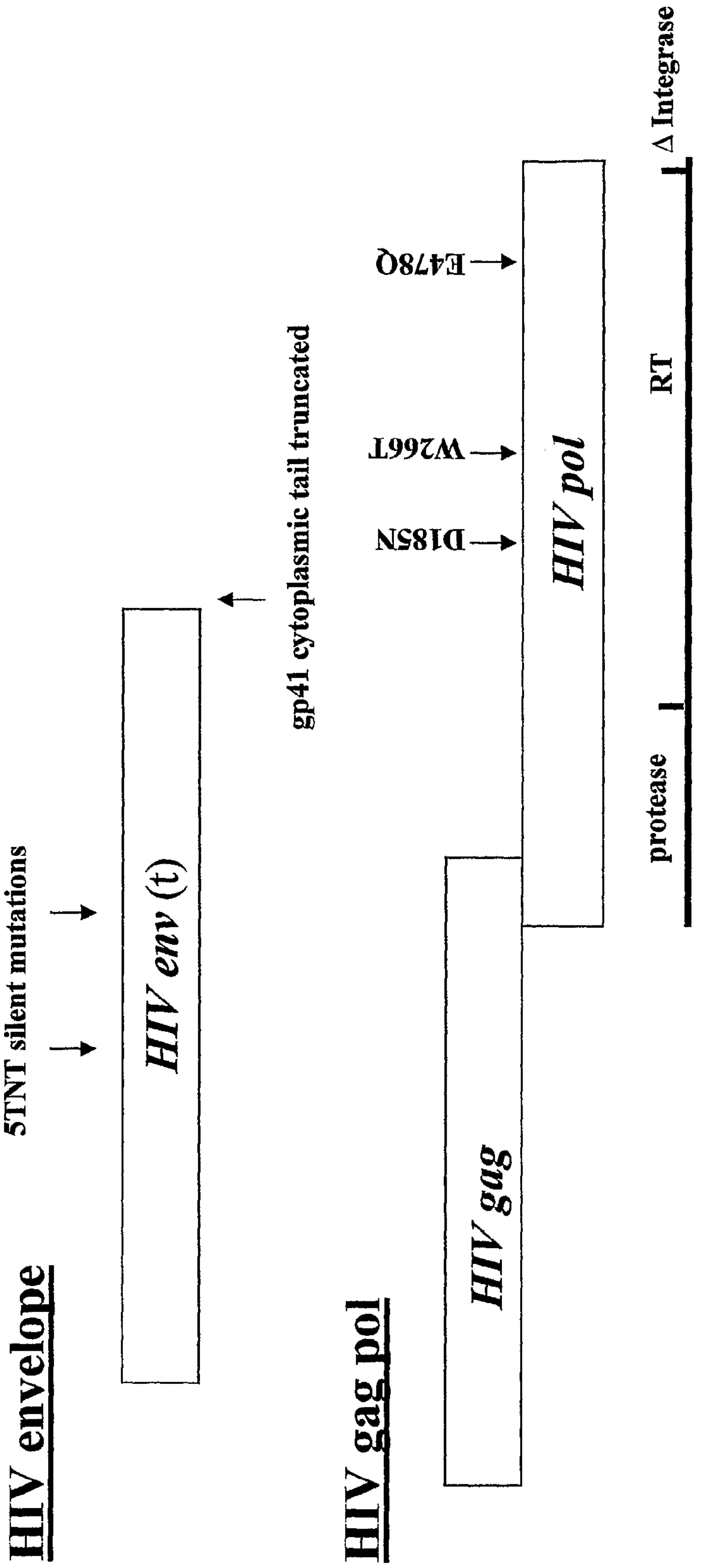

FIG. 47. Modifications to HIV genes. In the HIV env gene, vaccinia early termination signals were removed by making silent mutations and part of the gp 41 cytoplasmic tail was truncated. In the pol gene, three mutations were made in RT and the integrase was deleted.

Figure 48:
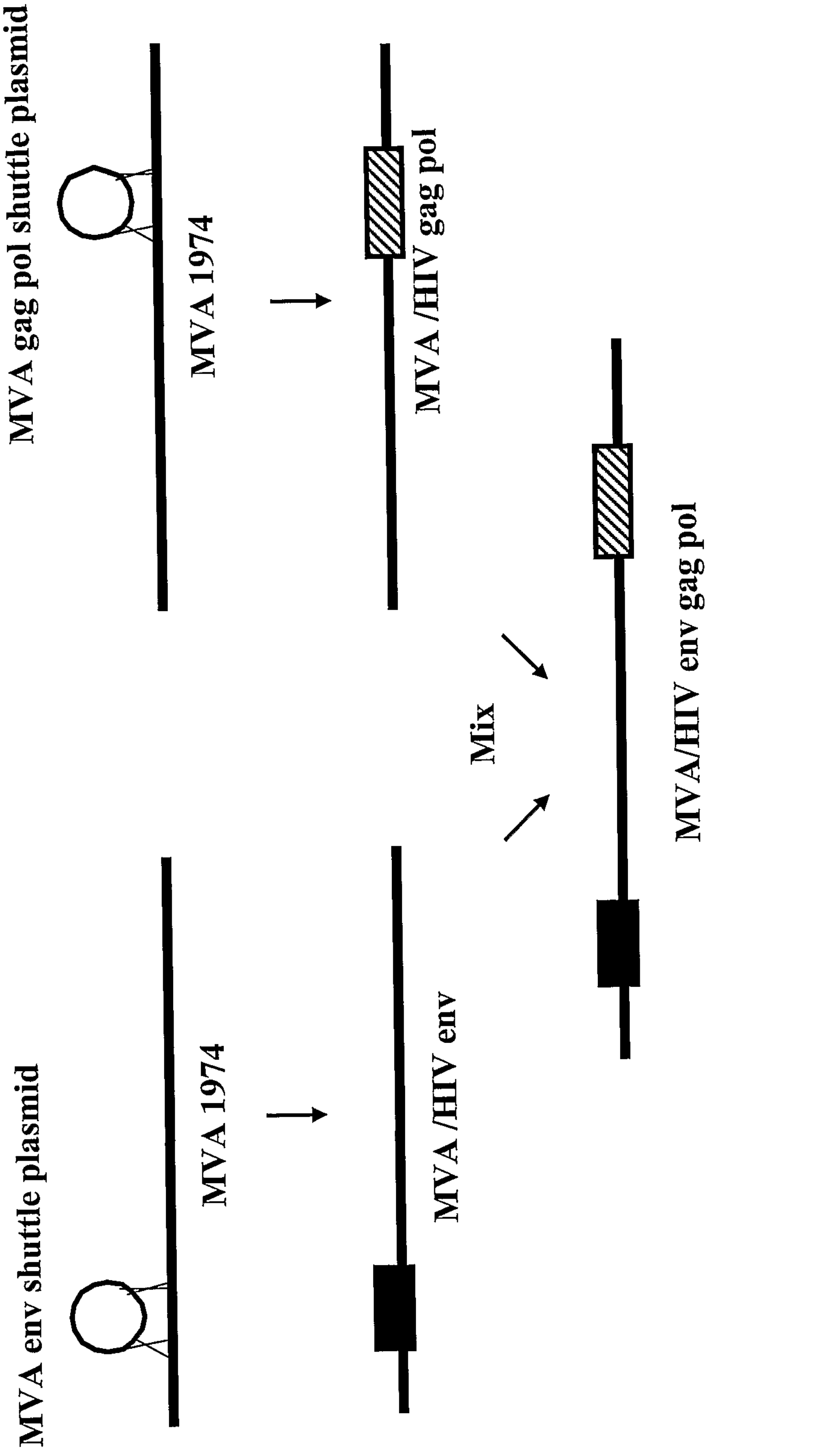

FIG. 48. Recombinant MVA/HIV construction. Single recombinant viruses were made by homologous recombination of MVA and MVA env or gag shuttle plasmids containing transient GFP, and expression of the HIV gene controlled by the early/late modified H5 vaccinia promoter. The double recombinant was made by infecting both single recombinants at an MOI of 5 pfu/cell, and plating out the harvest to pick individual plaques. The plaques were characterized by immunostaining and those plaques expressing both Env and Gag proteins were plaque purified further to obtain the double recombinant.

DEPOSIT OF MICROORGANISM

The following microorganism has been deposited in accordance with the terms of the Budapest Treaty with the American Type Culture Collection (ATCC), Manassas, Va., on the date indicated:

| Microorganism | Accession No. | Date |
|---|---|---|
| MVA 1974/NIH Clone 1 | PTA-5095 | Mar. 27, 2003 |

MVA 1974/NIH Clone 1 was deposited as ATCC Accession No.: PTA-5095 on Mar. 27, 2003 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited strain is not to be construed as a license to practice the invention in contravention of the rights granted under the authority of any government in accordance with its patent laws.

DETAILED DESCRIPTION OF THE PREFERRED EMBODIMENT

Recombinant MVA Virus

Vaccinia virus, a member of the genus Orthopoxvirus in the family of Poxyiridae, was used as live vaccine to immunize against the human smallpox disease. Successful worldwide vaccination with vaccinia virus culminated in the eradication of variola virus, the causative agent of the smallpox ("The global eradication of smallpox. Final report of the global commission for the certification of smallpox eradication". History of Public Health, No. 4, Geneva: World Health Organization, 1980). Since that WHO declaration, vaccination has been universally discontinued except for people at high risk of poxvirus infections (e.g. laboratory workers).

More recently, vaccinia viruses have also been used to engineer viral vectors for recombinant gene expression and for the potential use as recombinant live vaccines (Mackett, M. et al 1982 *PNAS USA* 79:7415-7419; Smith, G. L. et al. 1984 *Biotech Genet Engin Rev* 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385). The recombinant vaccinia viruses prepared in this way can be used, on the one hand, as live vaccines for the prophylaxis of infectious diseases, on the other hand, for the preparation of heterologous proteins in eulcaryotic cells.

For vector applications health risks would be lessened by the use of a highly attenuated vaccinia virus strain. Several such strains of vaccinia virus were especially developed to avoid undesired side effects of smallpox vaccination. Thus, the modified vaccinia Ankara (MVA) has been generated by long-term serial passages of the Ankara strain of vaccinia virus (CVA) on chicken embryo fibroblasts (for review see Mayr, A. et al. 1975 *Infection* 3:6-14; Swiss Patent No. 568,392). The MVA virus is publicly available from American Type Culture Collection as ATCC No.: VR-1508. MVA is distinguished by its great attenuation, that is to say by diminished virulence and ability to replicate in primate cells while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 *J Gen Virol* 72:1031-1038). The resulting MVA virus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr A. et al. 1978 *Zentralbl Bakteriol [B]* 167:375-390; Stickl et al. 1974 *Dtsch Med Wschr* 99:2386-2392). During these studies in over 120,000 humans, including high-risk patients, no side effects were associated with the use of MVA vaccine.

MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. 1992 *PNAS USA* 89:10847-10851). Additionally, novel vaccinia vector vaccines were established on the basis of MVA having foreign DNA sequences inserted at the site of deletion III within the MVA genome (Sutter, G. et al. 1994 Vaccine 12:1032-1040).

The recombinant MVA vaccinia viruses can be prepared as set out hereinafter. A DNA-construct which contains a DNA-sequence which codes for a foreign polypeptide flanked by MVA DNA sequences adjacent to a naturally occurring deletion, e.g. deletion III, or other non-essential sites, within the MVA genome, is introduced into cells infected with MVA, to allow homologous recombination. Once the DNA-construct has been introduced into the eulcaryotic cell and the foreign DNA has recombined with the viral DNA, it is possible to isolate the desired recombinant vaccinia virus in a manner known per se, preferably with the aid of a marker. The DNA-construct to be inserted can be linear or circular. A plasmid or polymerase chain reaction product is preferred. The DNA-construct contains sequences flanking the left and the right side of a naturally occurring deletion, e.g. deletion III, within the MVA genome. The foreign DNA sequence is inserted between the sequences flanking the naturally occurring deletion. For the expression of a DNA sequence or gene, it is necessary for regulatory sequences, which are required for the transcription of the gene, to be present on the DNA. Such regulatory sequences (called promoters) are known to those skilled in the art, and include for example those of the vaccinia 11 kDa gene as are described in EP-A-198,328, and those of the 7.5 kDa gene (EP-A-110,385). The DNA-construct can be introduced into the MVA infected cells by transfection, for example by means of calcium phosphate precipitation (Graham et al. 1973 *Virol* 52:456-467; Wigler et al. 1979 *Cell* 16:777-785), by means of electroporation (Neumann et al. 1982 *EMBO J.* 1:841-845), by microinjection (Graessmann et al. 1983 *Meth Enzymol* 101:482-492), by means of liposomes (Straubinger et al. 1983 *Meth Enzymol* 101:512-527), by means of spheroplasts (Schaffher 1980 *PNAS USA* 77:2163-2167) or by other methods known to those skilled in the art.

HIVs and their Replication

Figure 1:
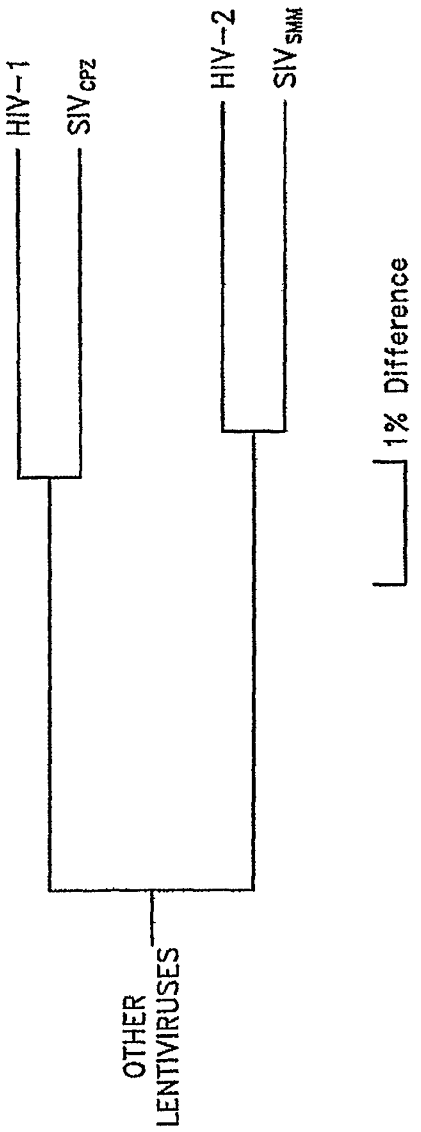
FIG. 1. Phylogenetic relationships of HIV-1 and HIV-2 based on identity of pol gene sequences. $SIV_{cpz}$ and $SIV_{smm}$ are subhuman primate lentiviruses recovered from a chimpanzee and sooty mangabey monkey, respectively.

The etiological agent of acquired immune deficiency syndrome (AIDS) is recognized to be a retrovirus exhibiting characteristics typical of the lentivirus genus, referred to as human immunodeficiency virus (HIV). The phylogenetic relationships of the human lentiviruses are shown in FIG. 1. HIV-2 is more closely related to $SIV_{smm}$, a virus isolated from sooty mangabey monkeys in the wild, than to HIV-1. It is currently believed that HIV-2 represents a zoonotic transmission of $SIV_{smm}$ to man. A series of lentiviral isolates from captive chimpanzees, designated $SIV_{cpz}$, are close genetic relatives of HIV-1.

Figure 2:
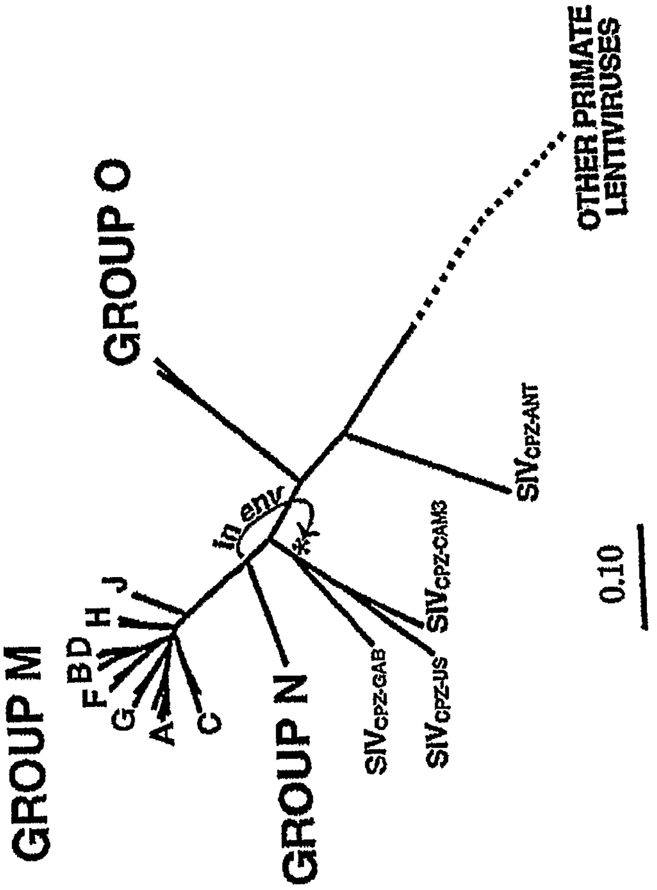
FIG. 2. Phylogenetic relationships of HIV-1 groups M, N and O with four different $SIV_{cpz}$ isolates based on full-length pol gene sequences. The bar indicates a genetic distance of 0.1 (10% nucleotide divergence) and the asterisk positions group N HIV-1 isolates based on env sequences.

The earliest phylogenetic analyses of HIV-1 isolates focused on samples from Europe/North America and Africa; discrete clusters of viruses were identified from these two areas of the world. Distinct genetic subtypes or clades of HIV-1 were subsequently defined and classified into three groups: M (major); O (outlier); and N (non-M or O) (FIG. 2). The M group of HIV-1, which includes over 95% of the global virus isolates, consists of at least eight discrete clades (A, B, C, D, F, G, H, and J), based on the sequence of complete viral genomes. Members of HIV-1 group O have been recovered from individuals living in Cameroon, Gabon, and Equatorial Guinea; their genomes share less than 50% identity in nucleotide sequence with group M viruses. The more recently discovered group N HIV-I strains have been identified in infected Cameroonians, fail to react serologically in standard whole-virus enzyme-linked immunosorbent assay (ELISA), yet are readily detectable by conventional Westein blot analysis.

Most current knowledge about HIV-1 genetic variation comes from studies of group M viruses of diverse geographic origin. Data collected during the past decade indicate that the HIV-1 population present within an infected individual can vary from 6% to 10% in nucleotide sequence. HIV-1 isolates within a clade may exhibit nucleotide distances of 15% in gag and up to 30% in gp120 coding sequences. Interclade genetic variation may range between 30% and 40% depending on the gene analyzed.

All of the HIV-1 group M subtypes can be found in Africa. Clade A viruses are genetically the most divergent and were the most common HIV-1 subtype in Africa early in the epidemic. With the rapid spread of HIV-1 to southern Africa during the mid to late 1990s, clade C viruses have become the dominant subtype and now account for 48% of HIV-1 infections worldwide. Clade B viruses, the most intensively studied HIV-1 subtype, remain the most prevalent isolates in Europe and North America.

High rates of genetic recombination are a hallmark of retroviruses. It was initially believed that simultaneous infections by genetically diverse virus strains were not likely to be established in individuals at risk for HIV-1. By 1995, however, it became apparent that a significant fraction of the HIV-1 group M global diversity included interclade viral recombinants. It is now appreciated that HIV-1 recombinants will be found in geographic areas such as Africa, South America, and Southeast Asia, where multiple HIV-1 subtypes coexist and may account for more than 10% of circulating HIV-1 strains. Molecularly, the genomes of these recombinant viruses resemble patchwork mosaics, with juxtaposed diverse HIV-1 subtype segments, reflecting the multiple crossover events contributing to their generation. Most HIV-1 recombinants have arisen in Africa and a majority contains segments originally derived from clade A viruses. In Thailand, for example, the composition of the predominant circulating strain consists of a clade A gag plus pol gene segment and a clade E env gene. Because the clade E env gene in That HIV-1 strains is closely related to the clade E env present in virus isolates from the Central African Republic, it is believed that the original recombination event occurred in Africa, with the subsequent introduction of a descendent virus into Thailand. Interestingly, no full-length HIV-1 subtype E isolate (i.e., with subtype E gag, pol, and env genes) has been reported to date.

The discovery that α and β chemokine receptors function as coreceptors for virus fusion and entry into susceptible $CD4^+$ cells has led to a revised classification scheme for HIV-1 (FIG. 3). Isolates can now be grouped on the basis of chemokine receptor utilization in fusion assays in which HIV-1 gp120 and $CD4^+$ coreceptor proteins are expressed in separate cells. As indicated in FIG. 3, HIV-1 isolates using the CXCR4 receptor (now designated X4 viruses) are usually T cell line (TCL)-tropic syncytium inducing (SI) strains, whereas those exclusively utilizing the CCR5 receptor (R5 viruses) are predominantly macrophage (M)-tropic and non-syncytium inducing (NSI). The dual-tropic R5/X4 strains, which may comprise the majority of patient isolates and exhibit a continuum of tropic phenotypes, are frequently SI.

Figure 4:
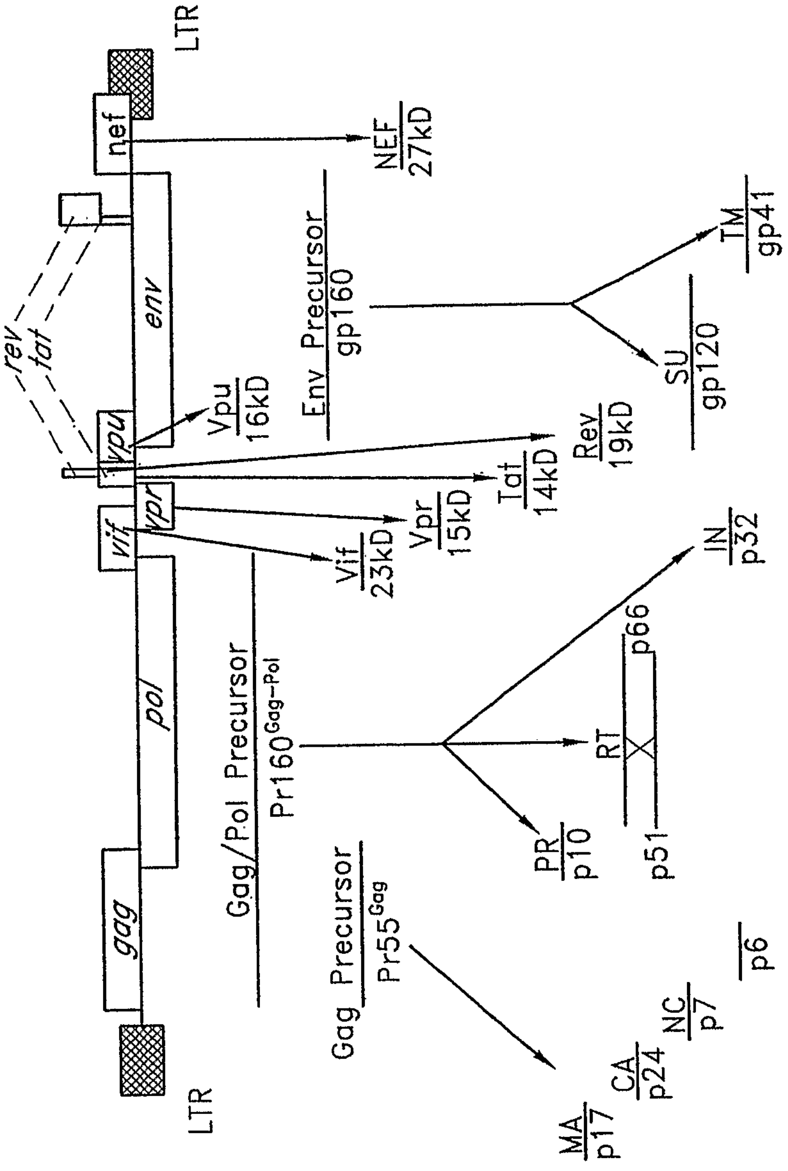
FIG. 4. HIV-encoded proteins. The location of the HIV genes, the sizes of primary translation products (in some cases polyproteins), and the processed mature viral proteins are indicated.

As is the case for all replication-competent retroviruses, the three primary HIV-1 translation products, all encoding structural proteins, are initially synthesized as polyprotein precursors, which are subsequently processed by viral or cellular proteases into mature particle-associated proteins (FIG. 4). The 55-kd Gag precursor $Pr55^{Gag}$ is cleaved into the matrix (MA), capsid (CA), nucleocapsid (NC), and p6 proteins. Autocatalysis of the 160-kd Gag-Pol polyprotein, $Pr160^{Gag-Pol}$, gives rise to the protease (PR), the heterodimeric reverse transcriptase (RT), and the integrase (IN) proteins, whereas proteolytic digestion by a cellular enzyme (s) converts the glycosylated 160-kd Env precursor gp160 to the gp120 surface (SU) and gp41 transmembrane (TM) cleavage products. The remaining six HIV-1-encoded proteins (Vif, Vpr, Tat, Rev, Vpu, and Nef) are the primary translation products of spliced mRNAs.

Gag

Figure 5:
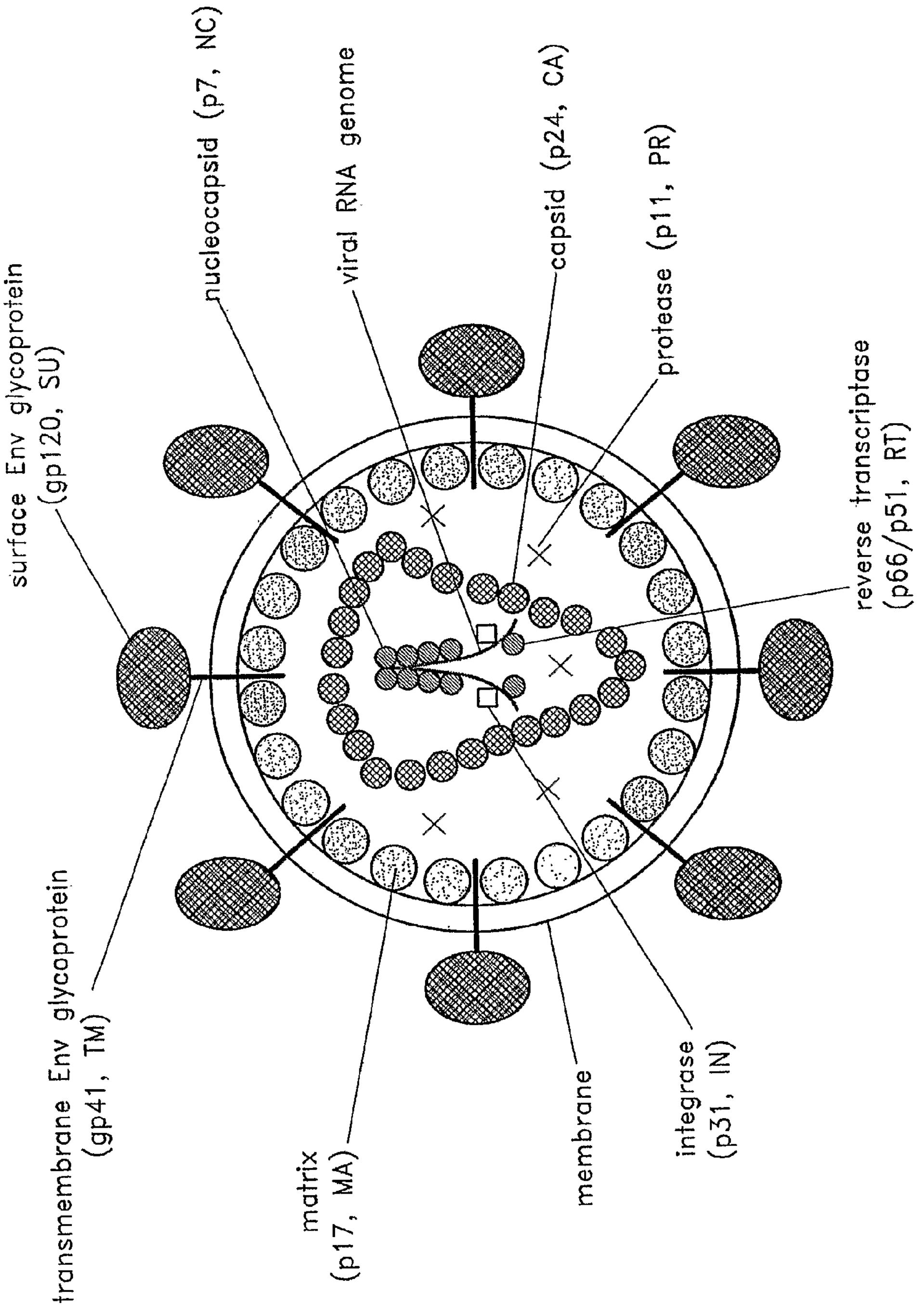
FIG. 5. Schematic representation of a mature HIV-1 virion.

The Gag proteins of HIV, like those of other retroviruses, are necessary and sufficient for the formation of noninfectious, virus-like particles. Retroviral Gag proteins are generally synthesized as polyprotein precursors; the HIV-1 Gag precursor has been named, based on its apparent molecular mass, $Pr55^{Gag}$. As noted previously, the mRNA for $Pr55^{Gag}$ is the unspliced 9.2-kb transcript (FIG. 4) that requires Rev for its expression in the cytoplasm. When the pol ORF is present, the viral protease (PR) cleaves $Pr55^{Gag}$ during or shortly after budding from the cell to generate the mature Gag proteins p17 (MA), p24 (CA), p7 (NC), and p6 (see FIG. 4). In the virion, MA is localized immediately inside the lipid bilayer of the viral envelope, CA forms the outer portion of the cone-shaped core structure in the center of the particle, and NC is present in the core in a ribonucleoprotein complex with the viral RNA genome (FIG. 5).

The HIV $Pr55^{Gag}$ precursor oligomerizes following its translation and is targeted to the plasma membrane, where particles of sufficient size and density to be visible by EM are assembled. Formation of virus-like particles by $Pr55^{Gag}$ is a self-assembly process, with critical Gag-Gag interactions taking place between multiple domains along the Gag precursor. The assembly of virus-like particles does not require the participation of genomic RNA (although the presence of nucleic acid appears to be essential), pol-encoded enzymes, or Env glycoproteins, but the production of infectious virions requires the encapsidation of the viral RNA genome and the incorporation of the Env glycoproteins and the Gag-Pol polyprotein precursor $Pr160^{Gag-Pol}$.

Pol

Downstream of gag lies the most highly conserved region of the HIV genome, the pol gene, which encodes three enzymes: PR, RT, and IN (see FIG. 4). RT and IN are required, respectively, for reverse transcription of the viral RNA genome to a double-stranded DNA copy, and for the integration of the viral DNA into the host cell chromosome. PR plays a critical role late in the life cycle by mediating the production of mature, infectious virions. The pol gene products are derived by enzymatic cleavage of a 160-kd Gag-Pol fusion protein, referred to as $Pr160^{Gag-Pol}$. This fusion protein is produced by ribosomal frame-shifting during translation of $Pr55^{Gag}$ (see FIG. 4). The frame-shifting mechanism for Gag-Pol expression, also utilized by many other retroviruses, ensures that the pol-derived proteins are expressed at a low level, approximately 5% to 10% that of Gag. Like $Pr55^{Gag}$, the N-terminus of $Pr160^{Gag-Pol}$ is myristylated and targeted to the plasma membrane.

Protease

Early pulse-chase studies performed with avian retroviruses clearly indicated that retroviral Gag proteins are initially synthesized as polyprotein precursors that are cleaved to generate smaller products. Subsequent studies demonstrated that the processing function is provided by a viral rather than a cellular enzyme, and that proteolytic digestion of the Gag and Gag-Pol precursors is essential for virus infectivity. Sequence analysis of retroviral PRs indicated that they are related to cellular "aspartic" proteases such as pepsin and renin. Like these cellular enzymes, retroviral PRs use two apposed Asp residues at the active site to coordinate a water molecule that catalyzes the hydrolysis of a peptide bond in the target protein. Unlike the cellular aspartic proteases, which function as pseudodimers (using two folds within the same molecule to generate the active site), retroviral PRs function as true dimers. X-ray crystallographic data from HIV-1 PR indicate that the two monomers are held together in part by a four-stranded antiparallel β-sheet derived from both N- and C-terminal ends of each monomer. The substrate-binding site is located within a cleft formed between the two monomers. Like their cellular homologs, the HIV PR dimer contains flexible "flaps" that overhang the binding site and may stabilize the substrate within the cleft; the active-site Asp residues lie in the center of the dimer. Interestingly, although some limited amino acid homology is observed surrounding active-site residues, the primary sequences of retroviral PRs are highly divergent, yet their structures are remarkably similar.

Reverse Transcriptase

By definition, retroviruses possess the ability to convert their single-stranded RNA genomes into double-stranded DNA during the early stages of the infection process. The enzyme that catalyzes this reaction is RT, in conjunction with its associated RNaseH activity. Retroviral RTs have three enzymatic activities: (a) RNA-directed DNA polymerization (for minus-strand DNA synthesis), (b) RNaseH activity (for the degradation of the tRNA primer and genomic RNA present in DNA-RNA hybrid intermediates), and (c) DNA-directed DNA polymerization (for second- or plus-strand DNA synthesis).

The mature HIV-1 RT holoenzyme is a heterodimer of 66 and 51 kd subunits. The 51-kd subunit (p51) is derived from the 66-kd (p66) subunit by proteolytic removal of the C-terminal 15-kd RNaseH domain of p66 by PR (see FIG. 4). The crystal structure of HIV-1 RT reveals a highly asymmetric folding in which the orientations of the p66 and p51 subunits differ substantially. The p66 subunit can be visualized as a right hand, with the polymerase active site within the palm, and a deep template-binding cleft formed by the palm, fingers, and thumb subdomains. The polymerase domain is linked to RNaseH by the connection subdomain. The active site, located in the palm, contains three critical Asp residues (110, 185, and 186) in close proximity, and two coordinated $Mg^{2+}$ ions. Mutation of these Asp residues abolishes RT polymerizing activity. The orientation of the three active-site Asp residues is similar to that observed in other DNA polymerases (e.g., the Klenow fragment of *E. coli* DNA polI). The p51 subunit appears to be rigid and does not form a polymerizing cleft; Asp 110, 185, and 186 of this subunit are buried within the molecule. Approximately 18 base pairs of the primer-template duplex lie in the nucleic acid binding cleft, stretching from the polymerase active site to the RNaseH domain.

In the RT-primer-template-dNTP structure, the presence of a dideoxynucleotide at the 3' end of the primer allows visualization of the catalytic complex trapped just prior to attack on the incoming dNTP. Comparison with previously obtained structures suggests a model whereby the fingers close in to trap the template and dNTP prior to nucleophilic attack of the 3'-OH of the primer on the incoming dNTP. After the addition of the incoming dNTP to the growing chain, it has been proposed that the fingers adopt a more open configuration, thereby releasing the pyrophosphate and enabling RT to bind the next dNTP. The structure of the HIV-1 RNaseH has also been determined by x-ray crystallography; this domain displays a global folding similar to that of *E. coli* RNaseH.

Integrase

A distinguishing feature of retrovirus replication is the insertion of a DNA copy of the viral genome into the host cell chromosome following reverse transcription. The integrated viral DNA (the provirus) serves as the template for the synthesis of viral RNAs and is maintained as part of the host cell genome for the lifetime of the infected cell. Retroviral mutants deficient in the ability to integrate generally fail to establish a productive infection.

The integration of viral DNA is catalyzed by integrase, a 32-kd protein generated by PR-mediated cleavage of the C-terminal portion of the HIV-1 Gag-Pol polyprotein (see FIG. 4).

Retroviral IN proteins are composed of three structurally and functionally distinct domains: an N-terminal, zinc-finger-containing domain, a core domain, and a relatively nonconserved C-terminal domain. Because of its low solubility, it has not yet been possible to crystallize the entire 288-amino-acid HIV-1 IN protein. However, the structure of all three domains has been solved independently by x-ray crystallography or NMR methods. The crystal structure of the core domain of the avian sarcoma virus IN has also been determined. The N-terminal domain (residues 1 to 55), whose structure was solved by NMR spectroscopy, is composed of four helices with a zinc coordinated by amino acids His-12, His-16, Cys-40, and Cys-43. The structure of the N-terminal domain is reminiscent of helical DNA binding proteins that contain a so-called helix-turn-helix motif, however, in the HIV-1 structure this motif contributes to dimer formation. Initially, poor solubility hampered efforts to solve the structure of the core domain. However, attempts at crystallography were successful when it was observed that a Phe-to-Lys change at IN residue 185 greatly increased solubility without disrupting in vitro catalytic activity. Each monomer of the HIV-1 IN core domain (IN residues 50 to 212) is composed of a five-stranded β-sheet flanked by helices; this structure bears striking resemblance to other polynucleotidyl transferases including RNaseH and the bacteriophage MuA transposase. Three highly conserved residues are found in analogous positions in other polynucleotidyl transferases; in HIV-1 IN these are Asp-64, Asp-116 and Glu-152, the so-called D,D-35-E motif. Mutations at these positions block HIV IN function both in vivo and in vitro. The close proximity of these three amino acids in the crystal structure of both avian sarcoma virus and HIV-1 core domains supports the hypothesis that these residues play a central role in catalysis of the polynucleotidyl transfer reaction that is at the heart of the integration process. The C-terminal domain, whose structure has been solved by NMR methods, adopts a five-stranded β-barrel folding topology reminiscent of a Src homology 3 (SH3) domain. Recently, the x-ray structures of SIV and Rous sarcoma virus IN protein fragments encompassing both the core and C-terminal domains have been solved.

Env

The HIV Env glycoproteins play a major role in the virus life cycle. They contain the determinants that interact with the CD4 receptor and coreceptor, and they catalyze the fusion reaction between the lipid bilayer of the viral envelope and the host cell plasma membrane. In addition, the HIV Env glycoproteins contain epitopes that elicit immune responses that are important from both diagnostic and vaccine development perspectives.

Figure 6:
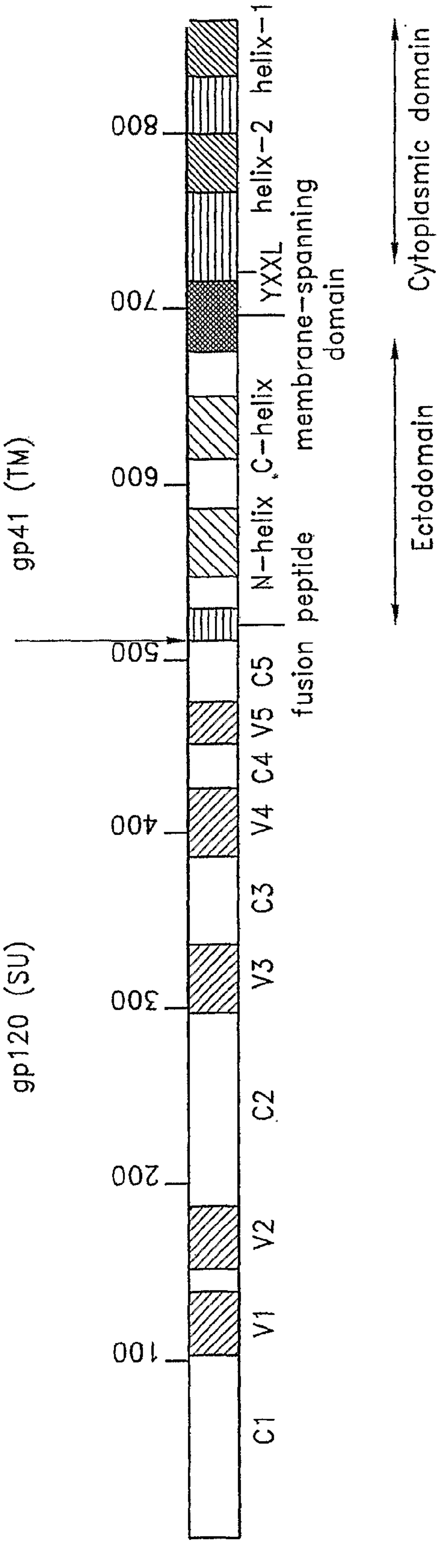
FIG. 6. Linear representation of the HIV-1 Env glycoprotein. The arrow indicates the site of gp160 cleavage to gp120 and gp41. In gp120, cross-hatched areas represent variable domains ($V_1$ to $V_5$) and open boxes depict conserved sequences ($C_1$ to $C_5$). In the gp41 ectodomain, several domains are indicated: the N-terminal fusion peptide, and the two ectodomain helices (N- and C-helix). The membrane-spanning domain is represented by a black box. In the gp41 cytoplasmic domain, the Tyr-X-X-Leu (YXXL) endocytosis motif (SEQ ID NO: 13) and two predicted helical domains (helix-1 and -2) are shown. Amino acid numbers are indicated.

The HIV Env glycoprotein is synthesized from the singly spliced 4.3-kb Vpu/Env bicistronic mRNA (see FIG. 4); translation occurs on ribosomes associated with the rough endoplasmic reticulum (ER). The 160-kd polyprotein precursor (gp160) is an integral membrane protein that is anchored to cell membranes by a hydrophobic stop-transfer signal in the domain destined to be the mature TM Env glycoprotein, gp41 (FIG. 6). The gp160 is cotranslationally glycosylated, forms disulfide bonds, and undergoes oligomerization in the ER. The predominant oligomeric form appears to be a trimer, although dimers and tetramers are also observed. The gp160 is transported to the Golgi, where, like other retroviral envelope precursor proteins, it is proteolytically cleaved by cellular enzymes to the mature SU glycoprotein gp120 and TM glycoprotein gp41 (see FIG. 6). The cellular enzyme responsible for cleavage of retroviral Env precursors following a highly conserved Lys/Arg-X-Lys/Arg-Arg motif is furin or a furin-like protease, although other enzymes may also catalyze gp160 processing. Cleavage of gp160 is required for Env-induced fusion activity and virus infectivity. Subsequent to gp160 cleavage, gp120 and gp41 form a noncovalent association that is critical for transport of the Env complex from the Golgi to the cell surface. The gp120-gp41 interaction is fairly weak, and a substantial amount of gp120 is shed from the surface of Env-expressing cells.

The HIV Env glycoprotein complex, in particular the SU (gp120) domain, is very heavily glycosylated; approximately half the molecular mass of gp160 is composed of oligosaccharide side chains. During transport of Env from its site of synthesis in the ER to the plasma membrane, many of the side chains are modified by the addition of complex sugars. The numerous oligosaccharide side chains form what could be imagined as a sugar cloud obscuring much of gp120 from host immune recognition. As shown in FIG. 6, gp120 contains interspersed conserved ($C_1$ to $C_5$) and variable ($V_1$ to $V_5$) domains. The Cys residues present in the gp120s of different isolates are highly conserved and form disulfide bonds that link the first four variable regions in large loops.

A primary function of viral Env glycoproteins is to promote a membrane fusion reaction between the lipid bilayers of the viral envelope and host cell membranes. This membrane fusion event enables the viral core to gain entry into the host cell cytoplasm. A number of regions in both gp120 and gp41 have been implicated, directly or indirectly, in Env-mediated membrane fusion. Studies of the HA2 hemagglutinin protein of the orthomyxoviruses and the F protein of the paramyxoviruses indicated that a highly hydrophobic domain at the N-terminus of these proteins, referred to as the fusion peptide, plays a critical role in membrane fusion. Mutational analyses demonstrated that an analogous domain was located at the N-terminus of the HIV-1, HIV-2, and SIV TM glycoproteins (see FIG. 6). Nonhydrophobic substitutions within this region of gp41 greatly reduced or blocked syncytium formation and resulted in the production of noninfectious progeny virions.

C-terminal to the gp41 fusion peptide are two amphipathic helical domains (see FIG. 6) which play a central role in membrane fusion. Mutations in the N-terminal helix (referred to as the N-helix), which contains a Leu zipper-like heptad repeat motif, impair infectivity and membrane fusion activity, and peptides derived from these sequences exhibit potent antiviral activity in culture. The structure of the ectodomain of HIV-1 and SIV gp41, the two helical motifs in particular, has been the focus of structural analyses in recent years. Structures were determined by x-ray crystallography or NMR spectroscopy either for fusion proteins containing the helical domains, a mixture of peptides derived from the N- and C-helices, or in the case of the SIV structure, the intact gp41 ectodomain sequence from residue 27 to 149. These studies obtained fundamentally similar trimeric structures, in which the two helical domains pack in an antiparallel fashion to generate a six-helix bundle. The N-helices form a coiled-coil in the center of the bundle, with the C-helices packing into hydrophobic grooves on the outside.

In the steps leading to membrane fusion CD4 binding induces conformation changes in Env that facilitate coreceptor binding. Following the formation of a ternary gp120/CD4/coreceptor complex, gp41 adopts a hypothetical conformation that allows the fusion peptide to insert into the target lipid bilayer. The formation of the gp41 six-helix bundle (which involves antiparallel interactions between the gp41 N- and C-helices) brings the viral and cellular membranes together and membrane fusion takes place.

Use of Recombinant MVA Virus to Boost CD+8 Cell Immune Response

The present invention relates to generation of a $CD8^+$ T cell immune response against an antigen and also eliciting an antibody response. More particularly, the present invention relates to "prime and boost" immunization regimes in which the immune response induced by administration of a priming composition is boosted by administration of a boosting composition. The present invention is based on inventors' experimental demonstration that effective boosting can be achieved using modified vaccinia Ankara (MVA) vectors, following priming with any of a variety of different types of priming compositions including recombinant MVA itself.

A major protective component of the immune response against a number of pathogens is mediated by T lymphocytes of the $CD8^+$ type, also known as cytotoxic T lymphocytes (CTL). An important function of $CD8^+$ cells is secretion of gamma interferon (IFNγ), and this provides a measure of $CD8^+$ T cell immune response. A second component of the immune response is antibody directed to the proteins of the pathogen.

The present invention employs MVA which, as the experiments described below show, has been found to be an effective means for providing a boost to a $CD8^+$ T cell immune response primed to antigen using any of a variety of different priming compositions and also eliciting an antibody response.

Remarkably, the experimental work described below demonstrates that use of embodiments of the present invention allows for recombinant MVA virus expressing an HIV antigen to boost a $CD8^+$ T cell immune response primed by a DNA vaccine and also eliciting an antibody response. The MVA was found to induce a $CD8^+$ T cell response after intramuscular immunization.

Based on previous work (Amara et al 2001 *Science* 292:69-74), it is predicted that non-human primates immunized with plasmid DNA and boosted with the MVA would effectively protect against intramucosal challenge with live virus. Advantageously, the inventors contemplate that a vaccination regime using intradermal, intramuscular or mucosal immunization for both prime and boost can be employed, constituting a general immunization regime suitable for inducing $CD8^+$ T cells and also eliciting an antibody response, e.g. in humans.

The present invention in various aspects and embodiments employs an MVA vector encoding an HIV antigen for boosting a $CD8^+$ T cell immune response to the antigen primed by previous administration of nucleic acid encoding the antigen and also eliciting an antibody response.

A general aspect of the present invention provides for the use of an MVA vector for boosting a $CD8^+$ T cell immune response to an HIV antigen and also eliciting an antibody response.

One aspect of the present invention provides a method of boosting a $CD8^+$ T cell immune response to an HIV antigen in an individual, and also eliciting an antibody response, the method including provision in the individual of an MVA vector including nucleic acid encoding the antigen operably linked to regulatory sequences for production of antigen in the individual by expression from the nucleic acid, whereby a $CD8^+$ T cell immune response to the antigen previously primed in the individual is boosted.

An immune response to an HIV antigen may be primed by immunization with plasmid DNA or by infection with an infectious agent.

A further aspect of the invention provides a method of inducing a $CD8^+$ T cell immune response to an HIV antigen in an individual, and also eliciting an antibody response, the method comprising administering to the individual a priming composition comprising nucleic acid encoding the antigen and then administering a boosting composition which comprises an MVA vector including nucleic acid encoding the antigen operably linked to regulatory sequences for production of antigen in the individual by expression from the nucleic acid.

A further aspect provides for use of an MVA vector, as disclosed, in the manufacture of a medicament for administration to a mammal to boost a $CD8^+$ T cell immune response to an HIV antigen, and also eliciting an antibody response. Such a medicament is generally for administration following prior administration of a priming composition comprising nucleic acid encoding the antigen.

The priming composition may comprise any viral vector, such as a vaccinia virus vector such as a replication-deficient strain such as modified vaccinia Ankara (MVA) or NYVAC (Tartaglia et al. 1992 *Virology* 118:217-232), an avipox vector such as fowlpox or canarypox, e.g. the strain known as ALVAC (Paoletti et al. 1994 *Dev Biol Stand* 82:65-69), or an adenovirus vector or a vesicular stomatitis virus vector or an alphavirus vector.

The priming composition may comprise DNA encoding the antigen, such DNA preferably being in the form of a circular plasmid that is not capable of replicating in mammalian cells. Any selectable marker should not be resistance to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present invention, administration of a priming composition is followed by boosting with a boosting composition, or first and second boosting compositions, the first and second boosting compositions being the same or different from one another. Still further boosting compositions may be employed without departing from the present invention. In one embodiment, a triple immunization regime employs DNA, then adenovirus as a first boosting composition, then MVA as a second boosting composition, optionally followed by a further (third) boosting composition or subsequent boosting administration of one or other or both of the same or different vectors. Another option is DNA then MVA then adenovirus, optionally followed by subsequent boosting administration of one or other or both of the same or different vectors.

The antigen to be encoded in respective priming and boosting compositions (however many boosting compositions are employed) need not be identical, but should share at least one $CD8^+$ T cell epitope. The antigen may correspond to a complete antigen, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types. Priming and boosting may be administered intradermally, intramuscularly or mucosally.

An HIV antigen of the invention to be encoded by a recombinant MVA virus includes polypeptides having immunogenic activity elicited by an amino acid sequence of an HIV Env, Gag, Pol, Vif, Vpr, Tat, Rev, Vpu, or Nef amino acid sequence as at least one $CD8^+$ T cell epitope. This amino acid sequence substantially corresponds to at least one 10-900 amino acid fragment and/or consensus sequence of a known HIV Env or Pol; or at least one 10-450 amino acid fragment and/or consensus sequence of a known HIV Gag; or at least one 10-100 amino acid fragment and/or consensus sequence of a known HIV Vif, Vpr, Tat, Rev, Vpu, or Nef.

Although a full length Env precursor sequence is presented for use in the present invention, Env is optionally deleted of subsequences. For example, regions of the gp120 surface and gp41 transmembrane cleavage products can be deleted.

Although a full length Gag precursor sequence is presented for use in the present invention, Gag is optionally deleted of subsequences. For example, regions of the matrix protein (p17), regions of the capsid protein (p24), regions of the nucleocapsid protein (p7), and regions of p6 (the C-terminal peptide of the Gag polyprotein) can be deleted.

Although a full length Pol precursor sequence is presented for use in the present invention, Pol is optionally deleted of subsequences. For example, regions of the protease protein (p10), regions of the reverse transcriptase protein (p66/p51), and regions of the integrase protein (p32) can be deleted.

Such an HIV Env, Gag, or Pol can have overall identity of at least 50% to a known Env, Gag, or Pol protein amino acid sequence, such as 50-99% identity, or any range or value therein, while eliciting an immunogenic response against at least one strain of an HIV.

Percent identify can be determined, for example, by comparing sequence information using the GAP computer program, version 6.0, available from the University of Wisconsin Genetics Computer Group (UWGCG). The GAP program utilizes the alignment method of Needleman and Wunsch (*J Mol Biol* 1970 48:443), as revised by Smith and Waterman (*Adv Appl Math* 1981 2:482). Briefly, the GAP program defines identity as the number of aligned symbols (i.e., nucleotides or amino acids) which are identical, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (*Nucl Acids Res* 1986 14:6745), as described by Schwartz and Dayhoff (eds., Atlas of Protein Sequence and Structure, National Biomedical Research Foundation, Washington, D.C. 1979, pp. 353-358); (2) a penalty of 3.0 for each gap and an additional 0.10 penalty for each symbol in each gap; and (3) no penalty for end gaps.

In a preferred embodiment, an Env of the present invention is a variant form of at least one HIV envelope protein. Preferably, the Env is composed of gp120 and the membrane-spanning and ectodomain of gp41 but lacks part or all of the cytoplasmic domain of gp41.

Known HIV sequences are readily available from commercial and institutional HIV sequence databases, such as GENBANK, or as published compilations, such as Myers et al. eds., Human Retroviruses and AIDS, A Compilation and Analysis of Nucleic Acid and Amino Acid Sequences, Vol. I and II, Theoretical Biology and Biophysics, Los Alamos, N. Mex. (1993).

Substitutions or insertions of an HIV Env, Gag, or Pol to obtain an additional HIV Env, Gag, or Pol, encoded by a nucleic acid for use in a recombinant MVA virus of the present invention, can include substitutions or insertions of at least one amino acid residue (e.g., 1-25 amino acids). Alternatively, at least one amino acid (e.g., 1-25 amino acids) can be deleted from an HIV Env, Gag, or Pol sequence. Preferably, such substitutions, insertions or deletions are identified based on safety features, expression levels, illmunogenicity and compatibility with high replication rates of MVA.

Amino acid sequence variations in an HIV Env, Gag, or Pol of the present invention can be prepared e.g., by mutations in the DNA. Such HIV Env, Gag, or Pol include, for example, deletions, insertions or substitutions of nucleotides coding for different amino acid residues within the amino acid sequence. Obviously, mutations that will be made in nucleic acid encoding an HIV Env, Gag, or Pol must not place the sequence out of reading frame and preferably will not create complementary domains that could produce secondary mRNA structures.

HIV Env, Gag, or Pol-encoding nucleic acid of the present invention can also be prepared by amplification or site-directed mutagenesis of nucleotides in DNA or RNA encoding an HIV Env, Gag, or Pol and thereafter synthesizing or reverse transcribing the encoding DNA to produce DNA or RNA encoding an HIV Env, Gag, or Pol, based on the teaching and guidance presented herein.

Recombinant MVA viruses expressing HIV Env, Gag, or Pol of the present invention, include a finite set of HIV Env, Gag, or Pol-encoding sequences as substitution nucleotides that can be routinely obtained by one of ordinary skill in the art, without undue experimentation, based on the teachings and guidance presented herein. For a detailed description of protein chemistry and structure, see Schulz, G. E. et al., 1978 *Principles of Protein Structure*, Springer-Verlag, New York, N.Y., and Creighton, T. E., 1983 *Proteins: Structure and Molecular Properties*, W. H. Freeman & Co., San Francisco, Calif. For a presentation of nucleotide sequence substitutions, such as codon preferences, see Ausubel et al. eds. *Current Protocols in Molecular Biology*, Greene Publishing Assoc., New York, N.Y. 1994 at §§A.1.1-A.1.24, and Sambrook, J. et al. 1989 *Molecular Cloning: A Laboratory Manual*, Second Edition, Cold Spring Harbor Laboratory Press, Cold. Spring Harbor, N.Y. at Appendices C and D.

Thus, one of ordinary skill in the art, given the teachings and guidance presented herein, will now how to substitute other amino acid residues in other positions of an HIV env, gag, or pol DNA or RNA to obtain alternative HIV Env, Gag, or Pol, including substitutional, deletional or insertional variants.

Within the MVA vector, regulatory sequences for expression of the encoded antigen will include a natural, modified or synthetic poxvirus promoter. By "promoter" is meant a sequence of nucleotides from which transcription may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, marker genes and other sequences may be included as appropriate, in accordance with the knowledge and practice of the ordinary person skilled in the art: see, for example, Moss, B. (2001). Poxyiridae: the viruses and their replication. In Fields Virology, D. M. Knipe, and P. M. Howley, eds. (Philadelphia, Lippincott Williams & Wilkins), pp. 2849-2883. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology,* 1998 Ausubel et al. eds., John Wiley & Sons.

Promoters for use in aspects and embodiments of the present invention must be compatible with poxvirus expression systems and include natural, modified and synthetic sequences.

Either or both of the priming and boosting compositions may include an adjuvant, such as granulocyte macrophage-colony stimulating factor (GM-CSF) or encoding nucleic acid therefor.

Administration of the boosting composition is generally about 1 to 10 months after administration of the priming composition, preferrably about 1 to 6 months, preferably about 1 to 4 months, preferably about 1 to 3 months.

Preferably, administration of priming composition, boosting composition, or both priming and boosting compositions, is intradermal, intramuscular or mucosal immunization.

Administration of MVA vaccines may be achieved by using a needle to inject a suspension of the virus. An alternative is the use of a needleless injection device to administer a virus suspension (using, e.g., Biojector™ needleless injector) or a resuspended freeze-dried powder containing the vaccine, providing for manufacturing individually prepared doses that do not need cold storage. This would be a great advantage for a vaccine that is needed in rural areas of Africa.

MVA is a virus with an excellent safety record in human immunizations. The generation of recombinant viruses can be accomplished simply, and they can be manufactured reproducibly in large quantities. Intradermal, intramuscular or mucosal administration of recombinant MVA virus is therefore highly suitable for prophylactic or therapeutic vaccination of humans against AIDS which can be controlled by a $CD8^+$ T cell response.

The individual may have AIDS such that delivery of the antigen and generation of a $CD8^+$ T cell immune response to the antigen is of benefit or has a therapeutically beneficial effect.

Most likely, administration will have prophylactic aim to generate an immune response against HIV or AIDS before infection or development of symptoms.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. intravenous, cutaneous or subcutaneous, nasal, intramuscular, intraperitoneal routes.

As noted, administration is preferably intradermal, intramuscular or mucosal.

Physiological saline solution, dextrose or other saccharide solution or glycols such as ethylene glycol, propylene glycol or polyethylene glycol may be included.

For intravenous, cutaneous, subcutaneous, intramuscular or mucosal injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included as required.

A slow-release formulation may be employed.

Following production of MVA particles and optional formulation of such particles into compositions, the particles may be administered to an individual, particularly human or other primate. Administration may be to another mammal, e.g. rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences,* 16th edition, 1980, Osol, A. (ed.).

In one preferred regimen, DNA is administered at a dose of 250 μg to 2.5 mg/injection, followed by MVA at a dose of $10^6$ to $10^9$ infectious virus particles/injection.

A composition may be administered alone or in combination with other treatments, either simultaneously or sequentially dependent upon the condition to be treated.

Delivery to a nonhuman mammal need not be for a therapeutic purpose, but may be for use in an experimental context, for instance in investigation of mechanisms of immune responses to an antigen of interest, e.g. protection against HIV or AIDS.

Further aspects and embodiments of the present invention will be apparent to those of ordinary skill in the art, in view of the above disclosure and following experimental exemplification, included by way of illustration and not limitation, and with reference to the attached figures.

| HIV Strain/Clade | Region | Gag | Env | Recombinant virus |
|---|---|---|---|---|
| Clade A/G 928 | From Ivory Coast, for use in West Africa | 93% identical to consensus A/G Gag | 81% identical to consensus A/G Env | Recombinant MVA 65A/G virus expresses Env Gag Pol |
| Clade B ADA env/ HXB2/BH10gp | From USA | 96% identical to consensus B Gag | 92% identical to consensus B Env | Recombinant MVA 62B virus expresses HIV Env Gag Pol |
| Clade C IN3 | From India | 95% identical to consensus C Gag | 89% identical to consensus C Env | Recombinant MVA 71C virus expresses HIV Env Gag Pol |

EXAMPLE 1

Construction of Plasmid Shuttle Vectors LAS-1 and LAS-2 Used to Make MVA/HIV Recombinants 1. Plasmid Shuttle Vector LAS-1—

This plasmid shuttle vector, which inserts into deletion site III of the MVA genome, was constructed in the following steps: The P11 vaccinia virus promoter and the *Escherichia coli* glucuronidase (GUS) gene were removed from pLW-51 (Wyatt, L. S. et al. 2004 *AIDS Res. Human Retroviruses* 20:645-653) by AscI and SacI digestion. The P11 vaccinia promoter and green fluorescent protein (GFP) with AscI and SacI ends, obtained by PCR amplification from pLW-44 (Bisht, H. et al. 2004 *PNAS USA* 101:6641-6646), were ligated into the vector making pLW-51GFP. The psynII promoter was removed from pLW-51GFP by XhoI and NotI digestion, blunted, and religated to make LAS-1.

2. Plasmid Shuttle Vector LAS-2—

This plasmid shuttle vector, which inserts into deletion site II of the MVA genome, was constructed in the following manner: pLW-37 was made by annealing 2 oligos comprising complementary strands of the m115 promoter (Wyatt, L. S. et al. 1996 *Vaccine* 14:1451-58) with HincII site at the beginning and SmaI end and inserting this into the SmaI site of pLW-16 (Wyatt, L. S. et al. 1999 *Vaccine* 18:392-397). The last 217 bases of MVA flank 2 were duplicated with KpnI, AscI, and SacI sites on the end of the inside oligo and KpnI site on the end of the outside oligo, and inserted into the KpnI site of pLW-37. This plasmid, designated pLW-37a, was digested with AscI and SacI, and P11 vaccinia promoter and green fluorescent protein (GFP) with AscI and SacI ends (obtained by PCR amplification of P11 promoter and GFP from pLW-44 as described above) was inserted into it. The resulting plasmid was designated pLAS-2.

The plasmid transfer vector pLW-51 was constructed as follows. The mH5 promoter (Wyatt et al. 1996 Vaccine 14:1451-1458) was inserted into plasmid pG01 (Sutter and Moss. 1992 *PNAS USA* 89:10847-10851), which contains 926 and 530 bp of DNA that flank deletion III (del III). Gag-pol sequences from HIV clade B (strain BH10) DNA in plasmid GA2/JS2 (GenBank accession #AF42688) (Smith et al., 2004 *AIDS Res Human Retroviruses* 20:654-665) were amplified using the polymerase chain reaction (PCR) and inserted into the TA cloning plasmid pCR2.1 (Invitrogen Corp., Carlsbad, Calif.). The first 1872 nucleotides of the HIV strain BH10 gag-pol open reading frame (ORF) were replaced with the corresponding portion of the HXB2 gag ORE to enhance virus-like particle (VLP) formation. This chimeric gag-pol ORE was inserted into the modified pG01 plasmid after the mH5 promoter. The last 280 bp of the left MVA flank was duplicated and the P11 vaccinia virus promoter and the *Escherichia coli* glucuronidase (GUS) gene were inserted between the two direct repeats in order to implement a transient markerstabilization recombinant virus isolation protocol (Wyatt et al. 2004 *AIDS Res. Human Retrovir.* 20:645-653).

Plasmid pG01

Plasmids. Sequences of MVA DNA flanking the site of a 3500-bp deletion in the HindIII A fragment of the MVA genome were amplified by PCR and cloned into pGEM 4Z (Promega). The primers for the left 900-bp DNA flank were 5'-CAGCAGGAATTCGTTGGTGGTCGCCATGGATG-GTGT-3' (SEQ ID NO: 14) and 5'-GGGGGGGGTAC-CTACCAGCCACCGAAAGAG-3' (SEQ ID NO: 15) (sites for restriction enzymes EcoRI and Kpn I are underlined). The primers for the right 600-bp DNA flank were 5'-GGGGGGCTGCAGTTTGGAAAGTTT-TATAGGGGGGGGCTGCAGTTTGGAAAGTT TTATAGG-3' (SEQ ID NO: 16) and 5'-GGGGGGAAGCT-TAACTAGTTTCTGGTG-3' (SEQ ID NO: 17) (sites for the restriction enzymes Pst I and HindIII are underlined). Between these flanks of MVA DNA, the *Escherichia coli* lacZ gene under control of the vaccinia virus late promoter P1 and the *E. coli* gpt gene under control of the vaccinia virus early/late promoter P7.5 were cloned (Sutter and Moss 1992 *PNAS USA* 89:10847-10851).

II. pLW44 pLW44 contains a gene encoding enhanced GFP regulated by the vaccinia virus P11 late promoter.

III. pLW-16

A new plasmid transfer vector, pLW-17, was constructed to allow insertion into deletion II located on the left side of the MVA genome (H. Meyer, et al. 1991 *J. Gen. Virol.* 72:1031-1038) as follows. Flank 1 was prepared by PCR using primers beginning at nucleotide 52 preceding the left side of deletion site II, cloned into a T-A cloning vector, digested with SphI, and cloned into the SphI site of pGEM-4Z (Promega, Madison, Wis.). Flank 2 was prepared by PCR using primers containing EcoRI and KpnI compatible ends from the right side of deletion II and cloned into EcoRI and KpnI sites of pGEM-4Z. This plasmid containing the two flanking regions of deletion site II was designated pLW-16. The modified H5 promoter was excised from pLW-9 by digestion with SmaI and PstI and cloned into SmaI and PstI sites of pLW-16, resulting in the new plasmid transfer vector, pLW-17. The F coding sequence of RSV-A2 was excised from a plasmid kindly provided by P. Collins and blunt ligated into the SmaI site of pLW-17 (Wyatt, L. S. et al. 1999 *Vaccine* 18:392-397).

EXAMPLE 2

MVA Recombinants Expressing Clade A Env, Gag, and Pol

MVA 65A/G Construction and Characterization

This example describes the construction of a modified vaccinia virus Ankara (MVA) recombinant virus, MVA 65A/G, expressing clade A/G HIV strain 928 Env and Gag Pol. The salient features of this recombinant virus are:

1) A transient screening marker of green fluorescent protein (GFP) was used in construction of MVA 65A/G, so that the GFP is eliminated in the final virus product.

2) The A/G env gene is inserted into del II of MVA genome and the A/G gag pol is inserted in del III.

3) Both env and gag pol of MVA 65A/G are controlled by vaccinia PmH5 promoter.

4) The MVA virus used to make the recombinant MVA 65A/G is MVA 1974/NIH Clone 1.

Plasmid Transfer Vectors

Figure 7:
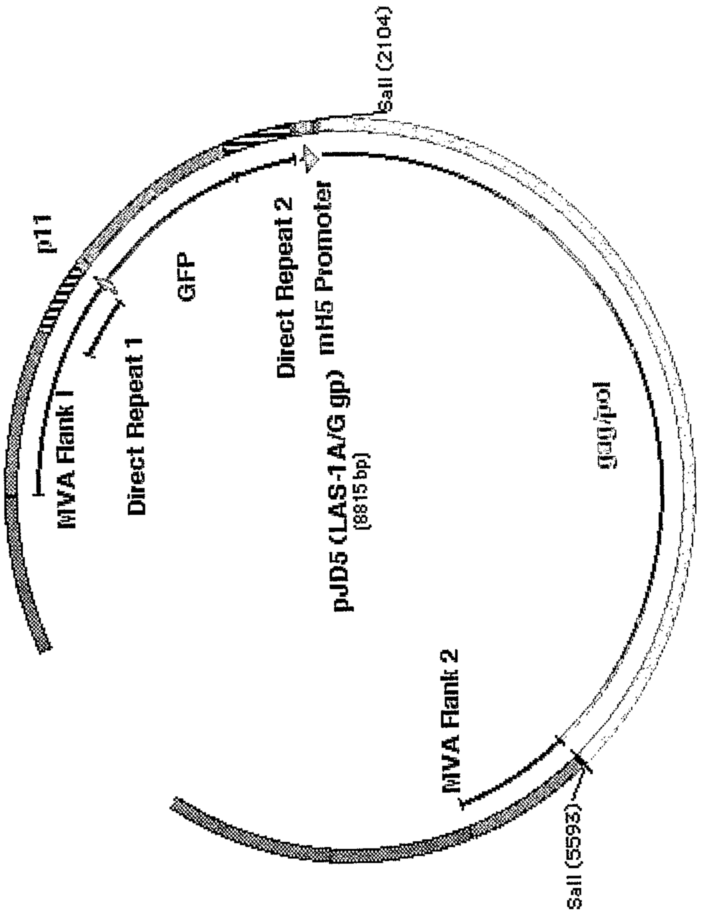
FIG. 7. pJD-5 transfer vector.

The plasmid transfer vectors, pJD5 and pJD6 (FIG. 7 and FIG. 8 respectively), were used to make single recombinant MVAs by homologous recombination. Each of these plasmids carry the transient GFP marker, and were constructed as follows:

1. Gag/pol gene sequence of HIV A/G 928 (from pGA2/928/928+3RT) containing three mutations to inactivate reverse transcriptase activity (corresponding to that given for Clade B recombinant) with the integrase removed was cloned into pCR2.1 using FailSafe PCR kit. The gag/pol gene was cloned into MVA deletion III transfer vector pLAS-1 (containing transient screening marker GFP flanked by two direct repeats to eliminate GFP in the final virus) via SalI restriction endonuclease site, and gene expression was under control of the early/late modified H5 promotor. Sequences of the HIV A/G 928 gag/pol gene was confirmed by DNA sequencing, and this construct was designated pJD5 gag pol (FIG. 7).

Figure 8:
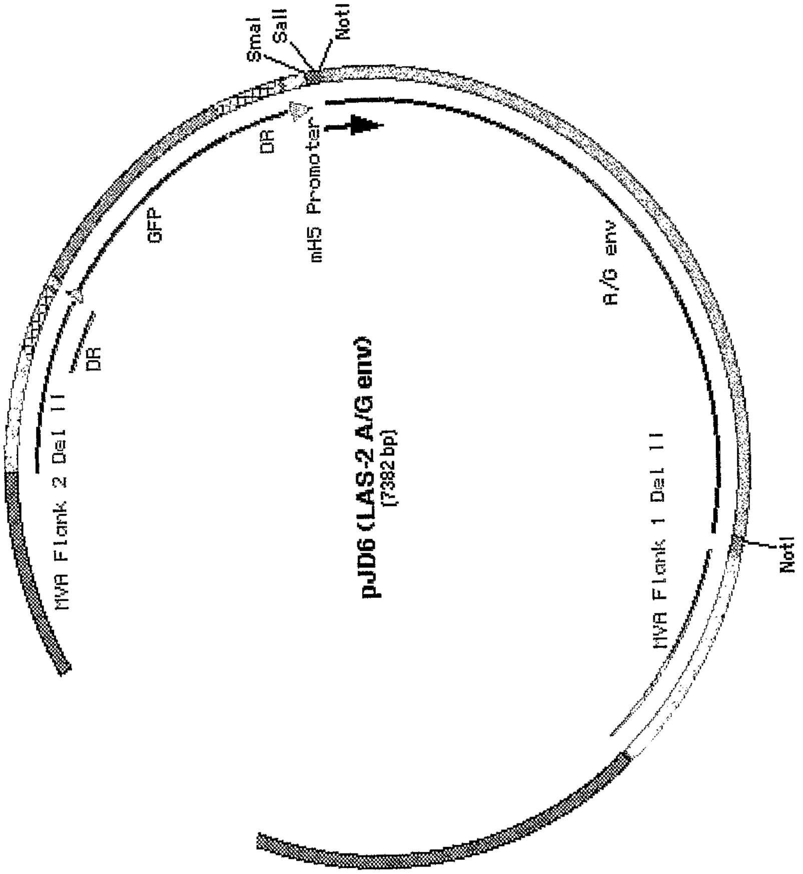
FIG. 8. pJD-6 transfer vector.

2. Env gene sequence of HIV A/G 928 (removed from pGA1/928/928 from Harriet Robinson) was truncated via PCR removal of 114 amino acids in the cytoplasmic tail of gp41 and cloned into pCR2.1. Silent mutations to eliminate 2 early poxvirus termination 5TNT signals were made (QuikChange Kit, Stratagene). The modified, truncated env gene was cloned into MVA deletion II transfer vector pLAS-2 (containing transient screening marker GFP flanked by two direct repeats to eliminate GFP in the final virus), with gene expression under control of the early/late modified H5 promotor. Sequence of the HIV A/G 928 env gene was confirmed by DNA sequencing, and this construct was designated pJD6 (FIG. 8).

Single Recombinant MVA Construction

1. MVA 1974/NIH Clone 1 virus, which was derived from an MVA received from Anton Mayr (Munich, Germany) at passage 572 from Feb. 22, 1974 by terminally diluting 3 times at the National Institutes of Health, was used for recombination.

2. Secondary CEF made from 10 day old SPAFAS fertile chicken eggs (distributed by B&E Eggs, Stevens, Pa.) in six-well culture plates were infected at an MOI of 0.05 of MVA and transfected with approximately 1.5 μg of JD5 or JD6 (FIG. 9). These two virus constructions were carried in like manner as described below, but independently.

3. Following a two day incubation at 37° C., the viruses were harvested, frozen and thawed 3×, and plated out on CEF.

4. At 3 days post-infection, those foci of infections that expressed GFP (indicating that recombination had occurred between the plasmid and the infecting virus) were picked and replated on CEF. Again, those foci that expressed GFP were picked. This process was repeated once more.

5. These 3× plaque-purified GFP-expressing foci were plated out in duplicate CEF plates and two plates were analyzed for GFP fluorescence and Gag or Env expression with T24 monoclonal antibody (envelope expression) or mAb 3537 (183-H12-5C, NIH AIDS Research and Reference Reagent Program) specific for Gag. Individual foci were picked from the duplicate replicate plate of those samples with little or no GFP fluorescence as well as mostly Gag or Env staining foci.

6. These foci were again plated out in duplicate, and analyzed the same way 1-2 additional times. The resulting recombinant viruses derived expressed either Gag Pol (vJD5gag/pol) or Env (vJD6env) proteins but had deleted the GFP gene by recombination of the double repeats.

Double Recombinant MVA Construction

1. To make the double MVA recombinant, MVA 65A/G, the two single recombinant MVA viruses, vJD5gag pol and vJD6 env, expressing Gag Pol and Env respectively, were used to infect CEF cells together at a MOI of 5, grown at 37 C for 2 days and harvested (FIG. 9).

2. Duplicate plates of the harvest were infected at different dilutions, and one plate was fixed and stained with T24 mAb and number of foci of infected cells that had rounded up CPE (characteristic of Gag Pol recombinants) were scored in order to assure there were double recombinants in the population. Then, foci with the rounded up morphology were picked from the unstained duplicate plate.

3. These foci were plated out at various dilutions in triplicate and immunostained for Env expression (T24 mAb) and Gag expression (3537 mAb). Those foci that stained for both Env and Gag expression were plaque purified 5 additional times.

4. The virus was expanded in CEF cells and a LVD Seed stock of MVA/HIV 65A/G 5.5×$10^8$ pfu/ml was produced. *Mycoplasma* testing by ATCC was negative. Sterility testing by BioReliance was negative. DNA sequencing confirmed both the env and the gag pol ORFs, as well as the deletion of the GFP reporter gene.

Characterization of MVA Recombinant Virus, MVA 65A/G

Figure 10:
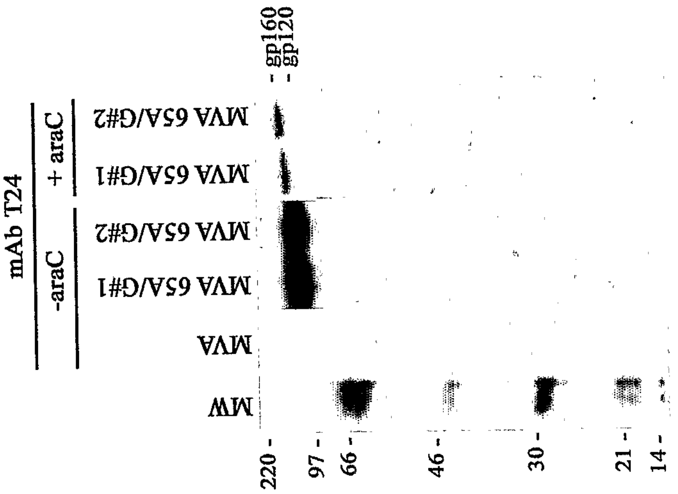
FIG. 10. MVA 65A/G expression of HIV Env.
Figure 11:
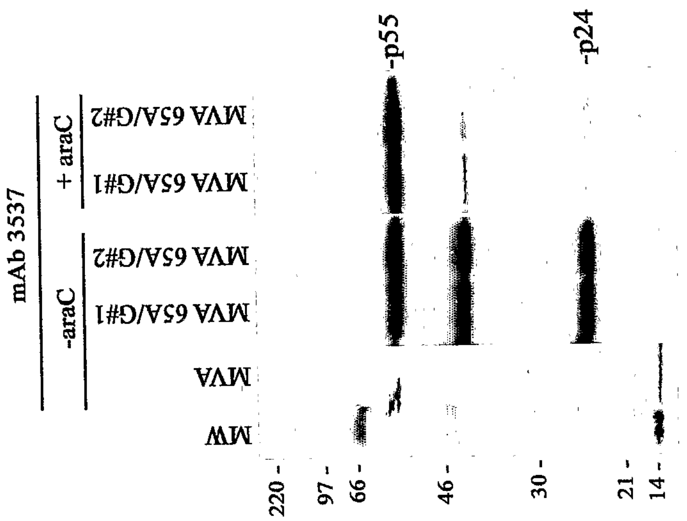
FIG. 11. MVA 65A/G Expression of HIV GagPol.

1. Aliquots of MVA 65A/G infected BS-C-1 cell lysates were analyzed by radioimmunoprecipitation (RIP) with monoclonal antibodies T24 and 3537 for expression of Envelope and Gag proteins, respectively (FIG. 10 and FIG. 11). Bands of the correct size corresponding to each of these proteins were detected. Early expression of recombinant proteins was confirmed by infecting the cells in the presence of ARA-C. The recombinant virus was shown to produce gag particles in the supernatant of infected cells by pelleting the $^{35}S$ labeled particles on a 20% sucrose cushion.

2. Repeated passage of MVA 65A/G and analyzing the resultant virus has confirmed that MVA 65A/G is stable through 10 passages of the LVD Seed stock.

3. Sequencing a region of the MVA/HIV 62 genome consisting of the HIV inserts as well as a 1000 base pair region of the MVA genome flanking either sides of the HIV confirmed that the GFP gene has been deleted and the sequence of the HIV inserted genes are correct. FIGS. 12 and 13 show the sequence of the env and gag pol genes in the plasmids.

4. Immunogenicity was assessed by $10^7$ pfu of purified MVA 65A/G inoculated into mice at 0 and 4 weeks. ELISA serum antibodies were assayed in a capture ELISA utilizing gp140 clade A env as the antigen. Table 1 shows the clade A env is immunogenic.

Summary

In summary, we have made a recombinant MVA virus, MVA 65A/G, which expresses the A/G 928 modified, truncated envelope and mutated gag pol. The MVA double recombinant virus was made by homologous recombination of single MVA recombinants, one expressing Env and one expressing Gag Pol. These single MVA recombinants were made using a transiently expressed GFP marker that was deleted in the final viruses. MVA/HIV 65A/G was shown to be stable through repeated passage of the LVD Seed Stock.

Modification to MVA 65A/G Construct to Increase Expression and Immunogenicity

The immunogenicity of MVA 65A/G recombinant virus as measured by ELISA utilizing MVA clade A gp140 env as the antigen showed that MVA 65A/G envelope was not as immunogenic as hoped (See Table 1). This example describes the modification to the MVA 65A/G plasmid transfer vector, pJD-6, which was made to increase expression and immunogenicity of the A/G envelope, and its comparison to the original MVA 65A/G virus.

TABLE 1

Immunogenicity of MVA 65 A/G*

| | | Env ELISA | | P24 ELISA | | Vaccinia ELISA | |
|---|---|---|---|---|---|---|---|
| Immunizing Virus | Animal # | Pre-Bleed | 2x Dose | Pre-Bleed | 2x Dose | Pre-Bleed | 2x Dose |
| MVA 1974 | 1801 | <100 | <100 | <100 | <100 | <100 | >102,400 |
| | 1802 | (pool) | <100 | (pool) | ND | (pool) | >102,400 |
| | 1803 | | <100 | | <100 | | >102,400 |
| | 1804 | | <100 | | <100 | | >102,400 |
| | 1805 | | <100 | | <100 | | >102,400 |
| MVA 65A/G | 1826 | <100 | 6400 | <100 | 12800 | <100 | >102,400 |
| | 1827 | (pool) | 3200 | (pool) | <100 | (pool) | >102,400 |
| | 1828 | | 200 | | <100 | | 51,200 |
| | 1829 | | 200 | | 1600 | | >102,400 |
| | 1830 | | 1600 | | 400 | | 102,400 |

*ELISA titers from serum of five mice individually assayed which were immunized twice with $10^7$ PFU of the designated virus. Serum antibody responses were assayed by a 2 day ELISA utilizing secreted Clade A 928 gp140, commercial p24, and purified vaccinia virus as the antigens for the Clade A ELISA response.

Modification to pJD-6

Figure 14:
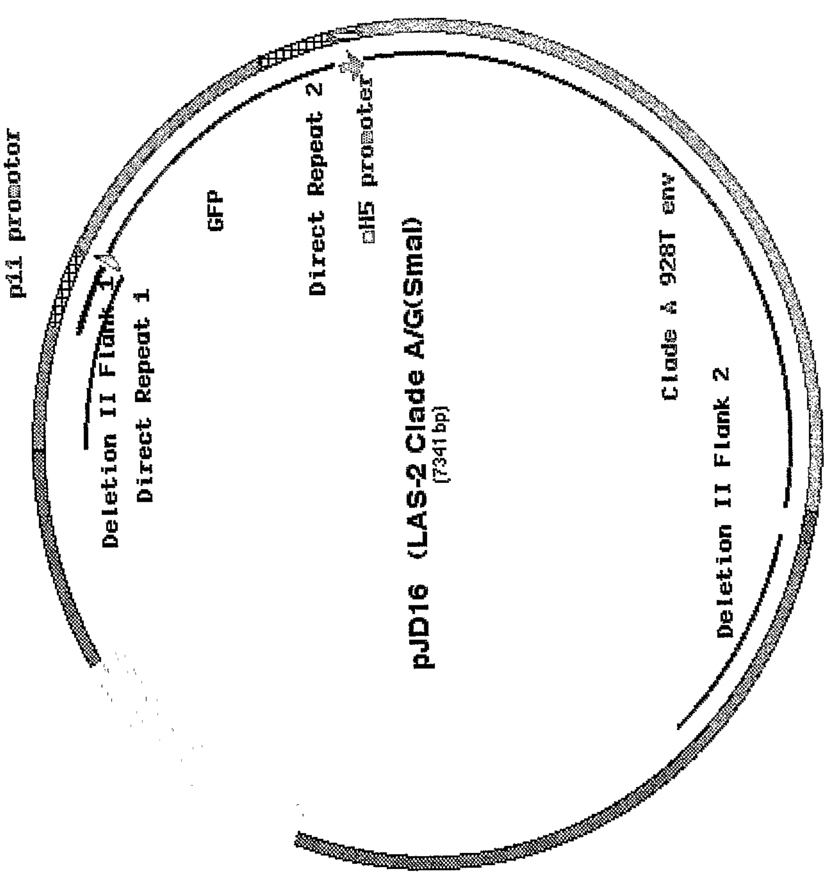
FIG. 14. pJD-16 transfer vector.

The plasmid transfer vector, pJD-6 was modified in the following way:

1. The A/G envelope gene was PCR amplified from pJD-6 with oligos which incorporated a SmaI site at the 5' end of the clade A/G and a NotI site at the 3' end of the env gene. This insert was cloned into the SmaI and NotI site of the pLAS-2 insertion vector making a transfer vector, JD-16 (FIG. 14). This plasmid differed from pJD-6 (which had been used to make MVA 65 A/G recombinant virus) in only one respect, the intervening sequences between the end of the promoter and the start site of the env gene within the multiple cloning region (see #2 for further explanation).

2. In pJD-6, the A/G 928 env was cloned into the multiple cloning site of pLAS-2 using the NotI restriction site. In this arrangement there is an intervening initiation codon between the promotor and the initiation codon of the envelope (part of the SphI restriction enzyme site). In pJD-16, the A/G 928 env was cloned into the multiple cloning site of pLAS-2 using the SmaI site at the beginning of the gene and Not I at the end of the gene, thus eliminating this intervening initiation codon. Thus, the intervening sequences between the end of the promoter and the start site of the env gene within the multiple cloning region are the only difference in the two plasmids as described below:

| Plasmid Transfer Vector | End of Promoter | Intervening Sequences | Start of Env |
|---|---|---|---|
| pJD-6 | TAAATA (SEQ ID NO: 7) | AGCCCGGGGATCCTCTAGAGTCG ACCTGCAGGCATGCTCGAGCGGC CGCACC (SEQ ID NO: 8) | ATGAGAGTG (SEQ ID NO: 10) |
| pJD-16 | TAAATA (SEQ ID NO: 7) | AGCCCGGGACC (SEQ ID NO: 9) | ATGAGAGTG (SEQ ID NO: 10) |

Double Recombinant MVA Construction

To make the double recombinant MVA virus with the JD-16 plasmid, the single MVA recombinant virus expressing the gag pol of the A/G virus, vJD5gag pol, as described above in the original MVA 65A/G construct, was used to infect CEF, and pJD-16 was transfected into this infected culture. Virus isolation proceeded as described above for the original MVA/HIV 65A/G virus and the resulting double recombinant virus (Clone D1.3266-15), was designated MVA/HIV 65A/G(SmaI).

Characterization and Comparison of the Original MVA/HIV 65A/G with the Modified MVA/HIV 65A/G(SmaI)

Figure 15:
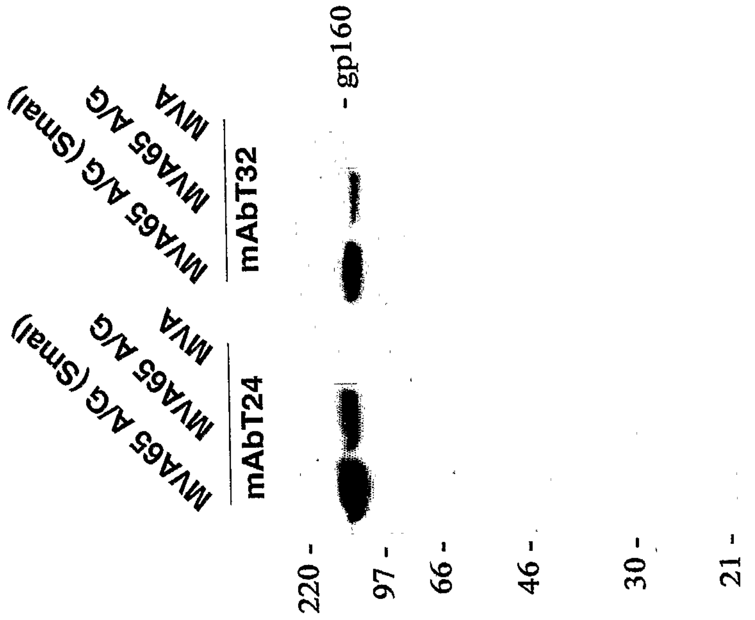
FIG. 15. Enhanced Envelope expression from modified MVA 65A/G.
Figure 16:
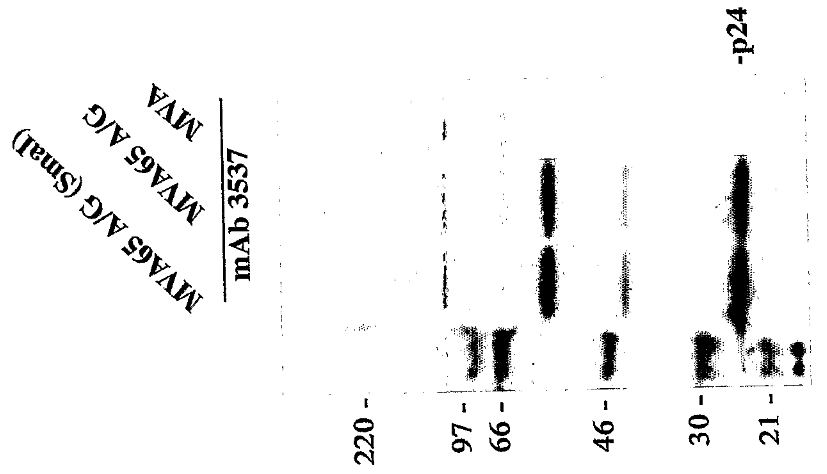
FIG. 16. Gag expression from MVA 65A/G constructs.

1. Aliquots of MVA/HIV 65A/G and MVA/HIV 65A/G (SmaI) infected BS-C-1 cells were analyzed by RIP with monoclonal Antibodies T24 and T32 mAb for the env (FIG. 15) and 3537 (183-H12-5C, NIH AIDS Research and Reference Reagent Program) mAb for the gag expression (FIG. 16). Utilizing Image Quant program, the amount of protein immunoprecipitated with T24 from each construct was quantitated. and Env expression was 2 fold higher with modified 65A/G(SmaI) compared to MVA 65A/G. MVA 65A/G (SmaI) was shown to produce gag particles in the supernatant of infected cells by pelleting $^{35}S$ labeled particles through a 20% sucrose cushion.

Figure 17:
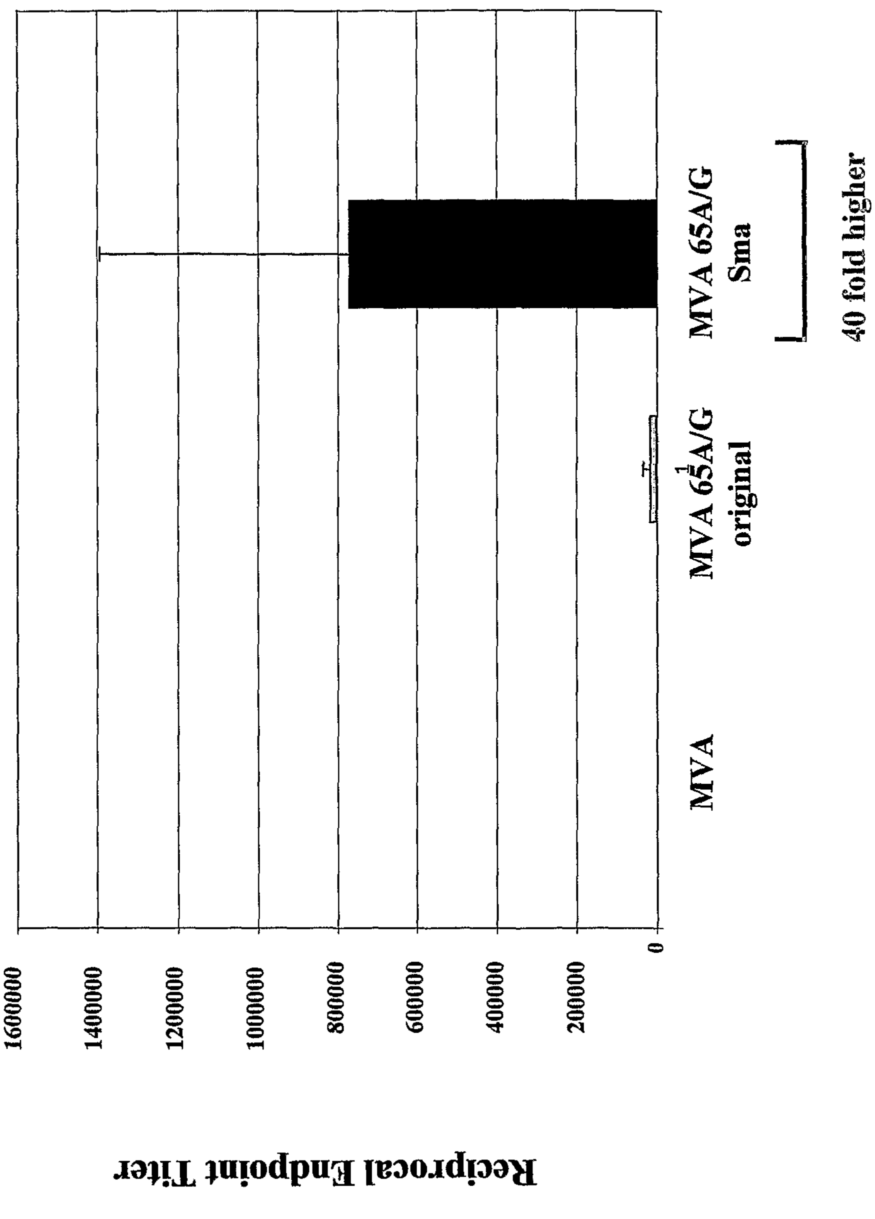
FIG. 17. Clade A/G gp140 ELISA titers from immunized mice.

2. Immunogenicity of the modified 65A/G(SmaI) virus was assessed in mice immunized 2× with either MVA 65A/G or modified MVA 65A/G(SmaI) at $10^7$ dose given IM three weeks apart. The average ELISA titer from serum of five mice (individually assayed) with the designated virus was determined. Serum antibody responses were assayed by a 2 day ELISA utilizing secreted Clade A 928 strain gp140 as the antigen. The results in FIG. 17 indicate that the modified construct (MVA 65A/G (SmaI) Env is about 40 times more immunogenic than the original MVA 65A/G construct.

Figure 18:
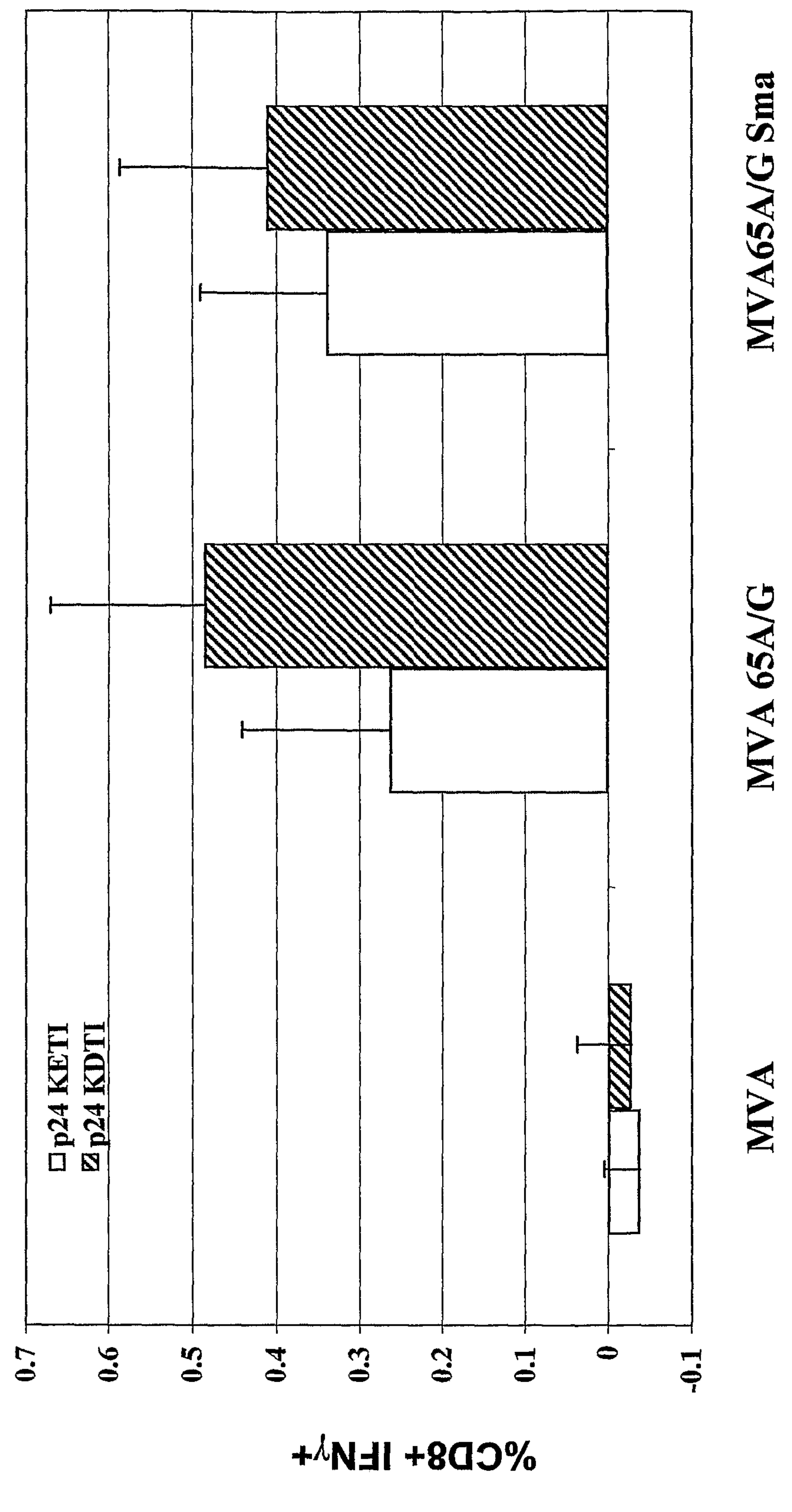
FIG. 18. Clade A p24 peptide ICS response.

The 2 different viruses were also tested for their ability to induce a cellular immune response of the Gag protein as measured by intracellular cytokine staining. Mice (5/group) were immunized twice with $10^7$ pfu of the designated viruses. Splenocytes from individual mice were assayed directly ex vivo after overnight culture with 2 different gag p24 peptide-pulsed P815 cells. $CD8^+$ IFN-$\gamma^+$ cells were enumerated by flow cytometry. As shown in FIG. 18, both of the constructs had similar intracellular cytokine staining (ICS) response to the gag peptides. This would be expected as the gag virus used to make the 2 constructs was identical.

3. Repeated passage of MVA 65A/G(SmaI) and analyzing the expression of the resultant virus has confirmed that the envelope expression of modified MVA 65A/G(SmaI) is highly unstable as shown in Table 2.

TABLE 2

Instability of Modified MVA A/G Construct

| | % of Nonstaining Plaques | | | |
|---|---|---|---|---|
| | MVA 65 A/G original | | MVA 65 A/G (Sma) | |
| Passage | Env | Gag | Env | Gag |
| LVD Seed | <3 | 2 | <2 | <1 |
| P2 | <1 | <1 | ND | ND |
| P3 | <1 | 2 | 28 | 1 |
| P4 | <1 | <1 | ND | ND |
| P5 | <1 | <1 | 75 | <1 |
| P6 | <1 | <1 | | |
| P7 | 2 | <1 | | |
| P8 | <1 | <1 | | |

Summary

Thus, removal of the intervening codon initiation site, through recloning of the envelope into a closer site to the promoter, made a virus which expressed larger quantities of env and was much more immunogenic; however it could not be pursued as a candidate vaccine because it was highly unstable (Table 3).

TABLE 3

Clade A/G summary

| Properties | MVA 65A/G (original) | MVA 65A/G Sma |
|---|---|---|
| LVD Seed Stock Titer (pfu/ml) | $5.5 \times 10^8$ | $2.5 \times 10^8$ |
| HIV Env expression | 1 | 2 |
| HIV Gag expression | 1 | 1.3 |
| Immunogenicity | | |
| Env ELISA | 1 | 40 |
| CD8+ Gag | 1 | 0.8 |
| Stability | 1 | unstable |

EXAMPLE 3

MVA Recombinants Expressing Clade B Env, Gag, and Pol

MVA/HIV 62B Construction and Characterization

This example describes the construction of a modified vaccinia virus Ankara (MVA) recombinant virus, MVA/HIV 62B, expressing clade B HIV strains ADA Env and chimeric HXB2/BH10 Gag Pol. This virus differs from an earlier MVA clade B recombinant, MVA/HIV 48, (which also expresses identical HIV strain ADA Env and HXB2/BH10 Gag Pol) in 4 ways:

1) MVA/HIV 62B uses a transient screening marker of green fluorescent protein (GFP) instead of GUS screening marker used in MVA/HIV 48.

2) The env gene is inserted into del II of MVA genome and the gag pol is inserted in del III. In MVA/HIV 48, both env and gag pol are inserted into del IR.

3) Both env and gag pol of MVA/HIV 62B are controlled by PmH5, the same promoter controlling gag pol in MVA/HIV 48.

4) The MVA virus used to make the recombinant MVA/HIV 62B is MVA 1974/NIH Clone 1 instead of MVA 1983/NIH Clone 1 used to make MVA/HIV 48.

Plasmid Transfer Vectors

The plasmid transfer vectors, pLAS-1 HXB2/BH10 Gag Pol, and pLAS-2 ADA Env (FIG. 19 and FIG. 20 respectively), were used to make single recombinant MVAs by homologous recombination. Each of these plasmids carry the transient GFP marker, and were constructed as follows:

1. The clade B gag pol was truncated so that the integrase was remove and was cloned into the plasmid so that it was controlled by the mH5 promoter. This gene contained the complete HXB2 sequence of the gag. The pol gene has reverse transcriptase safety mutations in amino acid 185 within the active site of RT, in amino acid 266 which inhibits strand transfer activity, and at amino acid 478 which inhibits the Rnase H activity. In addition, the integrase gene is deleted past EcoRI site.

Figure 19:
FIG. 19. pLAS-1 HXB2/BH10 Gag Pol transfer vector.

2. pLAS-1 was constructed from pLW-51GFP by cutting out the Psyn II vaccinia promoter, blunting and religating. Clade B HXB2/BH10 gag pol sequences from MVA/HIV 48 was cloned into pLAS-1, making the plasmid transfer vector, pLAS-1 HXB2/BH10 Gag Pol (FIG. 19).

3. The ADA envelope is a truncated version with silent 5TNT mutations. The envelope was truncated in the cytoplasmic tail of the gp41 gene, deleting 115 amino acids of the cytoplasmic tail. This truncation was shown by us to increase the amount of envelope protein on the surface of infected cells and enhance immunogenicity of the envelope protein in mice, and stability of the recombinant virus in tissue culture.

Figure 20:
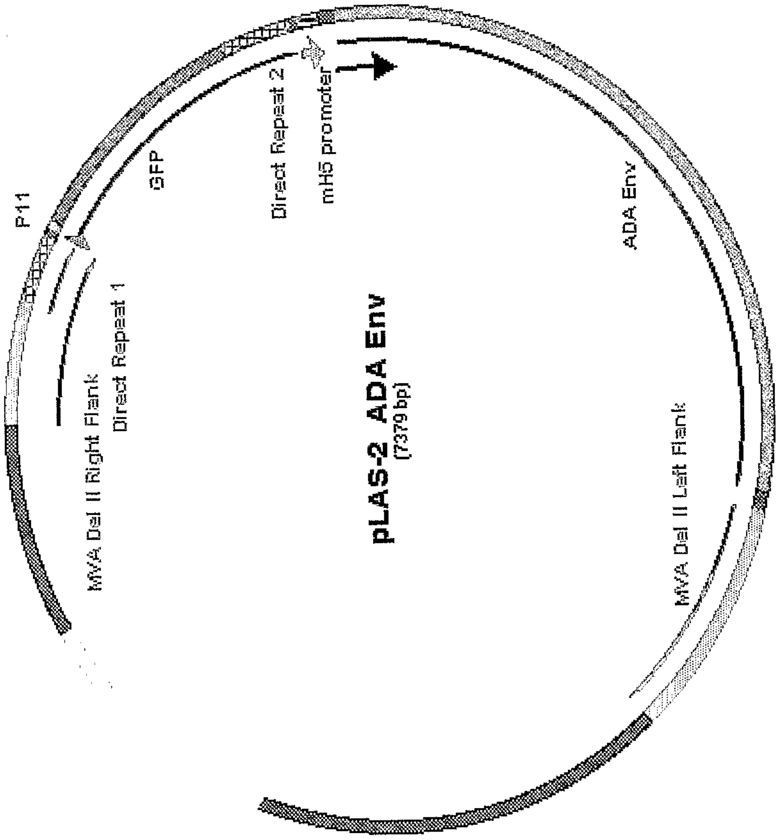
FIG. 20. pLAS-2 ADA Env transfer vector.

4. pLAS-2 was constructed by a insertion of a direct repeat of the MVA flank as described under LAS-2 construction followed by an insertion of GFP controlled by P11 vaccinia promoter. Addition of the above ADA modified env sequences from MVA/HIV 48 made plasmid transfer vector pLAS-2 ADA Env (FIG. 20).

Single Recombinant MVA Construction

1. MVA 1974/NIH Clone 1 virus, which was derived from an MVA received from Anton Mayr (Munich, Germany) at passage 572 from Feb. 22, 1974 by terminally diluting 3 times at the National Institutes of Health, was used for recombination.

2. Secondary CEF cells were infected at an MOI of 0.05 of MVA and transfected with 2 μg of pLAS-1 HXB2/BH10 Gag Pol or 2 μg of pLAS-2 ADA Env (FIG. 21). These two virus constructions were carried in like manner as described below, but independently.

3. Following a two day incubation at 37° C., the viruses were harvested, frozen and thawed 3×, and plated out on CEF.

4. At 3 days post-infection, those foci of infections that exhibited GFP fluorescence (indicating that recombination had occurred between the plasmid and the infecting virus) were picked and replated on CEF. Again, those foci that expressed GFP were picked.

5. These 2× plaque-purified GFP-expressing foci were plated out in triplicate CEF plates and two plates were analyzed for GFP fluorescence and Gag or Env expression. Individual foci were picked from the 3rd replicate plate of those samples with little or no GFP fluorescence as well as mostly Gag or Env staining foci.

6. These foci were again plated out in triplicate, and analyzed the same way 2 additional times (3× for the Gag Pol construct). The resulting viruses derived expressed either Gag Pol (MVA 60) or Env (MVA 61) proteins but had deleted the GFP gene by recombination of the double repeats.

Double Recombinant MVA Construction

1. To make the double MVA recombinant, MVA/HIV 62B, the two single recombinant MVA viruses, MVA 60 and MVA 61, expressing Gag Pol and Env respectively, were used to infect CEF cells together at a MOI of 5, grown at 37° C. for 2 days and harvested (FIG. 21).

2. Duplicate plates of the harvest were infected at different dilutions, and one plate was fixed and stained with T8 mAb and number of foci of infected cells that had rounded up CPE (characteristic of Gag Pol recombinants) were scored in order to assure there were double recombinants in the population. Then, foci with the rounded up morphology were picked from the unstained duplicate plate.

3. These foci were plated out at various dilutions in triplicate and immunostained for Env expression (T8 mAb) and Gag expression (3537 mAb, 183-H12-5C, NIH AIDS Research and Reference Regent Program). Those foci that stained for both Env and Gag expression were plaque purified further.

4. The virus was expanded in CEF cells and a LVD Seed stock of MVA/HIV 62 was produced. Mycoplasma testing by ATCC was negative. Sterility testing by BioReliance was negative.

Characterization of MVA Recombinant Virus, MVA/HIV 62B

Figure 22:
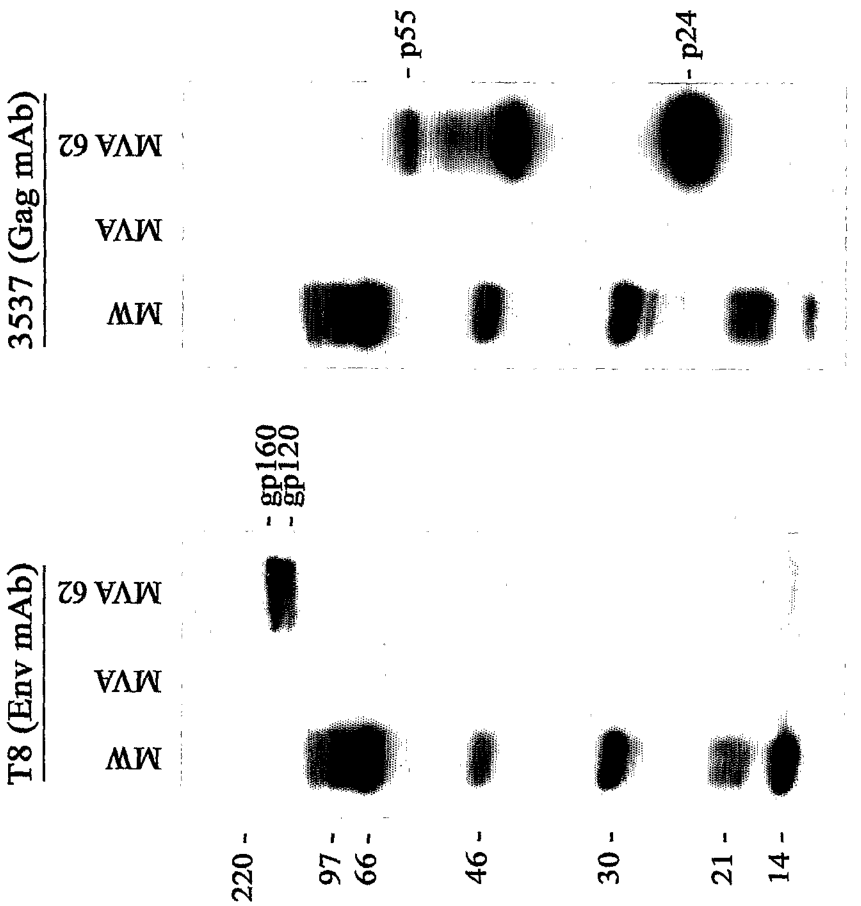
FIG. 22. Expression of HIV Env and gag from MVA 62B.

1. Aliquots of MVA/HIV 62B infected BS-C-1 cell lysates were analyzed by radioimmunoprecipitation (RIP) with monoclonal antibodies T8 and 3537 for expression of Envelope and Gag proteins, respectively (FIG. 22). Bands of the correct size corresponding to each of these proteins were detected. Early expression of recombinant proteins were confirmed by infecting the cells in the presence of ARA-C. The recombinant virus was shown to produce gag particles in the supernatant of infected cells by pelleting the $^{35}S$ labeled particles on a 20% sucrose cushion.

2. Repeated passage of MVA/HIV 62B and analyzing the resultant virus has confirmed that MVA 62B is relatively stable through 10 passages of the LVD Seed stock.

3. Sequencing a region of the MVA/HIV 62B genome consisting of the HIV inserts as well as a 1000 base pair region of the MVA genome flanking either sides of the HIV inserts confirmed that the GFP gene has been deleted and the sequence of the HIV inserted genes are correct. Sequence of ADA Env is given in FIG. 23. Sequence of Gag Pol is given in FIG. 24.

Figure 25:
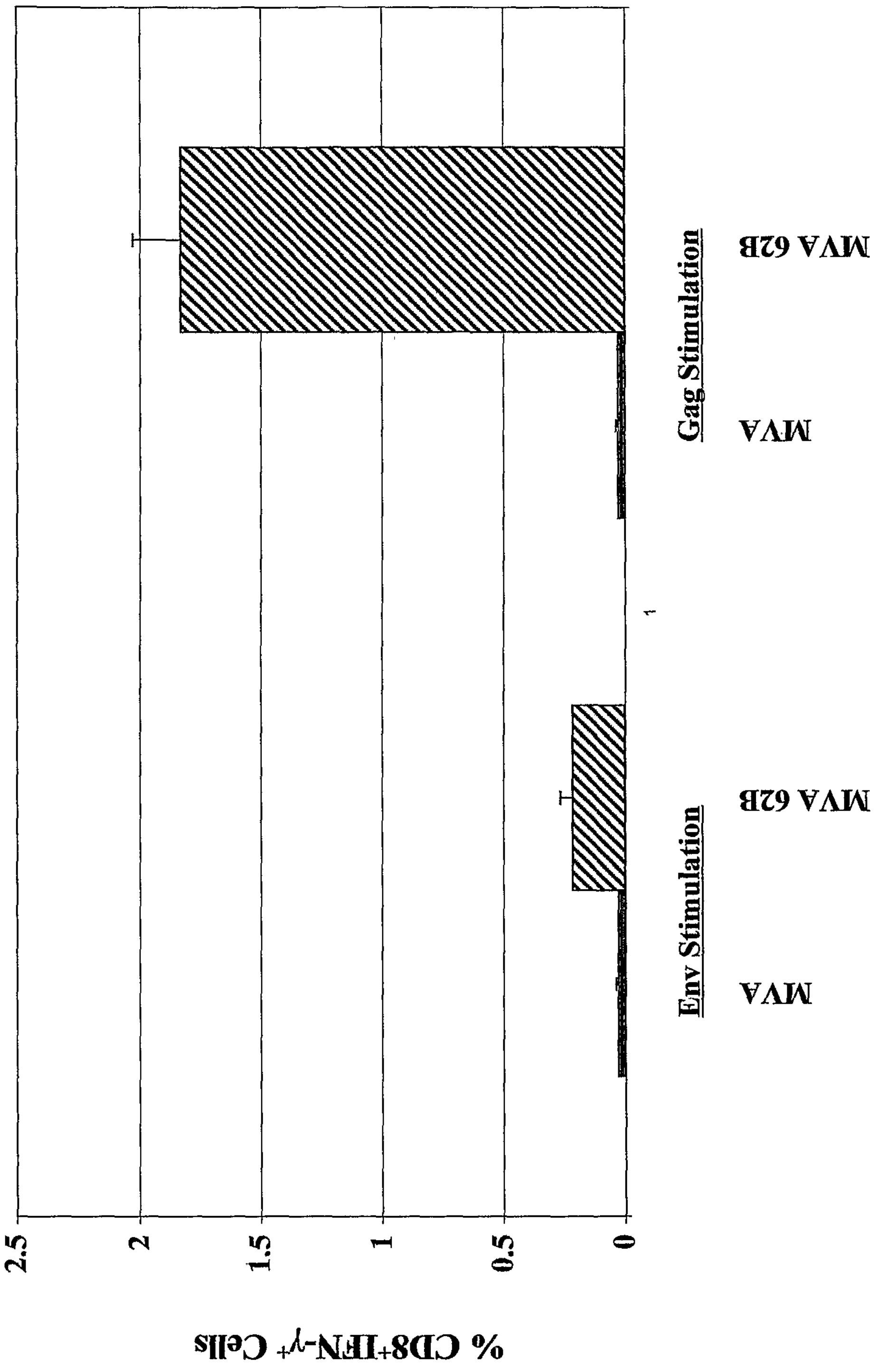
FIG. 25. Intracellular cytokine staining (ICS) Env and gag responses in MVA 62B-immunized mice.

4. Immunogenicity was assessed by $10^7$ pfu of purified MVA 62B inoculated into mice at 0 and 4 weeks. ELISA serum antibodies were assayed in a capture ELISA utilizing gp140 ADA env as the antigen. Table 4 shows the ADA env is immunogenic. FIG. 25 shows the ICS env and gag responses of mice to MVA 62B.

TABLE 4

Immunogenicity of MVA 62B in mice*

| | | Env ELISA | | p24 ELISA | | Vaccinia ELISA | |
|---|---|---|---|---|---|---|---|
| Immunizing virus | Animal # | Pre-Bleed | 2x Dose | Pre-Bleed | 2x Dose | Pre-Bleed | 2x Dose |
| MVA 1974 | 2038 | <100 | <100 | <100 | <100 | <100 | 409,600 |
| | 2039 | (pool) | <100 | (pool) | <100 | (pool) | 409,600 |
| | 2040 | | <100 | | <100 | | 409,600 |
| | 2041 | | <100 | | <100 | | 409,600 |
| | 2045 | | <100 | | <100 | | 204,800 |
| MVA 62B | 2067 | <100 | 500 | <100 | 6400 | <100 | 102,800 |
| | 2069 | (pool) | 25,600 | (pool) | 3200 | (pool) | 204,800 |
| | 2070 | | 256,000 | | 400 | | 204,800 |
| | 2071 | | 2,400 | | <100 | | 409,600 |
| | 2072 | | 102,400 | | 100 | | 409,600 |

*ELISA titers from serum of five mice individually assayed which were immunized twice with $10^7$ PFU of the designated virus. Serum antibody responses were assayed by a 2 day ELISA utilizing secreted Clade B ADA gp140, commercial p24, and purified vaccinia virus as the antigens for the Clade B ELISA response.

Summary

In summary, we have made a recombinant MVA virus, MVA/HIV 62B, which expresses ADA modified, truncated Envelope and HXB2/BH10 Gag Pol. The MVA double recombinant virus was made by homologous recombination of single MVA recombinants, one expressing Env and one expressing Gag Pol. These single MVA recombinants were made using a transiently expressed GFP marker that was deleted in the final viruses. The MVA 62 B virus was shown to make particles and was immunogenic in mice. MVA/HIV 62B was shown to be stable through repeated passage of the LVD Seed Stock.

Modifications to MVA 62B Construct to Increase Expression and Immunogenicity

The immunogenicity of MVA 62B in mice as measured by ELISA utilizing MVA clade B gp140 as the antigen (Table 4) showed that MVA 62B envelope was not as immunogenic as hoped. This example describes the modifications to the MVA 62B plasmid transfer vector, pLAS-2 ADA Env, which were made to increase expression and immunogenicity of the ADA envelope in the final MVA 62 B double recombinant viruses.

Plasmid Transfer Vector Modification

Figure 26:
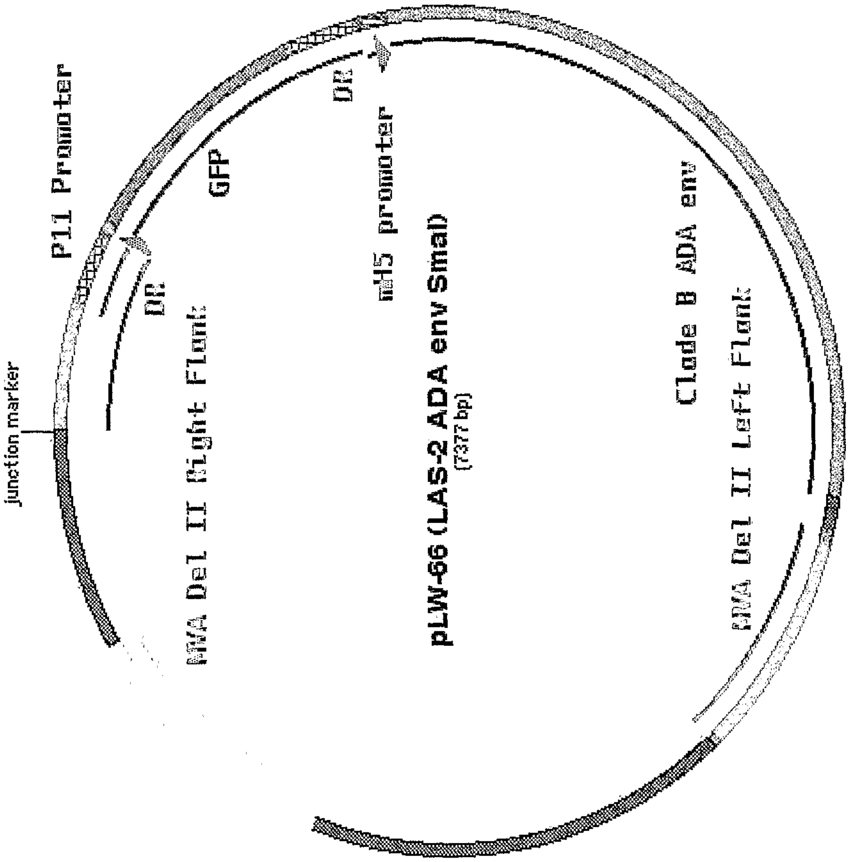
FIG. 26. pLW-66 transfer vector.

The plasmid transfer vector, pLAS-2 ADA Env was modified in the following ways:

1. The ADA env was cut out of JD-9 ADA Env by treating with the restriction enzyme, XmaI (an isoschizmer of SmaI which cuts making overlapping ends compared to the blunt cut of SmaI), and inserted into the XmaI site in LAS-2 making plasmid pLAS ADA Env (SmaI) or as it was designated pLW-66 (FIG. 26). This plasmid differed from pLAS-2 ADA Env (which had been used to make MVA 62 B recombinant virus) in only one significant respect, the intervening sequences between the end of the promoter and the start site of the env gene within the multiple cloning region. (It also differed from pLAS-2 ADA Env in the cloning region of the end of env gene because of the way it was cloned into the plasmid, but this is not of consequence to the expression of the gene.) (see #3 for further explanation).

Figure 27:
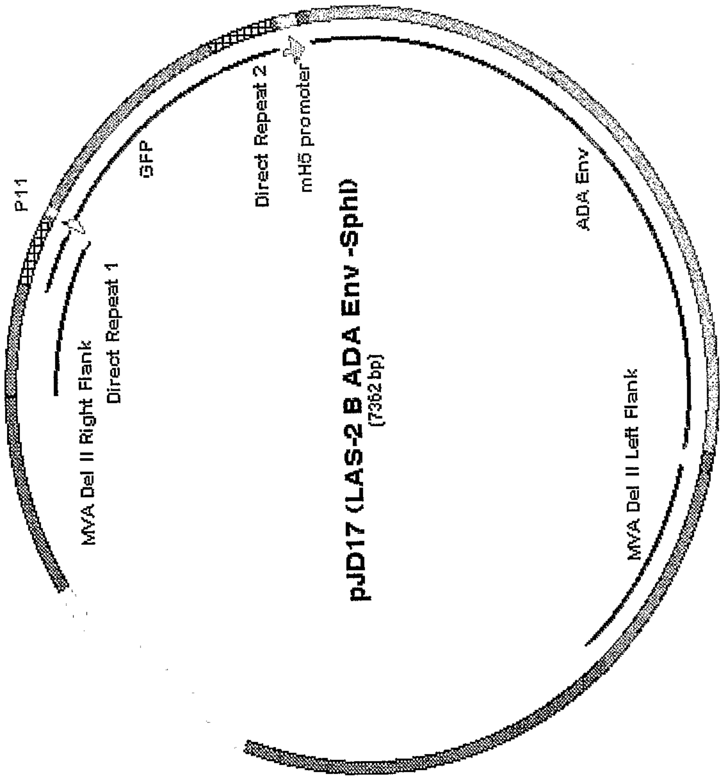
FIG. 27. pJD-17 transfer vector.

2. pLAS-2 ADA Env was digested with restriction enzyme Sal I followed by XhoI to cut out the SphI site (which contains an initiation codon) and religated together to make pJD-17 (FIG. 27). This plasmid differed from pLAS-2 ADA Env (which had been used to make MVA 62 B recombinant virus) in only one respect, the intervening sequences between the end of the promoter and the start site of the env gene within the multiple cloning region (see #3 for further explanation).

Figure 28:
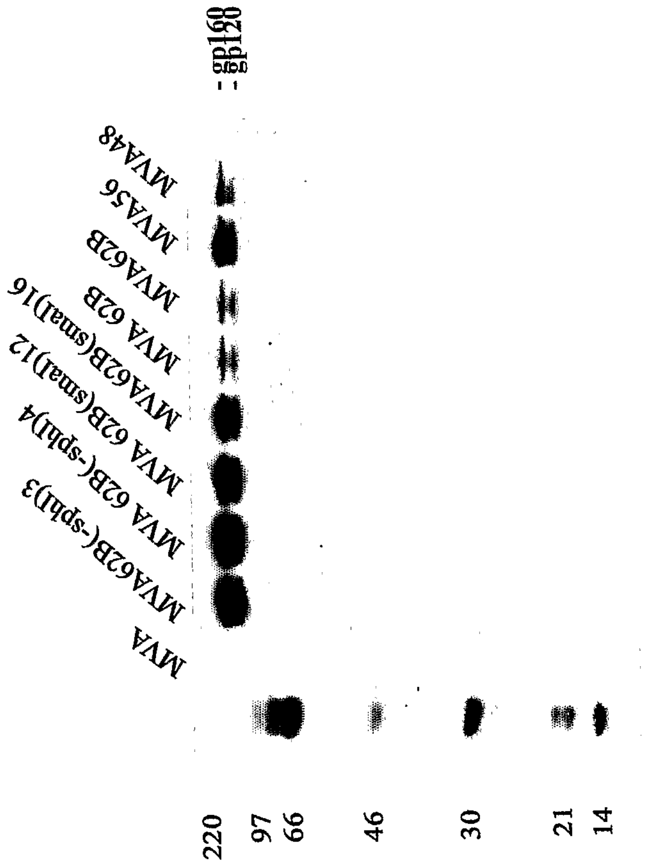
FIG. 28. Enhanced expression of modified MVA 62B constructs.
Figure 29:
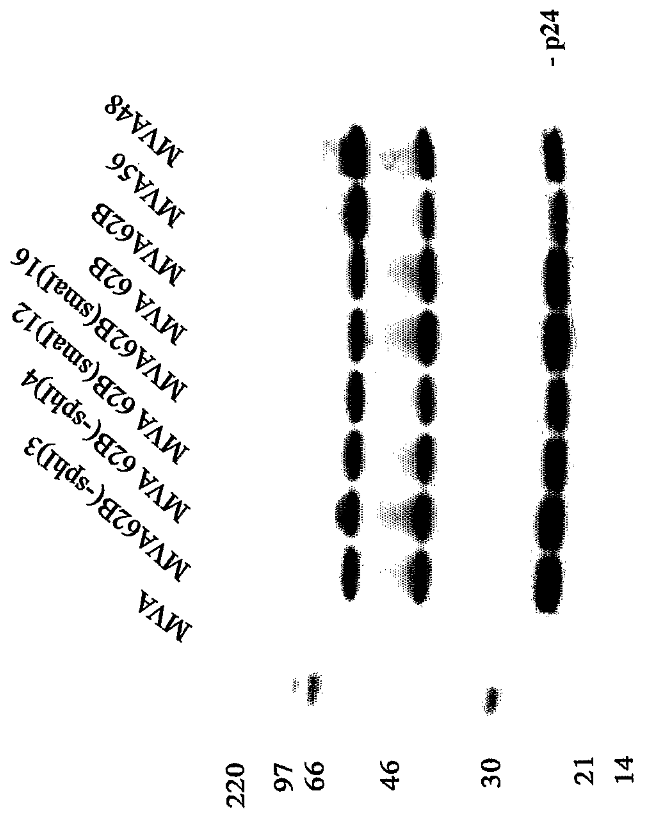
FIG. 29. Expression of Gag from the modified MVA 62B constructs.

3. In plasmid pLAS-2 ADA Env, the ADA envelope had been cloned into the Not I site generating the following nucleotide sequence between the promoter. In pLW-66, the ADA env was cloned into the XmaI site (SmaI) generating the following sequence between the vaccinia mH5promoter and the ADA env initiation codon as depicted below. In pJD-17 the SphI site had simply been removed. This all shown below:

Characterization and Comparison of the Original MVA/HIV 62B with the Modified MVA/HIV 62B Viruses 1. Aliquots of MVA/HIV 62B and 4 modified MVA 62B virus infected BS-C-1 cells were analyzed by RIP with monoclonal antibody T8 for the env (FIG. 28) and 3537 mAb for the gag expression (FIG. 29). Utilizing Image Quant program, the amount of protein immunoprecipitated with T8 from each construct was quantitated. and Env expression was 2.6-3.3 fold higher with the modified constructs compared to MVA 62B. All of the MVA62B constructs were shown to produce gag particles in the supernatant of infected cells by pelleting $^{35}S$ labeled particles through a 20% sucrose cushion.

Figure 30:
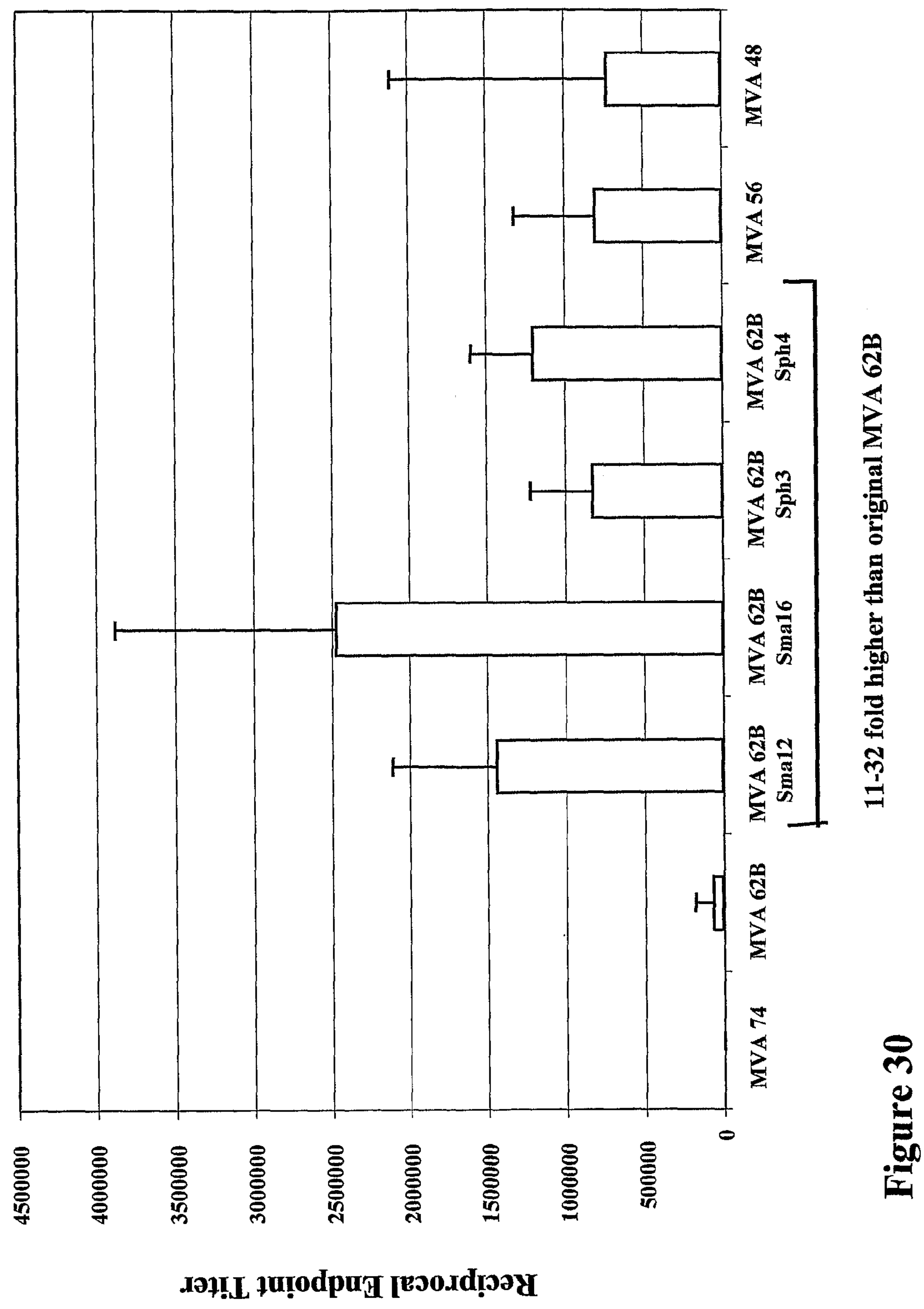
FIG. 30. Enhanced gp140 ELISA titers with modified constructs in mice.

2. Immunogenicity of the modified MVA62B constructs were assessed in mice immunized 2× with either the original or modified MVA 62B viruses at $10^7$ dose given IM three weeks apart. FIG. 30 shows the average ELISA titer from serum of five mice (individually assayed). Serum antibody responses were assayed by a 2 day ELISA utilizing secreted Clade B ADA gp140 as the antigen. The results indicate that the modified constructs are 11-32 fold more immunogenic than the original construct in this assay of the envelope immunogenicity.

The different viruses were also tested for their ability to induce a cellular immune response to the Env or Gag protein as measured by intracellular cytokine staining (ICS). Mice (5/group) were immunized twice with $10^7$ pfu of the designated viruses. Splenocytes from individual mice were assayed directly ex vivo after overnight culture with the env peptide or gag p24 peptide-pulsed P815 cells. $CD8^+$ IFN-$\gamma^+$ cells were enumerated by flow cytometry.

| Plasmid Transfer Vector | End of Promoter | Intervening Sequences between promoter and start of Env | Start of Env |
|---|---|---|---|
| pLAS-2 ADA Env | TAAATA (SEQ ID NO: 7) | AGCCCGGGGATCCTCTAGAGTC GACCTGCAGGCATGCTCGAGCG GCCGCACC (SEQ ID NO: 8) | ATGAAAGTG (SEQ ID NO: 10) |
| PLW-66 | TAAATA (SEQ ID NO: 7) | AGCCCGGGACC (SEQ ID NO: 9) | ATGAAAGTG (SEQ ID NO: 10) |
| PJD-17 | TAAATA (SEQ ID NO: 7) | AGCCCGGGGATCCTCTAGAGTC GAGCGGCCGCACC (SEQ ID NO: 11) | ATGAAAGTG (SEQ ID NO: 10) |

Double Recombinant MVA Construction

To make the double recombinant MVA virus with the pLW-66 and pJD-17 plasmids, the single MVA recombinant virus expressing the gag pol of the clade B virus, MVA 60, as described above, was used to infect CEF cells, and pLW-66 or pJD-17 was transfected into these infected CEF cultures. Virus isolation proceeded as described above for the original MVA/HIV 62B virus and the two clones of each resulting double recombinant viruses were designated as follows:

| Plasmid Used | Clone number | Final Virus Designation |
|---|---|---|
| pLW-66 | 12 | MVA 62B (SmaI)12 |
| pLW-66 | 16 | MVA 62B (SmaI)16 |
| pJD-17 | 3 | MVA 62B (-SphI)3 |
| pJD-17 | 4 | MVA 62B (-SphI)4 |

Figure 31:
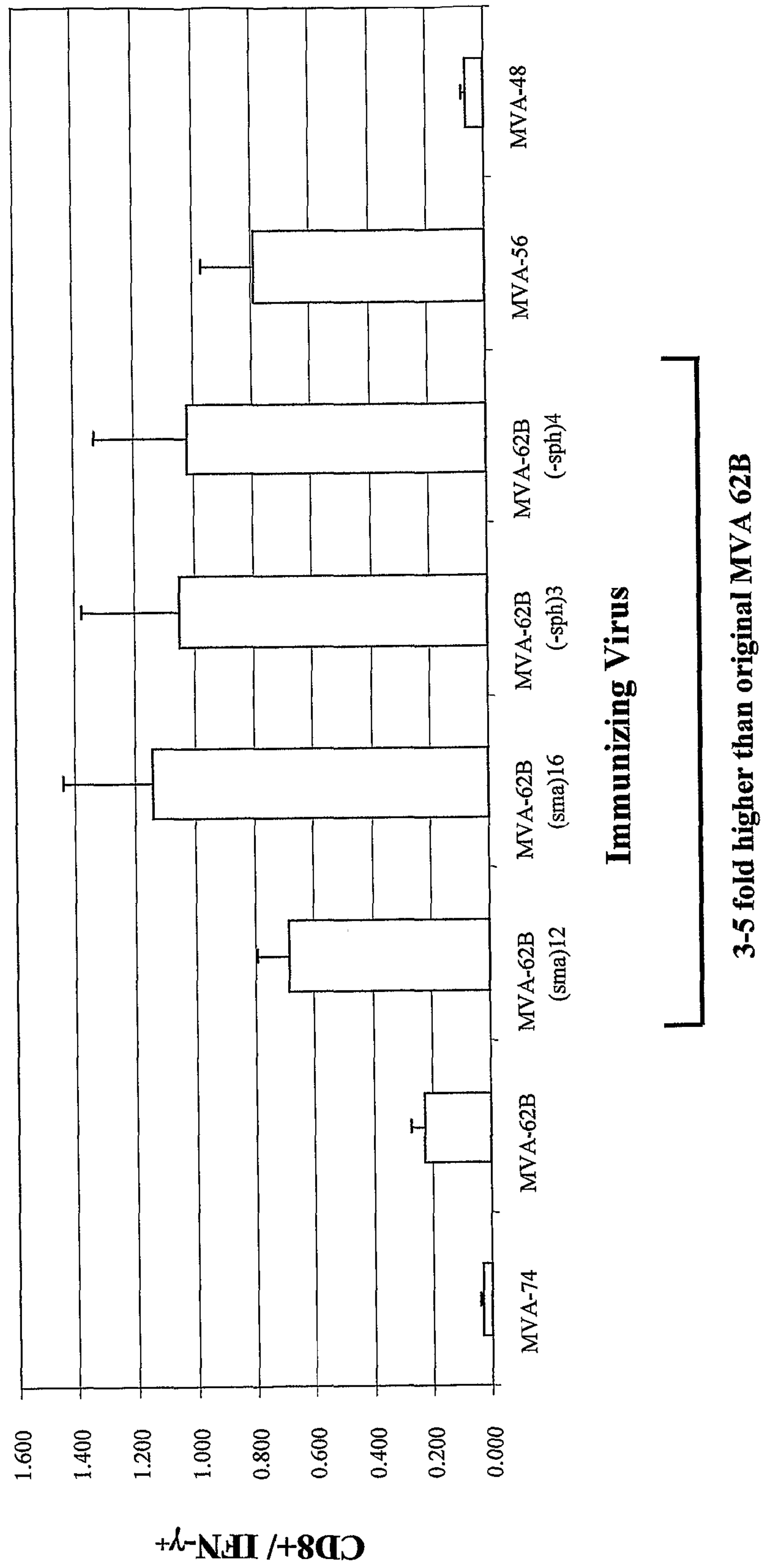
FIG. 31. Enhanced ICS Env response with modified constructs.

As shown in FIG. 31, the modified 62B constructs all made an enhanced ICS Env response compared to the original. All were 3-5 fold higher than original MVA 62B.

Figure 32:
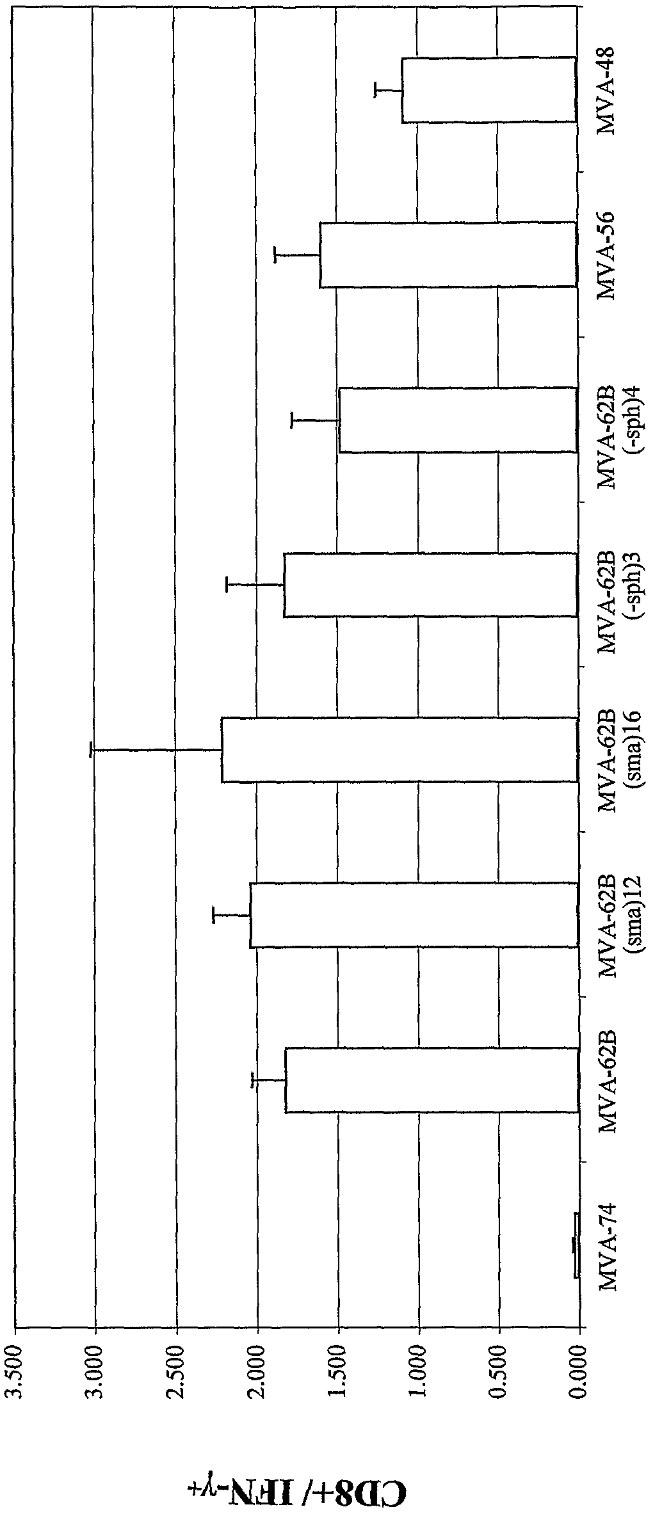
FIG. 32. ICS Gag response.

As shown in FIG. 32, all of the MVA 62B constructs whether original or modified had similar ICS response to the gag peptide (no more than a two fold variation). This would be expected as the gag virus used to make the modified MVA 62B constructs was identical.

3. Repeated passage of the modified MVA/HIV 62B viruses and analyzing the resultant virus has confirmed that MVA 62B is relatively stable through 10 passages of the LVD Seed stock.

Summary

Thus, removal of the intervening codon initiation site, through recloning of the envelope into a closer site to the promoter, made viruses which expressed larger amounts of env and were much more immunogenic. These viruses are being pursued as candidate vaccine viruses (Table 5).

TABLE 5

| Original and Modified MVA62B constructs | | | | | |
|---|---|---|---|---|---|
| Properties | MVA62B (original) | MVA62B (SmaI)12 | MVA62B (SmaI)16 | MVA62B (-SphI)3 | MVA62B (-SphI)4 |
| LVD seed stock titer (pfu/ml) | $5.3 \times 10^8$ | $6.7 \times 10^8$ | $6.4 \times 10^8$ | $6.7 \times 10^8$ | $3.3 \times 10^8$ |
| Growth on passage | 1 | 0.7 | 0.8 | ND | 0.3 |
| HIV Env expression | 1 | 206 | 2.7 | ND | 3.2 |
| HIV Gag expression | 1 | 0.7 | 0.7 | 0.8 | 0.9 |
| Immuno-genicity | | | | | |
| Env ELISA | 1 | 19 | 32 | 44 | 16 |
| CD8 + Env | 1 | 3 | 5 | 4.6 | 4.8 |
| CD8 + Gag | 1 | 1.1 | 1.2 | 1 | 0.8 |
| Stability | 1 | 1 | 1 | ND | 1 |

MVA 56 Construction and Characterization

This example describes the construction of a modified vaccinia virus Ankara (MVA) recombinant virus, MVA/HIV clade B expressing HIV strain ADA env and chimeric HXB2/BH10 gag pol. This virus differs from an earlier MVA recombinant, MVA/HIV 48, (which also expresses the HIV strain ADA env and the HXB2/BH10 gag pol) in 3 ways:

1. MVA/HIV 56 uses a transient screening marker of green fluorescent protein (GFP) instead of the GUS screening marker used in MVA/HIV 48.

2. The ADA env of MVA/HIV 56 is controlled by a new modified vaccinia virus promoter, Pm2H5, which allows more early expression of ADA env than the Psyn II promoter used to express the ADA env in MVA/HIV 48. (The gag pol is controlled by the vaccinia virus mH5promoter, the same promoter controlling the gag pol in MVA 48.)

3. The MVA virus used to make the recombinant MVA/HIV 56 is MVA 1974/NIH Clone 1 instead of MVA 1983/NIH Clone 1, used to make MVA/HIV 48.

It differs from later constructs of original MVA 62B and modified MVA 62B in that the env and gag genes are controlled by double vaccinia virus promoters which are in tandem, like in MVA 48, and insert into only deletion III of the MVA genome. This gives this type of construct a construction advantage over the MVA 62B constructs since one has to go through only one set of plaque purifications as compared to the construction regime of the MVA 62B constructs.

All clade B constructs described have the same modified ADA env and modified HXB2/BH10 gag pol.

Plasmid Transfer Vector

The plasmid transfer vector, pLAS-6, used to make MVA/HIV 56 by homologous recombination was constructed as follows:

1. The GUS screening marker was cut out of the plasmid, pLW-48 (see WO 002/072759), and replaced with the GFP screening marker run by the vaccinia virus P11 promoter (pLW-51 GFP). This GFP screening marker was used transiently to 2× plaque-purify recombinant virus, but was deleted in the final recombinant by homologous recombination (because GFP was flanked by two direct repeats).

2. The Psyn II vaccinia promoter was cut out of pLW-51GFP by XhoI and NotI digestion and replaced with a new further modified H5 vaccinia virus promoter, pm2H5, in the same sites. This new plasmid was named pLAS-5.

Sequence of m2H5 promoter:

```
                                          (SEQ ID NO: 12)
AAAAAATGAAAAACTATTCTAATTTATTAGAGAGTATTGATATATTCATA

GAATTTTTCGCATATAAATA
```

Figure 33:
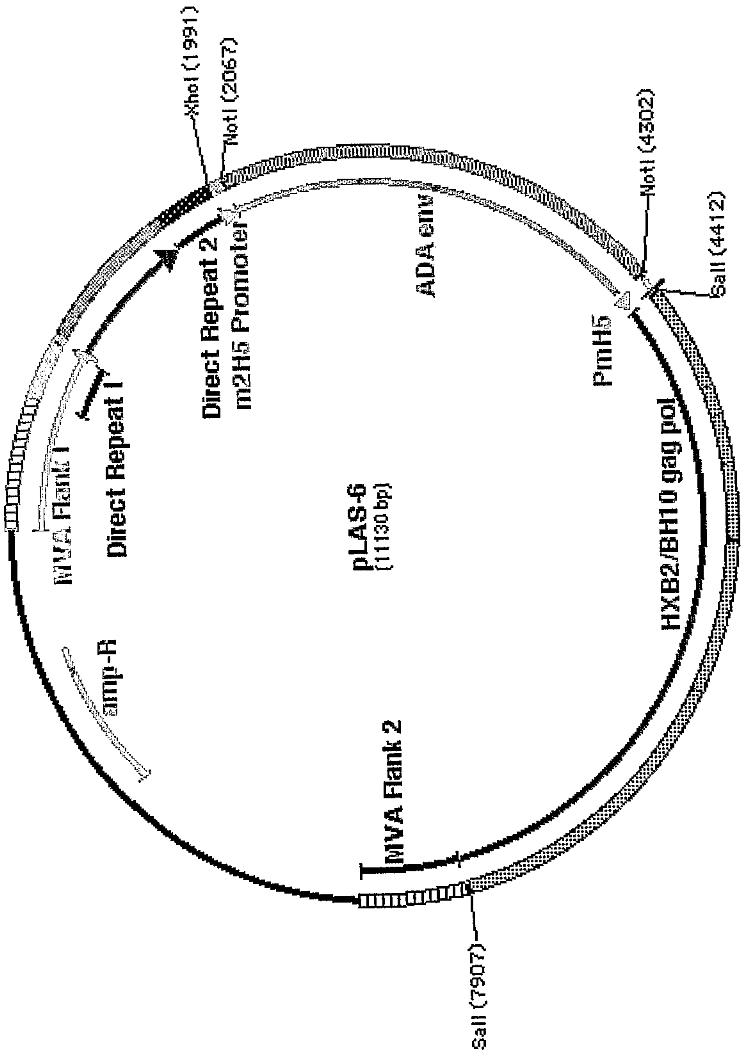
FIG. 33. pLAS-6 transfer plasmid for MVA 56.

3. The ADA env, was removed from pLW-48 by NotI enzyme digestion of the plasmid and cloned into the NotI site of pLAS-5 controlled by the vaccinia virus m2H5 promoter. The HXB2/BH10 gag pol gene was removed from pLW-48 by SalI digestion and placed in the SalI site under the control of the mH5 promoter to make the plasmid transfer vector, pLAS-6 (FIG. 33), which was used to make recombinant virus MVA/HIV 56. The recombinant HIV genes were shown by transfection to be expressed.

Recombinant MVA/HIV 56 Construction

1. MVA 1974/NIH Clone 1 virus, which was derived from an MVA received from Anton Mayr (Munich, Germany) at passage 572 from Feb. 22, 1974 by terminally diluting 3 times at the National Institutes of Health, was used for recombination.

2. Secondary CEF cells were infected at an MOI of 0.05 of MVA and transfected with 2 μg of pLAS-6, the plasmid described above. Following a two day incubation at 37° C., the virus was harvested, frozen and thawed 3×, and plated out on CEF.

3. At 3 days, those foci of infections that expressed GFP (indicating that recombination had occurred between the plasmid and the infecting virus), were picked and replated on CEF. Again, those foci that expressed GFP were picked.

4. These 2× plaque-purified GFP-expressing foci were plated out in triplicate CEF plates and two plates were analyzed for GFP fluorescence and gag pol expression. Individual foci were picked from the 3rd replicate plate of those samples with little or no GFP staining as well as mostly gag staining foci.

5. These foci were again plated out in triplicate, and analyzed the same way 2 additional times. The resulting virus derived expressed the gag protein but had deleted the GFP gene by recombination of the double repeats. By immunostaining, this virus also expressed the env protein. The virus was expanded in CEF cells and a LVD Seed stock was produced and sterility and mycoplasma tested by BioReliance and ATCC, respectively.

Characterization of MVA Recombinant Virus, MVA/HIV 56

Figure 34:
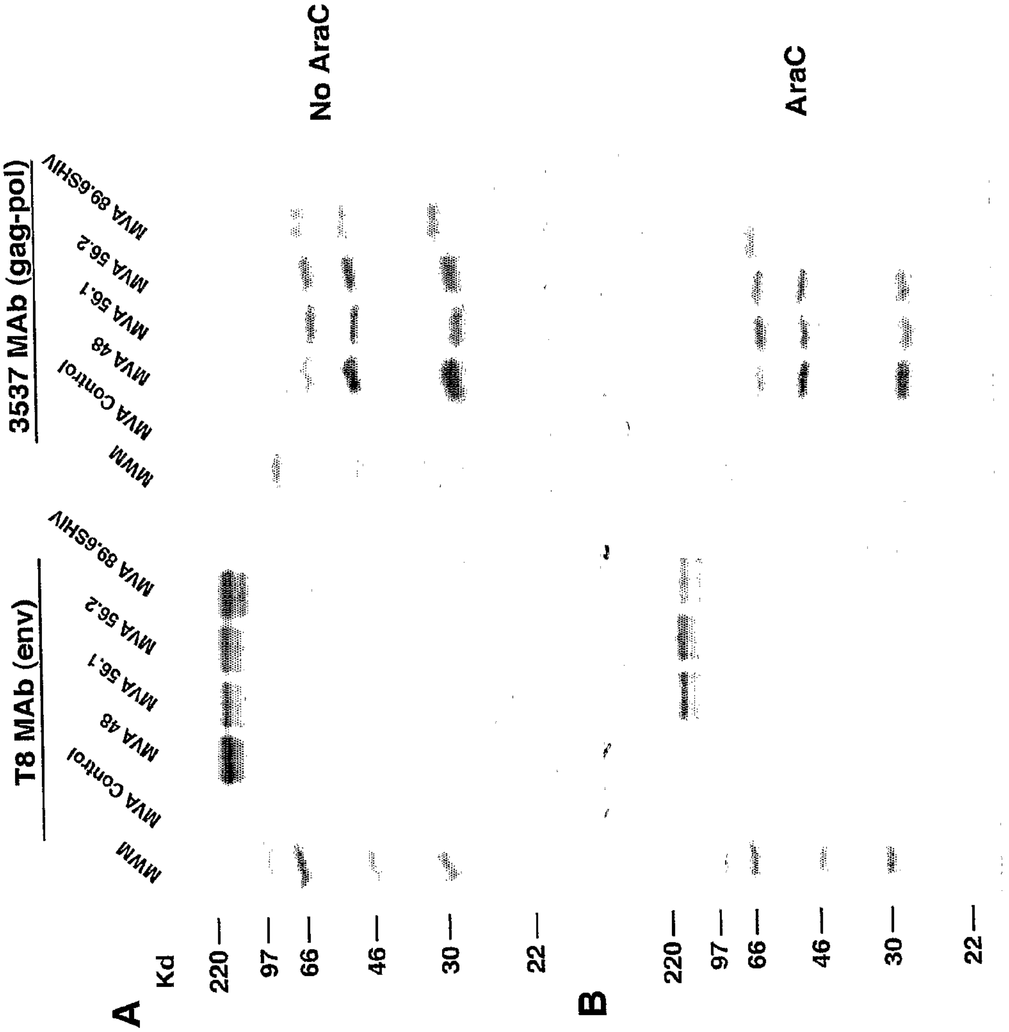
FIG. 34. Env and GagPol expression by MVA recombinants MVA 48 and 56.

1. Aliquots of MVA/HIV 56 infected cell lysates were analyzed by radioimmunoprecipitation (RIP) with monoclonal antibodies for expression of both the envelope and gag proteins, both in the presence and absence of ARA-C. In RIP, bands of the correct size corresponding to each of these proteins was detected, both in the presence and absence of ARA-C indicating both early and late expression of recombinant protein (FIG. 34).

2. MVA/HIV 56 was shown to produce gag particles in the supernatant of infected cells by pelleting the $^{35}S$ labeled particles from supernatant of MVA/HIV 56-infected BS-C-1 cells on a 20% sucrose cushion and analyzing by PAGE.

3. Sequencing a region of the MVA/HIV 56 genome consisting of the HIV inserts as well as a 1000 base pair region of the MVA genome flanking either side of the HIV inserts confirmed that the GFP gene had been deleted and the sequence of the HIV inserted genes was correct.

4. Repeated passage of the modified MVA/HIV 62B viruses and analyzing the resultant virus has confirmed that MVA 62B is relatively stable through 5 passages of the LVD Seed stock.

5. Immunogenicity of MVA 56 was assessed in mice immunized 2× with $10^7$ pfu three weeks apart. FIG. 28 shows the average ELISA titer from serum of five mice (individually assayed). Serum antibody responses were assayed by a 2 day ELISA utilizing secreted Clade B ADA gp140 as the antigen. The results indicate that MVA 56 is able to elicit serum antibodies. MVA 56 was also tested for its ability to induce a cellular immune response of the Env or Gag protein as measured by ICS. Mice (5/group) were immunized twice with $10^7$ pfu of MVA 56. Splenocytes from individual mice were assayed directly ex vivo after overnight culture with the env peptide or gag p24 peptide-pulsed P815 cells. $CD8^+$ IFN-$\gamma^+$ cells were enumerated by flow cytometry. As shown in FIG. 29, MVA 56 induces an env cellular immune response. As shown in FIG. 29, MVA 56 also induces an ICS gag p24 response, similar to the other clade B constructs.

Summary

In summary, we have made a recombinant MVA virus, MVA/HIV 56, which has high expression of ADA modified truncated envelope and HXB2/BH10 gag pol and inserts into deletion III of the MVA genome. The MVA recombinant virus was made using a transiently expressed GFP marker that was deleted in the final virus. High expression of the ADA envelope was possible because of a new hybrid early/late promoter, Pm2H5. The MVA 56 recombinant makes gag particles which has been shown by pelleting the particles through sucrose and analyzing by PAGE. Sequencing of the recombinant region of the MVA genome confirmed the absence of GFP and the correct sequence of the HIV genes. Env ELISA confirmed the immunogenicity of the ADA envelope and cellular response to both the envelope and p24 gag were detected.

EXAMPLE 4

MVA Recombinant Expressing Clade C Env, Gag, Pol

MVA/HIV 71C Construction and Characterization

This example describes the construction of a modified vaccinia virus Ankara (MVA) recombinant virus, MVA/HIV 71C, expressing an Indian clade C HIV IN3 Env and Gag Pol. The salient features of this recombinant virus are:

1. A transient screening marker of green fluorescent protein (GFP) was used in construction of MVA/HIV 71C, so that the GFP is eliminated in the final virus product.

2. The 71C env gene is inserted into del II of MVA genome and the 71C gag pol is inserted in del III.

3. Both env and gag pol of MVA 71C are controlled by vaccinia m-H5 promoter.

4. The MVA virus used to make the recombinant MVA/HIV 71C is MVA 1974/NIH Clone 1.

Plasmid Transfer Vectors

Figure 35:
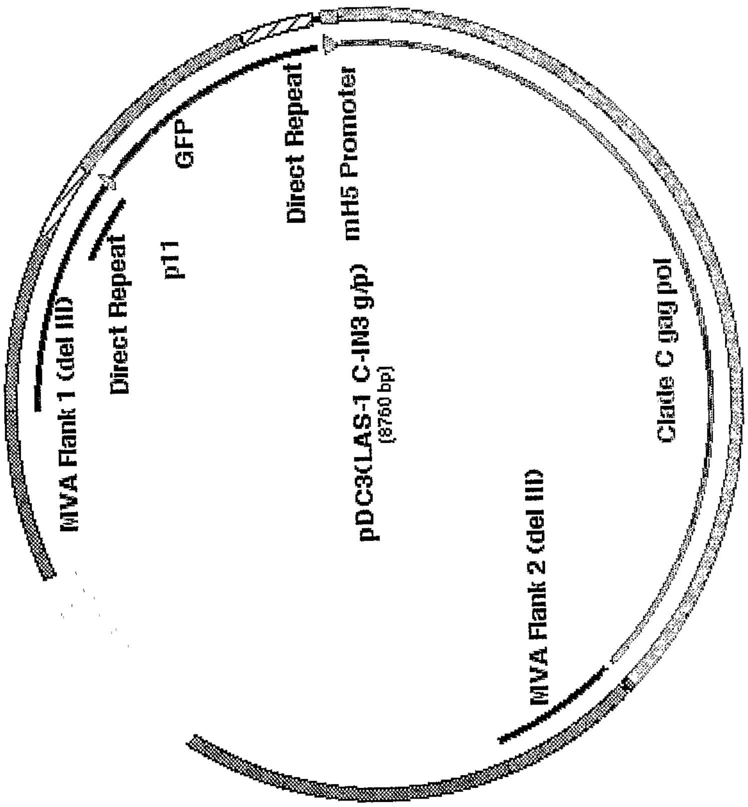
FIG. 35. pDC-3 (LAS-1 C-IN3 gag pol) plasmid.
Figure 36:
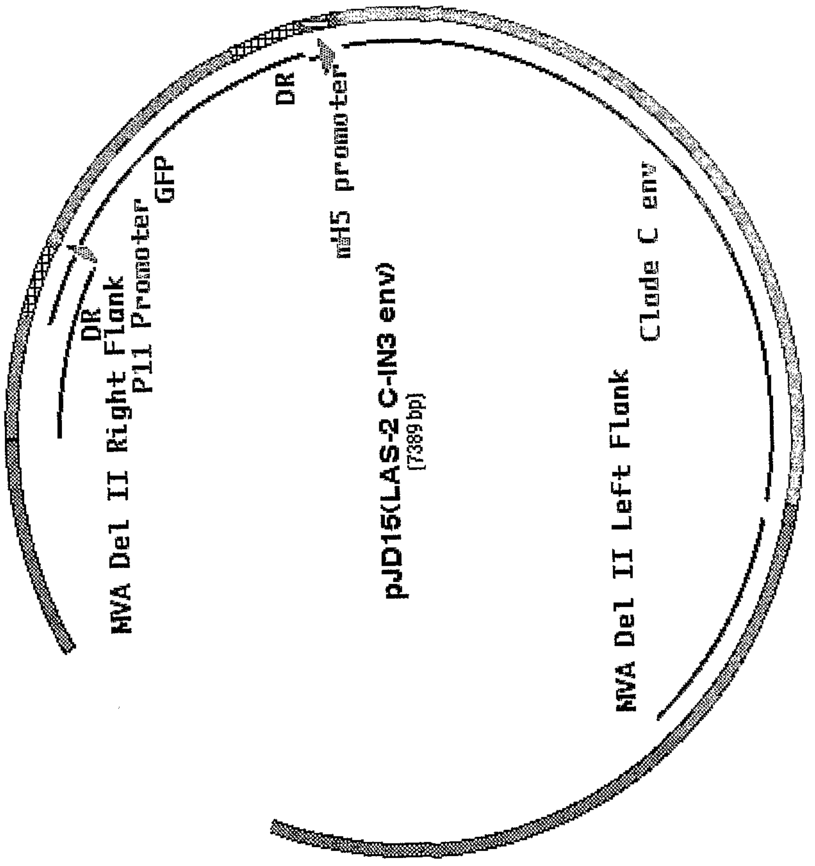
FIG. 36. pJD-15 (LAS-2 C-IN3 env) plasmid.

The plasmid transfer vectors, pDC3 and pJD15, FIG. 35 and FIG. 36 respectively, were used to make the double recombinant MVA by homologous recombination. Each of these plasmids carries the GFP marker, flanked on either side by direct repeats to eliminate GFP in the final virus product. The plasmids were constructed as follows:

1. The gene sequence of HIV C IN3 gag pol (from Indian isolate GenBank #AF286231 from Harriet Robinson, Emory University) containing three mutations to inactivate reverse transcriptase activity (corresponding to that given for clade B recombinant) with the integrase removed was cloned into pCR2.1 using FailSafe PCR kit. The gag/pol gene was cloned into MVA deletion III transfer vector pLAS-1 (containing screening marker GFP flanked by two direct repeats to eliminate GFP in the final virus) via SmaI restriction endonuclease site, and gene expression was under control of the early/late modified H5 promotor. Sequence of the HIV C IN3 gag pol gene was confirmed by DNA sequencing, and this construct was designated pDC3 (FIG. 35).

2. The gene sequence of HIV C IN3 env (from Indian isolate GenBank #AF286231 from Harriet Robinson, Emory University) was truncated via PCR removal of 120 amino acids in the cytoplasmic tail of gp41 and cloned into pCR2.1. Silent mutations to eliminate 2 early poxvirus termination 5TNT signals were made (QuikChange Kit, Stratagene). The modified, truncated env gene was cloned into MVA deletion II transfer vector pLAS-2 (containing screening marker GFP flanked by two direct repeats to eliminate GFP in the final virus) in the Not I site followed by removal of the SphI site within the cloning region by cutting sequentially with SalI, then XhoI and ligating the ends to make pJD-15. Gene expression in this plasmid is under control of the early/late modified H5 promotor. Sequence of the HIV C IN3 env gene was confirmed by DNA sequencing, in this construct was designated pJD-15 (FIG. 36).

Single Recombinant Clade C MVA/HIV Gag Pol

1. MVA 1974/NIH Clone 1 virus, which was derived from an MVA received from Anton Mayr (Munich, Germany) at passage 572 from Feb. 22, 1974 by terminally diluting 3 times at the National Institutes of Health, was used for recombination.

2. Secondary CEF made from 10 day old SPAFAS fertile chicken eggs (distributed by B&E Eggs, Stevens, Pa.) in six-well culture plates were infected at an MOI of 0.05 of MVA and transfected with approximately 3.0 μg of pDC3 (FIG. 37).

3. Following a two day incubation at 37° C., the virus was harvested, frozen and thawed 3×, and plated out on CEF plates.

4. At 3 days post-infection, those foci of infections that expressed GFP (indicating that recombination had occurred between the plasmid and the infecting virus) were picked and replated on CEF. Again, those foci that expressed GFP were picked.

5. These 2× plaque-purified GFP-expressing foci were plated out in duplicate CEF plates and two plates were analyzed for GFP fluorescence and for Gag expression with MAb 183-H12-5C (3537) specific for Gag. Individual foci were picked from the duplicate replicate plate of those samples with little or no GFP staining as well as mostly Gag staining foci.

6. These foci were again plated out in duplicate, and analyzed the same way 3 additional times. The resulting recombinant virus expressed Gag Pol proteins but had deleted the GFP gene by recombination of the double repeats. A seed stock was made, first by growing up the final picked plaques in 1 well of 6 well plate, then T-25 flasks, followed by growth in T-150 flasks. This virus, labeled MVA 68C (LAS1 gag pol), was used to make the double recombinant.

Double Recombinant MVA Construction

1. To make the double MVA recombinant expressing both the Env and the Gag Pol proteins, single recombinant MVA virus expressing Gag Pol (MVA 68C), was used to infect CEF cells at a MOI of 0.05, followed by transfection of 1 μg of pJD15, and grown at 37° C. for 2 days and harvested (FIG. 37).

2. At 3 days post-infection, those foci of infections that expressed GFP (indicating that recombination had occurred between the plasmid and the infecting virus) were picked and replated on CEF. Again, those foci that expressed GFP were picked.

3. These 2× plaque-purified GFP-expressing foci were plated out in duplicate CEF plates and two plates were analyzed for GFP fluorescence and for Env expression with T-43 mAb specific for Env protein. Individual foci were picked from the duplicate replicate plate of those samples with little or no GFP fluorescence as well as mostly Env staining foci.

4. These foci were again plated out in duplicate, and analyzed the same way 4 additional times. The resulting double recombinant virus expressed Env and Gag Pol proteins but had deleted the GFP gene by recombination of the double repeats. An LVD seed stock was made, first by growing up the final picked plaques in 1 well of 6 well plate, then T-25 flask, followed by growth in T-150 flasks. This virus, labeled MVA/HIV 71C (lab. name-Clone 2 C4 6.21121), expressed both Env and Gag by immunostaining.

Characterization of MVA Double Recombinant Virus, MVA/HIV 71C

Figure 38:
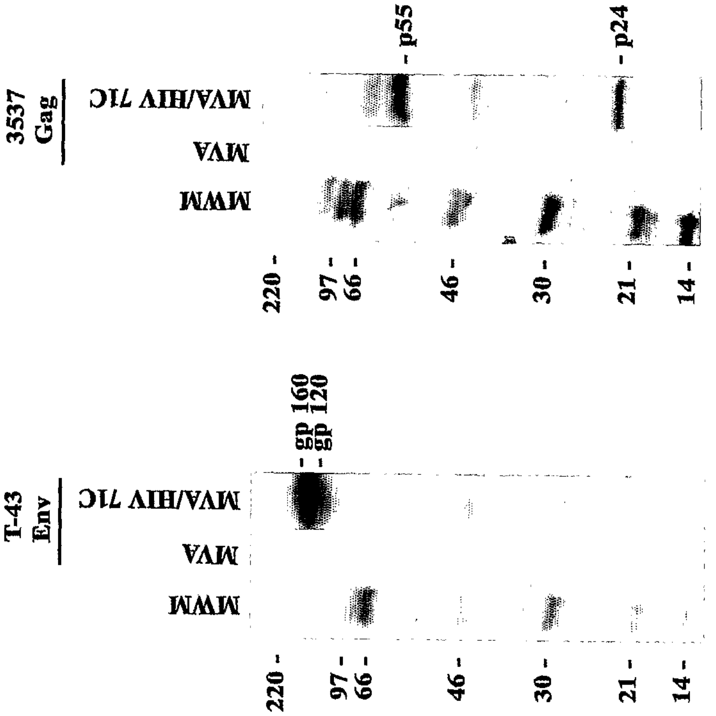
FIG. 38. MVA 71C expression of HIV Env and Gag Pol.

1. Aliquots of MVA/HIV 71C infected BS-C-1 cell lysates were analyzed by radioimmunoprecipitation (RIP) with monoclonal antibodies T-43 and 3537 for expression of Envelope and Gag proteins, respectively (FIG. 38). Bands of the correct size corresponding to each of these proteins were detected. Expression occurred in the presence of Ara-C indicating the functionality of the early part of the mH5 promoter. The recombinant virus was shown to produce gag particles in the supernatant of infected cells by pelleting the $^{35}S$ labeled particles on a 20% sucrose cushion. The functionality of the expressed Clade C envelope had been shown with the identical C sequence in previous constructs in fusion assay.

2. Repeated passage of MVA/HIV 71C and analyzing the resultant virus has confirmed that it is relatively stable through 9 passages of the LVD Seed stock.

3. Sequencing a region of the MVA/HIV 71C genome consisting of the HIV inserts as well as a 1000 base pair region of the MVA genome flanking either sides of the HIV inserts confirms that the GFP genes have been deleted and the sequence of the HIV inserted genes are correct which include the three mutations in the reverse transcriptase gene. FIGS. 39 and 40 show the sequence of the env and gag pol genes in the plasmids.

4. The immunogenicity of a dose $10^7$ pfu of purified MVA/HIV 71C inoculated into mice at 0 and 4 weeks by the intramuscular route has been assessed. ELISA serum antibodies were assayed in a capture ELISA utilizing gp140 clade C env as the antigen. Table 6 shows that the clade C env is immunogenic.

Summary

In summary, we have made a recombinant MVA virus, MVA/HIV 71C, which expresses the Clade C IN3 modified, truncated envelope and mutated gag pol. The MVA double recombinant virus was made by homologous recombination of single MVA recombinant expressing Gag Pol protein, with a plasmid expressing clade C Env. This double MVA recombinant was made using transiently expressed GFP marker that was deleted in the final virus. RIP experiments showed expression of MVA/HIV 71C Env and Gag Pol proteins, as well as production of gag particles. The double recombinant was shown to be relatively stable through repeated passage of the LVD Seed Stock. Immunogenicity experiments in mice show the clade C env to be immunogenic (see Table 6).

TABLE 6

Clade C Env ELISA[a] antibody titers in $10^7$ recombinant MVA immunized mice.

| Virus | Mouse # | Pre-bleed | 2x Immunized[b] |
|---|---|---|---|
| MVA 71C | 276 | <800 | 600,000[c] |
| (Clone #2 C4 6.21121) | 277 | <800 | 800,000 |
| | 278 | <800 | 1,200,000 |
| | 279 | <800 | 1,600,000 |
| | 280 | <800 | 1,600,000 |
| MVA 71C | 281 | <800 | 800,000 |
| (Clone #5 C4 2.21321) | 282 | <800 | 400,000 |
| | 283 | <800 | 800,000 |
| | 284 | <800 | 3,200,000 |
| | 285 | <800 | 3,200,000 |

[a]capture ELISA utilizing gp140 clade C env as antigen;
[b]immunize 5 mice each with 107 dose given IM at 0 and 4 weeks. Bled at 2 weeks post $2^{nd}$ immunization;
[c]reciprocal end point dilution.

EXAMPLE 5

Comparative Immunogenicity in Rhesus Monkeys of Multi-Protein HIV-1 (CRF02_AG) DNA/MVA Vaccines Expressing Mature and Immature VLPs We developed an AIDS vaccine for Western and West-Central Africa founded on HIV-1 subtype CRF02_AG. Rhesus macaques were primed with Gag-Pol-Env-expressing plasmid DNA and boosted with a recombinant modified vaccinia virus Ankara (rMVA), expressing matched proteins. Two DNA vaccine constructs (IC1-90 and IC48) that differed by point mutations in gag and pol were compared. IC1-90 produces primarily immature (core comprises unprocessed Pr55Gag) HIV-like particles (VLPs) and IC48 produces mature VLP with processed Pr55Gag, immature VLP, and intracellular protein aggregates. Both vaccines raised significant cellular responses for Gag, Pol, and Env. Approximate twofold higher ELISPOT responses to Gag and Env epitopes were observed for IC48 animals than for IC1-90 animals at the peak post-MVA effector (P=0.028) and late memory (P=0.051) phases, respectively. Greater breadth for IC48-primed animals was observed than for IC1-90-primed animals at peak response (P=0.03). Our results indicated that the vaccines elicited high frequency T cell responses and primed anti-Env antibody. They also suggest that expression of different forms of VLP has a significant effect on elicited cellular and humoral immunity.

Results

Vaccine Immunogens

To assess the assembly of VLPs, transfection culture supernatants were banded through a sucrose gradient and subsequent fractions were examined for the presence of Gag. Peak VLP fractions were analyzed by immunoblotting using rabbit polyclonal anti-p24 antibody (FIG. 41A). Only two Gag polyproteins, p55 and p41, were detected for IC1-90. Three forms of Gag (p55, p41, and p24) were observed for IC48. The presence of Gag p24 indicates cleavage of the Gag polyprotein. As previously demonstrated, complete inhibition of HIV protease activity by saquinavir (HIV-1 protease inhibitor) or vaccine construct IC25 (genetic modification of protease activity) results in the Gag protein being primarily p55, indicating no cleavage of the Gag polyprotein (Ellenberger, D. et al. 2004 *Virology* 319:118-130). A summary of the vaccine constructs with corresponding protease mutations which result in the production of assorted products, including HIV protein aggregates and VLPs containing complete to partial cleavage of Gag, is shown in FIG. 41B.

To confirm partial inhibition of protease activity permitted VLP assembly and possible particle maturation, cells transfected with protease-mutant vaccine constructs were examined by electron microscopy (FIG. 41C). For IC1-90, immature VLPs were seen (FIG. 41C). These particles were uniformly sized, abundant in number, and similar in appearance (electron-dense shells and lucent centers) to those formed by expression in the presence of saquinavir and IC25 (Ellenberger, D. et al. 2004 *Virology* 319:118-130). Budding structures and numerous VLPs were also observed for IC48 (FIG. 41C). However, two distinctive particle morphologies were observed: VLPs with a spherical protein shell (immature) and other particles with electron dense centers (mature). Furthermore, the VLP with electron-dense centers had a lean spherical protein shell, suggesting cleavage of Gag p55 and condensing of the viral core, comparable to mature HIV particles. IC48-transfected cells were also observed to contain intracellular aggregates of HIV proteins (FIG. 41C).

Total Gag expression was detected by antigen-capture ELISA following 293T cell transfection; IC1-90 expression appeared sharply diminished as compared with IC48, 131, and 878 ng/ml, respectively. In the supernatant and cell lysate, Gag protein levels were 77 and 54 ng/ml (IC1-90) and 624 and 254 ng/ml (IC48), respectively. However, as previously reported (Schneider, R. et al. 1997 *J. Virol.* 71:4892-4903), the detection efficiency of Gag p55 was substantially less than that of Gag p24. Therefore, quantification of total Gag protein of transfection supernatants by Western blot analysis as measured by phosphorimager demonstrated that IC1-90 expressed Gag protein to a level similar to IC48, 1771, and 1570 relative units. For IC1-90, the Gag protein was primarily p55 (61% of the immunoreactive protein). Production of Env protein was also detected by ELISA, and IC1-90 and IC48 Env levels were similar, 696 and 665 ng/ml, respectively. A greater percentage of total Env protein was detected in the supernatant for both constructs.

Preclinical Safety Testing

Three DNA primes at 0, 8, and 26 weeks and a single rMVA booster at 41 weeks were administered in 1 ml by IM needle injections. DNA priming was 0.6 mg of either IC1-90 or IC48 per injection and MVA booster was at $1\times10^8$ pfu. All 16 macaques received identical aliquots only differing by the priming agent, IC1-90, or IC48. Physical examinations, daily observations, measuring for weight, hematology, and clinical chemistry were completed. No local redness or indurations at the injection site were observed.

ELISPOT Analysis

Figure 42:
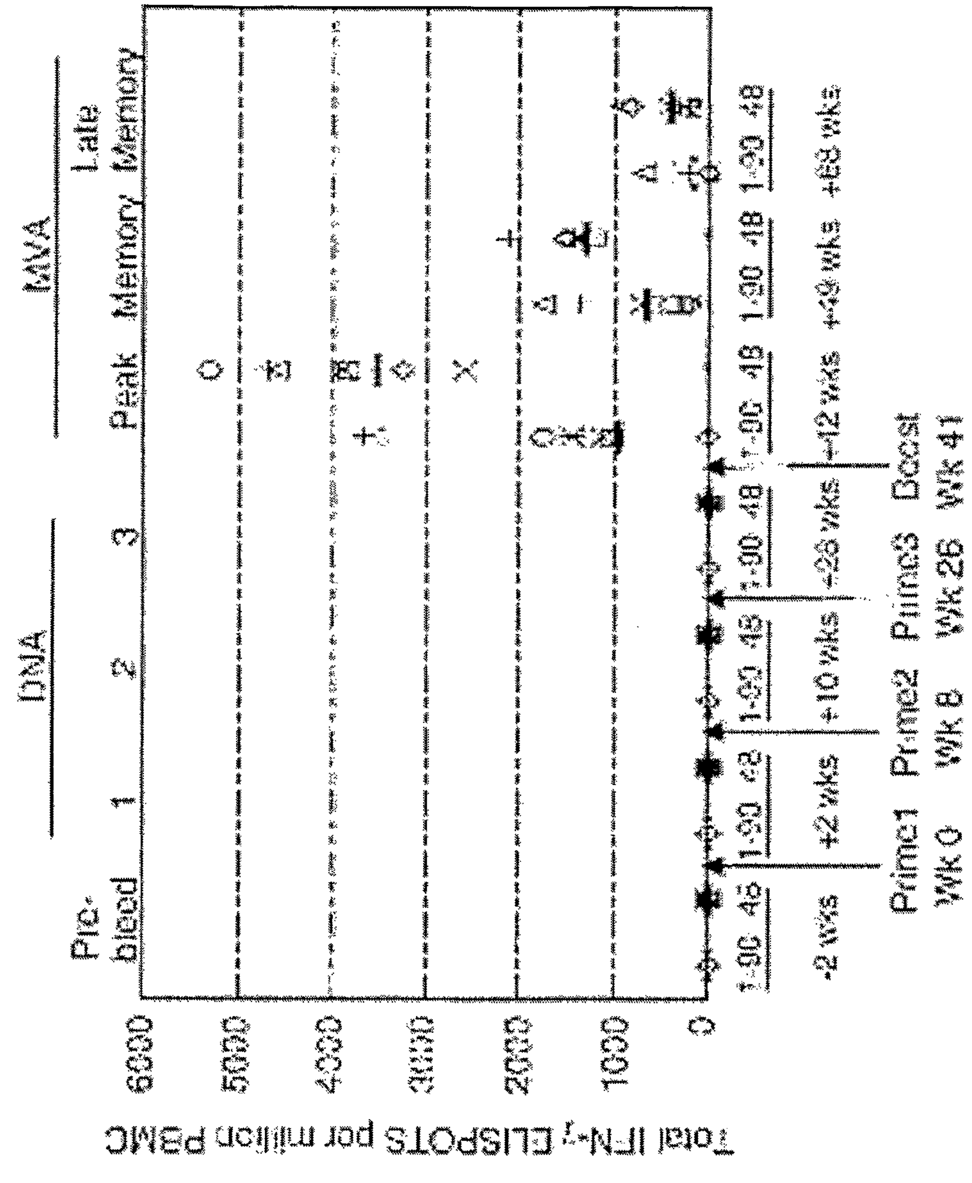
FIG. 42. Temporal IFN-γ ELISPOT responses for pGA1/IC1-90- and pGA1/IC48 DNA-primed groups. Sixteen animals were tested against 19 peptide pools. Symbols designate the total ELISPOT response of each individual animal. The bold bar represents the arithmetic mean of each designated group. Peak ELISPOT response (+42 weeks; 1 week after the MVA booster), memory response (8 weeks after MVA), and late memory (26 weeks after MVA) are indicated. The background value (2× average of negative control plus 10) was subtracted from the raw counts of the peptide wells before conversion to 1 million PBMC.

Vaccine-elicited T cells expanded rapidly after the MVA booster (FIG. 42). Prior to the MVA booster, HIV-1-specific ELISPOT responses were at, or below, our background for detection following each of the DNA primes. Temporal ELISPOT analyses revealed that the highest ELISPOT response was 1 week after the MVA booster (Peak). Frequencies up to 5300 spots per one million peripheral blood mononuclear cells (PBMC) were found at the peak response. This peak of specific cells underwent a threefold contraction into the DNA/MVA memory pool (8 weeks post-MVA). T cell responses contracted an additional threefold at 26 weeks post-peak (late memory). Regardless of the immune phase (peak, memory, or late-memory) total ELISPOTS were greater for IC48-primed animals than IC1-90-primed animals; the T cell responses for IC48 animals were 2.2-fold greater (arithmetic mean) than IC1-90 animals. A random effects model using a linear regression of the aggregate ELISPOT values on group and time demonstrates that IC48 is higher than IC1-90, group effect has P value=0.002 in the model. Furthermore, at peak response (P=0.028) and late memory (P=0.051), significantly higher responses by IC-48-primed animals were observed.

Figure 43:
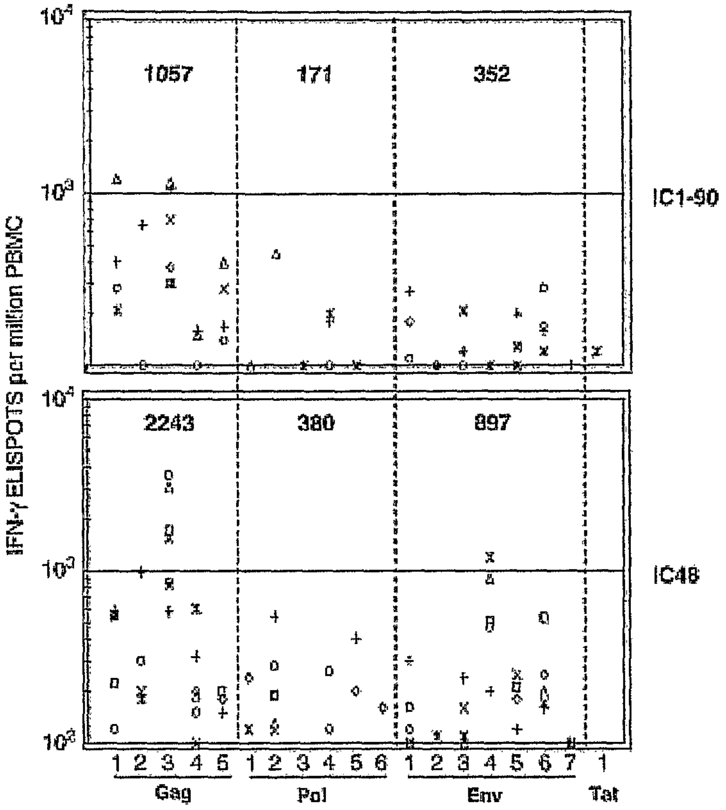
FIG. 43. IFN-γ ELISPOT responses at 1 week after the MVA booster. Numbers indicate the arithmetic means for the response to the indicated gene region. Designations below the panels indicate the gene and peptide pool used for stimulation. Designations to the right of the panels indicate the DNA prime group. Symbols indicate the individual animals. The background value was subtracted before conversion to 1 million PBMC.

At the peak response, both of tested plasmid DNAs successfully primed the MVA booster for an anti-viral IFN-γ ELISPOT response to Gag, Pol, and Env sequences. The analyses revealed greater than twofold differences between the IC48 and IC1-90 primes (FIG. 43). The twofold difference was significant and observed in all tested gene regions of the virus, including Gag (P=0.015), Pol (P=0.047), and Env (P=0.0003). For Pol and Env, the total ELISPOT mean responses were less than the response observed in Gag, but the twofold difference is evident. The limited Tat response was expected as Tat was not a common immunogen in the recombinant plasmid and rMVA.

Figure 44:
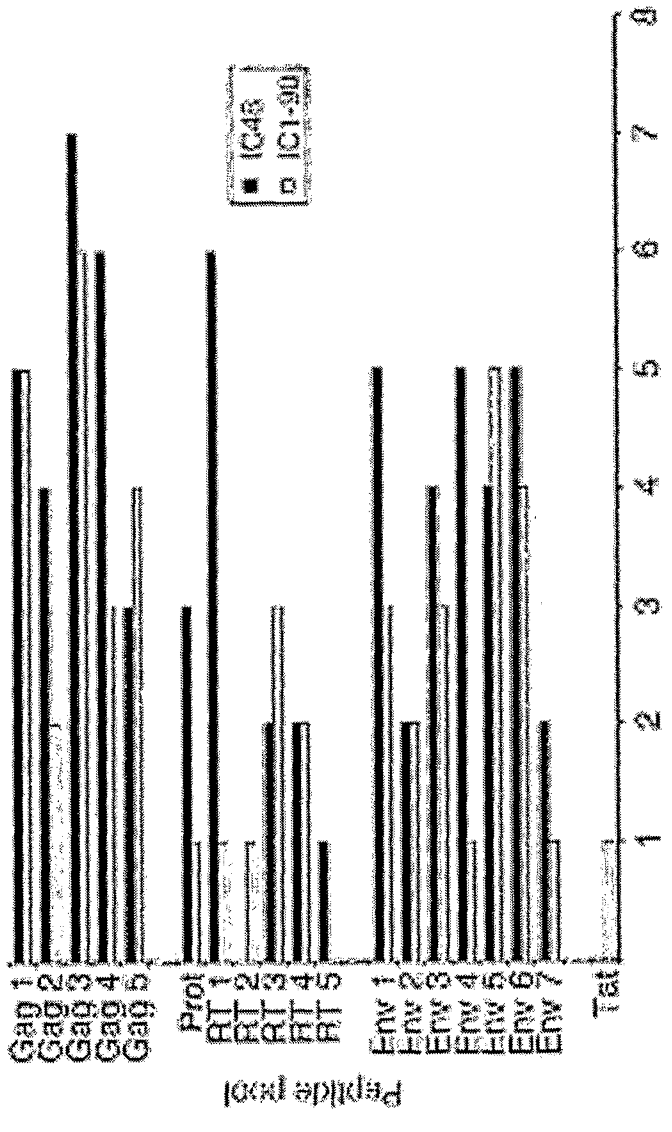
FIG. 44. Breadth of peak ELISPOT responses for IC1-90- and IC48-primed groups. Eight animals per vaccine group were tested against 19 peptide pools (5 Gag, 6 Pol, and 7

A broad ELISPOT response for both Gag and Env was present 1 week after the MVA booster (FIG. 44). Greater breadth of response to peptide pools for IC48-primed animals was observed than IC1-90-primed animals (P=0.03). At the peak response, each of the 5 pools of Gag peptides and 7 pools of Env peptides was recognized by at least 3 of the immunized animals. On average per animal, 2.8 Gag and 2.9 Env peptide pools stimulated a cellular response as measured by ELISPOT. Much lower frequencies of responses were elicited for PR, RT, and Tat, but these pools were recognized by at least one or more of the animals. Four of the 16 animals recognized the one pool of PR peptides, 7 recognized one of the 5 pools of RT peptides, and one animal's cells were stimulated by the pool of Tat peptides.

Consistent with the height of the ELISPOT response, T cells from IC48-primed animals recognized more peptide pools than observed with IC1-90-primed animals (Table 7). In the IC1-90 group, 6 of 8 animals responded to at least one Gag pool with an overall average of 2.5 of 5 pools being recognized (Table 7, FIG. 44). For the IC48 group, 7 of 8 animals responded to at least two Gag pools with an overall average of 3.1 pools being recognized. The Env response was similar in the IC48 group where 7 of 8 animals responded to at least two pools. In the IC1-90 group, only 6 of 8 animals responded to Env, recognizing at least one Env pool. In the memory phase of the immune response, less peptide pools stimulated T cell responses in all the vaccinated animals, but IC48 animals responded to more peptide pools than the IC1-90 group (5.3 vs. 3 pools), respectively.

TABLE 7

Average number of peptide pools per animal recorded as positive by ELISPOT and intracellular cytokine staining analysis

| Pep- | ELISPOT[a] | | | | Intracellular cytokine staining[b] | | | |
|---|---|---|---|---|---|---|---|---|
| tide | Peak[c] | | Memory[d] | | CD8 | | CD4 | |
| pool[e] | IC1-90 | IC48 | IC1-90 | IC48 | IC1-90 | IC48 | IC1-90 | IC48 |
| Gag | 2.5 | 3.1 | 2.1 | 2.5 | 1.1 | 1.25 | 2.9 | 3.0 |
| Pol | 1 | 1.8 | 0 | 0.5 | ND[f] | ND | ND | ND |
| Env | 2.4 | 3.4 | 0.9 | 2.3 | 0.75 | 1.25 | 3.0 | 3.6 |
| Total | 6 | 8.3 | 3 | 5.3 | 1.9[g] | 2.5[g] | 5.9[h] | 6.6[h] |

[a]ELISPOT counts of twice the background (>100) were considered positive.
[b]Combination of IFN-γ and IL-2 expression.
[c]One week after MVA booster.
[d]Eight weeks after MVA booster.
[e]Gag, 5 pools; Pol, 6 pools (includes protease pool); Env, 7 pools.
[f]ND, not done.
[g]Average CD8+ cell response per animal, 2.2 pools.
[h]Average CD4+ cell response per animal, 6.25 pools.

A broad response for both Gag and Env was retained 8 weeks post-MVA booster (FIG. 45). In the memory phase, IC48-primed animals responded to more epitopes (P=0.004) than IC1-90-primed animals. Frequencies up to 2125 spots per million PBMC were found at the memory phase. Fifteen of the 16 animals recognized at least one pool of peptides. Monkeys AC36 and M509, initially nonresponders at 1-week post-MVA, were shown to recognize at least one Gag pool at 8 weeks post-MVA. Animal O2L remained nonresponsive to the peptide pools. At the memory response, each of the 5 pools of Gag peptides and 5 of 7 Env peptide pools were recognized by at least one of the immunized animals.

Intracellular Cytokine Analysis

To determine the frequencies of responding CD4 and CD8 T cells, intracellular cytokine assays were performed (FIG. 46). Peptide induction of IFN-γ and IL-2 expression in CD4 and CD8 lymphocytes was measured, and both tested plasmid DNAs successfully primed the MVA booster. One week following the MVA booster, peak responses were observed as seen by ELISPOT analyses. Regardless of the gene region, the response by IC48-primed animals was significantly greater than IC1-90-primed animals: Env (P=0.006) and Gag (P=0.026). CD8 cells specific for Gag epitopes expanded to frequencies as high as 2.6% of total CD8 T cells in one animal. Intracellular cytokine staining for IFN-γ expression and IL-2 revealed an approximate fourfold difference to Gag peptides between the DNA plasmids; IC48 primed more CD8 cells than IC1-90. The geometric mean of percent-specific CD8 cells was 0.54 vs. 0.14 for the IC48 group and IC1-90 group, respectively. A twofold difference was detected in the Env region (0.28 vs. 0.14). The same ratios were observed regardless of the expressed cytokine.

In several animals, CD4 cells specific for Gag epitopes expanded to frequencies as high as 0.5% of the total CD4 T cells (FIG. 46). Statistical analyses revealed that a significantly greater number of CD4 cells specific for Env epitopes were observed for the IC48-primed animals than IC1-90 animals (P=0.006). However, staining for IFN-γ expression and IL-2 revealed a fourfold difference (0.39 vs. 0.11 geometric means) to Env peptides and twofold difference (0.31 vs. 0.15) for Gag peptides between the DNA plasmids. Overall, CD4 cell responses were significantly greater than CD8 cell responses (P<0.0001).

Based on FIG. 46 data, geometric means were determined to compare specific cells (CD4 and CD8), cytokines expressed (IFN-γ and IL-2), and HIV gene regions. Peptide induction of IL-2 expression in CD4 lymphocytes was twofold greater than the percent-specific CD8 lymphocytes (0.113 vs. 0.056 geometric mean). However, CD8 and CD4 cells were similar for IFN-γ expression (0.089 vs. 0.078 geometric mean). In the Gag region, IFN-γ expression was significantly greater than IL-2 expression (P=0.013), but CD4-IL2, CD8-IL2, and CD8-IFN-γ expressions were significantly greater than CD4-IFN (P=0.032).

The average number of peptide pools recorded as positive by intracellular cytokine staining to include both IFN-γ and IL-2 expression were found to be relatively comparable between DNA priming groups regardless of the gene region (Table 7). At the peak immune response, IC1-90 animals would require a 31% and 11% increase in peptide pool responses to equal the response of IC48 animals for CD8 and CD4 cells, respectively. However, threefold more peptide pools induced IFN-γ and IL-2 expression in CD4 cells than CD8 cells (6.25 vs. 2.2 pools). This same threefold ratio was observed for both IC1-90- and IC48-primed animals.

Antibody Responses

The antibody response was strongly boosted by the MVA. By Western blot analysis, negligible binding antibody was elicited by DNA priming, but 11 of 16 animals (6 IC1-90 and 5 IC48 monkeys) showed Env reactivity against an HIV-1 subtype AG virus lysate 3 weeks following the MVA. All 11 reactive animals produced antibody which detected Env gp120 and only one animal responded to Gag p24. There was no difference between the two groups of primed animals.

Anti-Env titers were determined for the vaccinated animals by solid-phase Env ELISA. At 3 weeks post-MVA, the average reciprocal titers were 1075(±1569) and 2119 (±1898) for the IC1-90- and IC48-primed animals, respectively. The titers fell to 953(±979) and 850(±563), respectively, at 8 weeks after the booster. There was no substantial difference observed between the two groups of animals.

Tests for neutralizing antibody revealed very low levels of activity for the primary isolate used for the vaccine; only one animal scored positive. The primary isolate, a recombinant HIV-1 subtype AG, was relatively resistant to neutralization by many other sera and neutralizing monoclonal antibodies. The neutralizing activity of the plasma also did not score for HIV-1-MN (subtype B), a laboratory-adapted isolate against HIV-1.

Materials and Methods

DNA Immunogens

DNA constructs were made in the pGA1 expression vector (GenBank accession no.: AF425297) that includes intron A in the promoter cassette and uses the CMV immediate-early promoter and the bovine growth hormone polyadenylation sequence to express RNAs (Chapman, B. S. et al. 1991 *PNAS USA* 19:3979-3986 and Ross, T. M. et al. 2000 *Nat. Immunol.* 1:127-131). An incident recombinant HIV-1 subtype AG (CRF02_AG) strain IC0928 was reverse transcribed (GenBank accession no.: AY227361 and AY227362), and fragments produced by DNA PCR were cloned into the pGA1 expression vector (Ellenberger, D. L. et al. 2002 *Virology* 302:155-163 and Ellenberger, D. et al. 2004 *Virology* 319:118-130). Construction and description of pGA1/IC48 (IC48) have been previously described (Ellenberger, D. et al 2004 *Virology* 319:118-130). pGA1/IC1-90 (IC1-90) differs from IC48 by point mutations in gag and pol. Briefly, IC1-90 lacks the introduced point mutations in gag NC zinc fingers and pol RT as previously described for IC48 (Ellenberger, D. et al. 2004 *Virology* 319:118-130, Smith, J. M. et al. 2004 *AIDS Res. Hum. Retrovir.* 20:1335-1347 and Smith, J. M. et al. 2004 *AIDS Res. Hum. Retrovir.* 20:654-665). IC1-90 and IC48 also differ in their protease sequence where there are two substitutions in IC1-90, an Arg-to-Gly substitution at position 70 and Met-to-Leu substitution at position 90. IC48 has a Gly-to-Val substitution at position 48 as previously described. The protease mutations were made using a site-directed mutagenesis kit (Stratagene, La Jolla, Calif.) following the manufacturer's protocol. All mutations were confirmed by sequencing.

Recombinant MVA Immunogen

A recombinant MVA expressing gag, pol, and env regions derived from IC0928 is described above. Briefly, it was constructed with gag-pol inserted into deletion III and a truncated env into del II as described previously for MVA/SHIV89.6 (Earl, P. L. et al. 2002 *Virology* 294:270-281) with the modification that a transient GFP marker for obtaining recombinant virus was used, similar to the transient GUS described by Wyatt et al. (Wyatt, L. S. et al. 2004 *AIDS Res. Hum. Retrovir.* 20:645-653).

Cell Line and Transient Transfections

Human 293T cells, a human kidney-derived cell line, were maintained in Dulbecco's modified Eagle medium (DMEM) supplemented with 10% fetal bovine serum. 293T cells were added at $10^6$ cells/well of Costar 6-well plates in 2 ml of DMEM growth medium and incubated for 24 h at 37° C. in a 5% $CO_2$ humidified atmosphere. After 24 h, LipofectAmine2000 reagent (Invitrogen, Carlsbad, Calif.) and plasmid DNA were mixed according to the manufacturer's protocol and added to each well. Supernatants were harvested 24 or 48 h following the addition of transfection reagents.

Purification of Particles

Following 24 h of transient transfection of 293T cells, culture supernatants were recovered, clarified by centrifugation at 200×g for 5 min, and 1 ml was layered on top of 10-50% sucrose gradients. Gradients of 10 ml consisting of 2 ml each of 50%, 40%, 30%, 20%, and 10% sucrose solutions were added to ultraclear centrifuge tubes from bottom to top. Gradients were centrifuged at 40,000 rpm for 16 h in SW41Ti rotor. Fractions of 1 ml were recovered, top to bottom. Fraction aliquots were analyzed by HIV-1 p24-antigen-capture assay.

Electron Microscopy

Transfected 293T cells were fixed in the multi-well plate using 1 ml of 2.5% glutaraldehyde in 0.1 M cacodylate buffer for 2 h at 4° C. After three washes with the same buffer, 1.0% osmium tetroxide in 0.1 M cacodylate buffer was added, incubated for 1 h, dehydrated through an ethanol series, and embedded with Eponate 12 resin. Following polymerization of the resin, the cells were sectioned en face, stained with 4% uranyl acetate in water and lead citrate, and observed on a Hitachi H-7500 transmission electron microscope.

Antigen-Capture Assay

Assay was performed using an HIV-1 antigen-capture EIA kit (Coulter, Hialeah, Fla.) according to the manufacturer's instructions.

Env ELISA

Pooled human immunoglobulin anti-HIV (catalog no. 3957) was obtained from the National Institute of Allergy and Infectious Diseases AIDS Research and Reference Reagent Program (Rockville, Md.). Env ELISA was done as previously described (Ellenberger, D. et al. 2004 *Virology* 319:118-130).

Macaques and Immunogenicity Trial

Sixteen young adult male outbred rhesus macaques (*Macaca mulatta*) of Indian origin were randomized by weight into two vaccine groups of 8. The IC1-90 group received 0.6 mg of IC1-90 DNA and the IC48 group received 0.6 mg of IC48 DNA intramuscularly (IM) at weeks 0, 8, and 26. DNA immunizations were delivered in phosphate-buffered saline with a needle and syringe. A total of 3 injections were delivered to the upper lateral right thigh in a volume of 1 ml/injection. Fifteen weeks following the 3rd DNA immunization (week 41), all animals received $1\times10^8$ pfu of a modified vaccinia Ankara virus (MVA/HIV) booster IM using a needle and syringe in the upper lateral right thigh. The MVA immunization was delivered in phosphate-buffered saline in a volume of 1 ml. Injection sites were monitored for local inflammatory reactions.

Humoral Responses

Western blot analysis of whole virus lysate and sucrose-purified VLP was performed as previously described (Sambrook, J. et al. 1989 Molecular Cloning: A Laboratory Manual (2nd ed.), Cold Spring Harbor Laboratory Press, Cold Spring Harbor, N.Y.). Whole virus lysate (IC0928) was run on 4-15% gradient SDS gel and transferred to nitrocellulose. Plasma samples were diluted 1:100 in blocking buffer. The secondary antibody was anti-human IgG (Fab)-phosphatase and detection was completed by using the BCIP/NBT phosphatase substrate system (KPL, Gaithersburg, Md.) according to manufacturer's instructions. Analysis of sucrose-purified VLP was completed using rabbit polyclonal anti-p24 (catalog no. 4250) which was obtained from the National Institute of Allergy and infectious Diseases AIDS Research and Reference Reagent Program. HIV-1 Gag protein bands were visualized using the ECL Western blotting detection reagent (Amersham Pharmacia Biotech, Piscataway, N.J.) as described by the manufacturer. Expression levels were determined using a phosphoimager.

To measure the levels of Env IgG in sera of immunized monkeys, 96-well U-bottom plates were coated with sheep antibody to the C-terminus of gp120 followed by purified CRF02_AG gp140 as previously described (Earl, P. L. et al. 2002 *Virology* 294:270-281). The time of incubation of serum dilutions was increased from 2 h to overnight for enhanced sensitivity of the ELISA.

Neutralization was measured as a function of reductions in luciferase reporter gene expression after a single round of infection in TZM-b1 cells. TZM-b1 cells were obtained from the NIH AIDS Research and Reference Reagent Program, as contributed by John Kappes and Xiaoyun Wu. Briefly, 200 TCID50 of virus was incubated with serial threefold dilutions of serum sample in triplicate in a total volume of 150 μL for 1 h at 37° C. in 96-well flat-bottom culture plates. Freshly trypsinized cells (10,000 cells in 100 μl of growth medium containing 75 μg/ml DEAE dextran) were added to each well. Indinavir was added at a final concentration of 1 μM to prevent replication in the case of HIV-1 MN. One set of control wells received cells+virus (virus control) and another set received cells only (background control). After a 48-h incubation, 100 μl of cells was transferred to a 96-well black solid plates (Costar) for measurements of luminescence using Bright Glo substrate solution as described by the supplier (Promega). An assay stock of virus pseudotyped with gp160 from the CRF02_AG vaccine strain was prepared by transfection in 293T cells and titrated in TZM-b1 cells. The assay stock of HIV-1 MN was prepared in H9 cells.

Peptide Pools

HIV-1 recombinant subtype CRF02_AG peptides were 15mers overlapping by 11 derived from the vaccine strain. Peptides were assembled into pools containing approximately 25 peptides. Peptides were dissolved in DMSO at 50-100 mg/ml and stock solutions maintained at −70° C. Peptide working solutions were kept at −20° C. for 1 week.

T Cell Assays

ELISPOT assays were done as previously described (Amara et al., 2001 and Amara et al., 2002), except that 2 μg/ml of antibody to human CD28 and CD49d (Becton Dickinson, San Jose, Calif.) was included in incubations (Waldrop, S. L. et al. 1998 *J. Immunol.* 161:5284-5295). Purified PBMC were plated in duplicate in 96-well plates at $2\times10^5$ cells/well with peptide pools used at a final concentration of 10 μg/ml for each peptide. Four wells received only media. Plates were incubated at 37° C., 5% $CO_2$ for 36 h, and spots counted using an ELISPOT reader. Background was set at 2× the average of the negative control wells plus 10. This background value was subtracted from the raw counts of the peptide wells before conversion to 1 million PBMC. Only ELISPOT counts of twice the background (>100) were considered significant.

Intracellular cytokine (ICC) staining assays for IFN-γ and IL-2 have been described previously (Amara, R. R. et al. 2001 *Science* 292:69-74 and Amara, R. R. et al. 2002 *J. Virol.* 76:6138-6146). For those assays, one million PBMC were resuspended in 100 μl of RPMI in a 5-ml polypropylene tube and stimulated with 100 μg/ml of the peptide pool in the presence of anti-CD28 and anti-CD49d antibody at a final concentration of 1 μg/ml. The cells were incubated at 37° C., in a tissue culture incubator at an angle of 5° in 100 μl. At 2 h, 900 μl of medium with 10 μg of Brefeldin A was added and the incubation continued for an additional 4 h. Cells were then stained for CD3, CD8, CD69, IFN-γ, and IL-2 fixed with 1% formaldehyde in PBS, and acquired within 24 h on a FACScaliber (Becton Dickinson, San Jose, Calif.). Approximately 150,000 lymphocytes were acquired for each sample. Data were analyzed using FloJo software (Tree Star, Inc., San Carlos, Calif.).

Statistical Analysis

The Wilcoxon test for independent samples and signed-rank test were used for comparison of immunogenicity tests from groups primed with the two DNA vaccines. A mixed-effects model using a linear regression of the aggregate ELISPOT values on group (IC-48 or IC1-90) and time with monkeys as the random effect was used. Also, a mixed-effects linear regression model was used for testing responses of CD4 versus CD8 T cells, T cell responses against Gag versus Env, and IFN-γ and IL-2 expression.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referenced to above, are hereby incorporated by reference.

What is claimed is:

1. A pharmaceutical composition comprising a recombinant MVA virus comprising a sequence encoding an HIV Env antigen inserted into deletion site II of an MVA and a sequence encoding HIV Gag and Pol antigens inserted into deletion site III of the MVA genome, and a pharmaceutically acceptable carrier;

wherein the sequence encoding the HIV Env antigen comprises SEQ ID NO:3 and the sequence encoding the HIV Gag and Pol antigens comprises SEQ ID NO: 4;

wherein the transcription of the sequence encoding the HIV Env antigen is under the control of a first promoter and transcription of the sequence encoding the HIV Gag and Pol antigens is under the control of a second promoter and wherein the noncoding sequence between the first promoter and the initiation codon of the sequence encoding the HIV Env antigen comprises SEQ ID NO:8.

2. A recombinant MVA virus comprising a sequence encoding an HIV Env antigen inserted into deletion site II of an MVA and a sequence encoding HIV Gag and Pol antigens inserted into deletion site III of the MVA;

wherein the sequence encoding the HIV Env antigen consists of SEQ ID NO:3 and the sequence encoding the HIV Gag and Pol antigens comprises SEQ ID NO: 4;

wherein the transcription of the sequence encoding the HIV Env antigen is under the control of a first promoter and transcription of the sequence encoding the HIV Gag and Pol antigens is under the control of a second promoter and wherein the non-coding sequence between the first promoter and the initiation codon of the sequence encoding the HIV Env antigen comprises SEQ ID NO:8.

3. A recombinant MVA virus comprising a sequence encoding an HIV Env antigen inserted into deletion site II of the MVA and a sequence encoding HIV Gag and Pol antigens inserted into deletion site III of the MVA;

wherein the sequence encoding the HIV Env antigen comprises SEQ ID NO:3 and the sequence encoding the HIV Gag and Pol antigens comprises SEQ ID NO: 4;

wherein the transcription of the sequence encoding the HIV Env antigen is under the control of a first promoter and transcription of the sequence encoding the HIV Gag and Pol antigens is under the control of a second promoter and wherein the sequence between the first promoter and the initiation codon of the sequence encoding the HIV Env antigen comprises SEQ ID NO:8.

4. A recombinant MVA virus comprising a sequence encoding an HIV Env antigen inserted into deletion site II of the MVA and a sequence encoding HIV Gag and Pol antigens inserted into deletion site III of the MVA;

wherein the sequence encoding the HIV Env antigen consists of SEQ ID NO:3 and the sequence encoding the HIV Gag and Pol antigens consists of SEQ ID NO: 4;

wherein the transcription of the sequence encoding the HIV Env antigen is under the control of a first promoter and transcription of the sequence encoding the HIV Gag and Pol antigens is under the control of a second promoter and wherein the sequence between the first promoter and the initiation codon of the sequence encoding the HIV Env antigen comprises SEQ ID NO:8.

5. The pharmaceutical composition of claim 1 wherein the composition is formulated for intravenous, cutaneous or subcutaneous, nasal, intramuscular, intraperitoneal, intradermal, or mucosal routes.

6. The pharmaceutical composition of claim 1 wherein the composition further comprises at least one pharmaceutically acceptable excipient, carrier, buffer, and/or stabilizer.

7. The pharmaceutical composition of claim 6 wherein the composition further comprises physiological saline solution, dextrose or other saccharide solution or glycols such as ethylene glycol, propylene glycol or polyethylene glycol.

8. The recombinant MVA virus of any of claims 1, 2 and 3-4 constructed from MVA 1974/NIH Clone 1.

9. The recombinant MVA virus of any of claims 1, 2 and 3-4 wherein both the first promoter and the second promoter comprise the mH5 promoter.

10. A method of boosting a $CD8^+$ T cell or antibody immune response to an HIV Env, Gag, or Pol antigen in a primate, the method comprising administering to the primate the composition of any of claims 1, 2 and 3-4, whereby a $CD8^+$ T cell or antibody immune response to the antigen previously primed in the primate by previous administration of a nucleic acid molecule encoding a Env, Gag, or Pol antigen is boosted.

11. A method of inducing a $CD8^+$ T cell or antibody immune response to an HIV Env, Gag, or Pol antigen in a primate, the method comprising administering to the primate a priming composition comprising a nucleic acid molecule encoding an HIV Env, Gag, or Pol antigen and then administering to the primate the recombinant MVA of any of claims 1, 2 and 3-4, whereby a $CD8^+$ T cell or antibody immune response to the antigen is induced.

12. The method of claim 10, wherein the primate is a human.

13. The recombinant MVA virus of claim 8 wherein both the first promoter and the second promoter comprise the mH5 promoter.

14. The method of claim 11, wherein the primate is a human.

15. The method of claim 10, wherein the recombinant MVA is administered at a dose of about $10^6$ to $10^9$ infectious virus particles/injection.

16. The method of claim 11, wherein the recombinant MVA is administered at a dose of about $10^6$ to $10^9$ infectious virus particles/injection.

* * * * *

SEQUENCE LISTING

```
<160> NUMBER OF SEQ ID NOS: 17

<210> SEQ ID NO 1
<211> LENGTH: 2220
<212> TYPE: DNA
<213> ORGANISM: Artificial Sequence
<220> FEATURE:
<223> OTHER INFORMATION: MVA 65A/G Env

<400> SEQUENCE: 1

atgagagtga tggggataca gaagaattat ccactcttat ggagaggggg tatgacaata     60

ttttggttaa tgatgatttg taatgctgaa aagttgtggg tcacagtcta ctatggggta    120

cctgtgtgga gagacgcaga gaccacccta ttctgtgcat cagatgctaa agcatatgac    180

aaagaagcac acaatgtctg ggctacgcat gcctgcgtac ccacagaccc tgacccacaa    240

gaattacctt tggtaaatgt aacagaagag tttaacatgt ggaaaaataa tatggtagaa    300

cagatgcatg aagatataat tagtctatgg gaccaaagct taaagccatg tgtacagcta    360

acccctctct gcgttacttt agggtgtgct gacgctcaaa acgtcaccga caccaacacc    420

accatatcta atgaaatgca aggggaaata aaaaactgct ctttcaatat gaccacagaa    480

ttaagagata agaagcagaa agtgtatgca cttttctata gacctgatgt aatagaaatt    540

aataaaacta agattaacaa tagtaatagt agtcagtata tgttaataaa ttgtaatacc    600

tcaaccatta cacagacttg tccaaaggta tcctttgagc caattcccat acattattgt    660

gccccagctg gttttgcaat tctaaagtgt aatgatacgg agttcagtgg aaaagggaca    720

tgcaagagtg tcagcacagt acaatgcaca catggaatca agccagtagt atcaactcaa    780

ctgctgttaa atggcagtct agcagaagga aagatagcga ttagatctga gaatatctca    840

aacaatgcca aaactataat agtacaattg actgagcctg tagaaattaa ttgtatcaga    900

cctggcaaca atacaagaaa aagtgtacgc ataggaccag gacaaacatt ctatgcaaca    960

ggtgacataa taggagatat aagacaagca cactgtaatg ttagtaaaat agcatgggaa   1020

gaaactttac aaaaggtagc tgcacaatta aggaagcact ttcagaatgc cacaataaaa   1080

tttactaaac actcaggagg ggatttagaa attacaacac atagttttaa ttgtggagga   1140

gaattcttct attgcaatac aacaaagctg tttaatagca cttggaataa tgataactca   1200

aacctcacag aggaaaagag aaaggaaaac ataactctcc actgcagaat aaagcaaatt   1260

gtaaatatgt ggcagagagt aggacaagca atatatgccc ctcccatccc aggaaacata   1320

acttgtggat caaacattac tgggctacta ttaacaagag atggagggaa taatggtaca   1380
```

aatgatactg agaccttcag gcctggagga ggagatatga gggacaattg gagaagtgaa 1440
ttatataaat ataaagtagt aaaaattgaa ccactaggtg tagcaccaac ccctgcaaaa 1500
agaagagtgg tggaaagaga aaaaagagca gttggaatgg gagctttgat ctttgagttc 1560
ttaggagcag caggaagcac tatgggcgcg gcgtcaatgg cgctgacggt acaggccaga 1620
caattattgt ctggtatagt gcaacagcag agcaatctgc tgaaggctat agaggctcaa 1680
caacatctgt tgagactcac ggtctggggc attaaacagc tccaggcaag agtcctggct 1740
ctggaaagat acctaaagga tcaacagctc ctaggaattt ggggctgctc tggaaaactc 1800
atttgcacca ctgctgtacc ttggaactct agctggagta ataaaagtta taatgacata 1860
tgggataaca tgacctggct gcaatgggat aaagaaatta acaattacac atacataata 1920
tataatctac ttgaaaaatc gcagaaccag caggaaatta atgaacaaga cttattggca 1980
ttagacaagt gggcaagtct gtggaattgg tttgacataa caagctggct atggtatata 2040
agattaggta taatgatagt aggaggcgta ataggcttaa gaataatttt tgctgtgctt 2100
actatagtga atagagttag gcagggatac tcacctttgt cattccagac ccttgcccac 2160
caccagaggg aacccgacag gcccgaaaga atcgaagaag gaggtggcga gcaagactaa 2220

<210> SEQ ID NO 2
<211> LENGTH: 3473
<212> TYPE: DNA
<213> ORGANISM: Artificial Sequence
<220> FEATURE:
<223> OTHER INFORMATION: MVA 65A/G GagPol

<400> SEQUENCE: 2
atgggtgcga gagcgtcagt gttaacgggg ggaaaattag attcatggga gaaaattagg 60
ttaaggccag ggggaaagaa aagatataga ctaaaacacc tagtatgggc aagcagggag 120
ctggagagat tcgcacttaa ccctggccta ttagaaacag cagaaggatg tcaacaacta 180
atgggacagt tacaaccagc tctcaggaca ggatcagaag agtttaaatc attatataat 240
atagtagcaa ccctttggtg cgtacatcaa agaatagaca taaaagacac ccaggaggcc 300
ttagataaag tagaggaaaa acaaaataag agcaagcaaa aggcacagca ggcagcagct 360
gcaacagccg ccacaggaag cagcagccaa aattacccta tagtgcaaaa tgcacaaggg 420
caaatggtac atcagtccat gtcacctagg actttaaatg catgggtgaa ggtaatagaa 480
gaaaaggctt ttagcccaga ggtaataccc atgttttcag cattatcaga gggagccacc 540
ccacaagatt taaatatgat gctaaacata gtgggggggac accaggcagc aatgcagatg 600
ttaaaagata ccatcaatga tgaagctgca gaatgggaca gagtacatcc agtacatgca 660
gggcctattc caccaggcca aatgagggaa ccaaggggaa gtgacatagc aggaactact 720
agtacccttc aagaacaaat aggatggatg acaagtaatc cacctatccc agtgggagaa 780
atctataaaa gatggatagt cctgggatta aataaaatag taagaatgta tagccctacc 840
agcattttgg acataagaca agggccaaaa gaacccttta gagattatgt agacaggttc 900
tttaaaactt tgagagctga acaagctacg caggaggtaa aaaactggat gacagaaacc 960
ttgttggtcc aaaatgcgaa tccagactgc aagtccattt taagagcatt aggaccaggg 1020
gctacattag aagaaatgat gacatcatgt cagggagtgg gaggacctgg ccataaagca 1080
agggttttgg ctgaggcaat gagtcaagta caacagacca atgtaatgat gcagagaggc 1140
aattttagag gccagagaat aataaagtgt ttcaactgtg gcaaagaagg acacctagcc 1200

-continued

```
agaaattgca aggctcctag aaagagaggc tgttggaaat gtggaaagga aggacaccaa   1260
atgaaagact gtactgaaag acaggctaat tttttaggga aaatttggcc ttcccacaag   1320
gggaggccag gaaattttcc tcagagcaga ccagaaccaa cagccccgcc agcagagagc   1380
tttggagtgg gggaagagat accctcctct ccgaagcagg agccgaggga caagggacta   1440
tatcctccct taacttccct caaatcactc tttggcaacg accagtagtc acagtaagaa   1500
tagggggaca gccaatagaa gccctattag acacaggagc agatgataca gtattagaag   1560
aaataagttt accaggaaaa tggaaaccaa aaatgatagg gggaattgga ggttttatca   1620
aagtaagaca gtatgatcag atatctatag aaatttgtgg aaaaagggcc ataggtacag   1680
tattagtagg acctacacct gtcaacataa ttggacgaaa tatgttgact cagattggtt   1740
gtactttaaa ttttccaatt agtcctattg aaactgtgcc agtaaaatta aagccaggaa   1800
tggatggccc aaaggttaaa caatggccat tgacagaaga aaaaataaaa gcattaaaag   1860
aaatttgtgc agagatggaa aaggaaggaa aaatttcaaa aattgggcct gaaaacccat   1920
acaatactcc aatatttgcc ataaagaaaa aagatagtac taaatggaga aaattagtag   1980
atttcagaga actcaataag agaactcaag acttctggga ggtccaatta ggaatacctc   2040
atcctgcggg attaaaaaag aaaaaatcag taacagtact agatgtgggg gatgcatatt   2100
tttcagttcc cttagatgaa gactttagaa aatatactgc attcaccata cctagtttaa   2160
ataatgagac accagggatt agatatcagt acaatgtact cccacaggga tggaaaggat   2220
caccagcaat atttcaggca agcatgacaa aaatcttaga gccctttaga gcaaaaaatc   2280
cagagatagt gatctaccaa tatatgaacg atttatatgt aggatctgac ttagaaatag   2340
ggcagcatag agcaaaaata gaggagttga gagaacatct attgaaatgg ggatttacca   2400
caccagacaa aaaacatcag aaagaacctc catttctttg gatgggatat gaactccatc   2460
ctgacaaatg gacagtccag cctatacagc tgccagaaaa agacagctgg actgtcaatg   2520
atatacaaaa attagtggga aaactaaata ccgcaagtca gatttatgca ggaattaaag   2580
taaagcaatt gtgtagactc ctcaggggag ccaaagcgct aacagatgta gtaacactga   2640
ctgaggaagc agaattagaa ttggcagaga acagggaaat tctaaaagaa cctgtacatg   2700
gagtatatta tgacccaaca aaagacttag tggcagaaat acagaaacaa gggcaagatc   2760
aatggacata tcaaatttat caagagccat ttaaaaatct aaagacagga aaatatgcaa   2820
aaaagaggtc ggcccacact aatgatgtaa aacaattaac agaggtagtg cagaaaatag   2880
ccatagaaag catagtaata tggggaaaga cccctaaatt tagactaccc atacaaagag   2940
aaacatggga agcatggtgg atggagtatt ggcaggctac ctggattcct gaatgggagt   3000
ttgtcaatac ccctcctcta gtaaaattat ggtaccagtt agagaaggac cccataatgg   3060
gagcagaaac tttctatgta gatggggcag ctaataggga gactaagcta ggaaaagcag   3120
ggtatgtcac tgacagagga agacaaaagg ttgtttccct aattgagaca acaaatcaaa   3180
agactcagtt acatgcaatt catctagcct tgcaggattc aggatcagaa gtaaatatag   3240
taacagactc acagtatgca ttaggaatca ttcaggcaca accagacagg agtgaatcag   3300
agttagtcaa tcaaataata gagaaactaa tagaaaagga caaagtctac ctgtcatggg   3360
taccagcaca caaagggatt ggaggaaatg aacaagtaga taaattagtc agtagtggaa   3420
tcagaaaggt actattttta gatggaatag ataaagccca agatgaacat tag          3473
```

<210> SEQ ID NO 3
<211> LENGTH: 2217

<212> TYPE: DNA
<213> ORGANISM: Artificial Sequence
<220> FEATURE:
<223> OTHER INFORMATION: MVA 62B ADA env

<400> SEQUENCE: 3
atgaaagtga aggggatcag gaagaattat cagcacttgt ggaaatgggg catcatgctc 60
cttgggatgt tgatgatctg tagtgctgta gaaaatttgt gggtcacagt ttattatggg 120
gtacctgtgt ggaaagaagc aaccaccact ctattttgtg catcagatgc taaagcatat 180
gatacagagg tacataatgt ttgggccaca catgcctgtg tacccacaga ccccaaccca 240
caagaagtag tattggaaaa tgtgacagaa aattttaaca tgtggaaaaa taacatggta 300
gaacagatgc atgaggatat aatcagttta tgggatcaaa gcctaaagcc atgtgtaaaa 360
ttaaccccac tctgtgttac tttaaattgc actgatttga ggaatgttac taatatcaat 420
aatagtagtg agggaatgag aggagaaata aaaaactgct ctttcaatat caccacaagc 480
ataagagata aggtgaagaa agactatgca cttttctata gacttgatgt agtaccaata 540
gataatgata atactagcta taggttgata aattgtaata cctcaaccat tacacaggcc 600
tgtccaaagg tatcctttga gccaattccc atacattatt gtaccccggc tggttttgcg 660
attctaaagt gtaaagacaa gaagttcaat ggaacagggc catgtaaaaa tgtcagcaca 720
gtacaatgta cacatggaat taggccagta gtgtcaactc aactgctgtt aaatggcagt 780
ctagcagaag aagaggtagt aattagatct agtaatttca cagacaatgc aaaaaacata 840
atagtacagt tgaaagaatc tgtagaaatt aattgtacaa gacccaacaa caatacaagg 900
aaaagtatac atataggacc aggaagagca ttttatacaa caggagaaat aataggagat 960
ataagacaag cacattgcaa cattagtaga acaaaatgga ataacacttt aaatcaaata 1020
gctacaaaat taaaagaaca atttgggaat aataaaacaa tagtctttaa tcaatcctca 1080
ggaggggacc cagaaattgt aatgcacagt tttaattgtg gaggggaatt cttctactgt 1140
aattcaacac aactgtttaa tagtacttgg aattttaatg gtacttggaa tttaacacaa 1200
tcgaatggta ctgaaggaaa tgacactatc acactcccat gtagaataaa acaaattata 1260
aatatgtggc aggaagtagg aaaagcaatg tatgcccctc ccatcagagg acaaattaga 1320
tgctcatcaa atattacagg gctaatatta acaagagatg gtggaactaa cagtagtggg 1380
tccgagatct tcagacctgg gggaggagat atgagggaca attggagaag tgaattatat 1440
aaatataaag tagtaaaaat tgaaccatta ggagtagcac ccaccaaggc aaaaagaaga 1500
gtggtgcaga gagaaaaaag agcagtggga acgataggag ctatgttcct tgggttcttg 1560
ggagcagcag gaagcactat gggcgcagcg tcaataacgc tgacggtaca ggccagacta 1620
ttattgtctg gtatagtgca acagcagaac aatttgctga gggctattga ggcgcaacag 1680
catctgttgc aactcacagt ctggggcatc aagcagctcc aggcaagagt cctggctgtg 1740
gaaagatacc taaggatcca acagctccta gggatttggg gttgctctgg aaaactcatc 1800
tgcaccactg ctgtgccttg gaatgctagt tggagtaata aaactctgga tatgatttgg 1860
gataacatga cctggatgga gtgggaaaga gaaatcgaaa attacacagg cttaatatac 1920
accttaattg aggaatcgca gaaccaacaa gaaaagaatg aacaagactt attagcatta 1980
gataagtggg caagtttgtg gaattggttt gacatatcaa attggctgtg gtatgtaaaa 2040
atcttcataa tgatagtagg aggcttgata ggtttaagaa tagtttttac tgtactttct 2100
atagtaaata gagttaggca gggatactca ccattgtcat ttcagaccca cctcccagcc 2160
ccgaggggac ccgacaggcc cgaaggaatc gaagaagaag gtggagacag agactaa 2217

<210> SEQ ID NO 4
<211> LENGTH: 3479
<212> TYPE: DNA
<213> ORGANISM: Artificial Sequence
<220> FEATURE:
<223> OTHER INFORMATION: MVA 62B GagPol

<400> SEQUENCE: 4
atgggtgcga gagcgtcagt attaagcggg ggagaattag atcgatggga aaaaattcgg 60
ttaaggccag ggggaaagaa aaaatataaa ttaaaacata tagtatgggc aagcagggag 120
ctagaacgat tcgcagttaa tcctggcctg ttagaaacat cagaaggctg tagacaaata 180
ctgggacagc tacaaccatc ccttcagaca ggatcagaag aacttagatc attatataat 240
acagtagcaa ccctctattg tgtgcatcaa aggatagaga taaaagacac caaggaagct 300
ttagacaaga tagaggaaga gcaaaacaaa agtaagaaaa aagcacagca agcagcagct 360
gacacaggac acagcaatca ggtcagccaa aattacccta tagtgcagaa catccagggg 420
caaatggtac atcaggccat atcacctaga actttaaatg catgggtaaa agtagtagaa 480
gagaaggctt tcagcccaga agtgataccc atgttttcag cattatcaga aggagccacc 540
ccacaagatt taaacaccat gctaaacaca gtgggggac atcaagcagc catgcaaatg 600
ttaaaagaga ccatcaatga ggaagctgca gaatgggata gagtgcatcc agtgcatgca 660
gggcctattg caccaggcca gatgagagaa ccaaggggaa gtgacatagc aggaactact 720
agtacccttc aggaacaaat aggatggatg acaaataatc cacctatccc agtaggagaa 780
atttataaaa gatggataat cctgggatta aataaaatag taagaatgta tagccctacc 840
agcattctgg acataagaca aggaccaaaa gaacccttta gagactatgt agaccggttc 900
tataaaactc taagagccga gcaagcttca caggaggtaa aaaattggat gacagaaacc 960
ttgttggtcc aaaatgcgaa cccagattgt aagactattt taaaagcatt gggaccagcg 1020
gctacactag aagaaatgat gacagcatgt cagggagtag gaggacccgg ccataaggca 1080
agagttttgg ctgaagcaat gagccaagta acaaattcag ctaccataat gatgcagaga 1140
ggcaatttta ggaaccaaag aaagattgtt aagtgtttca attgtggcaa agaagggcac 1200
acagccagaa attgcagggc ccctaggaaa aagggctgtt ggaaatgtgg aaaggaagga 1260
caccaaatga aagattgtac tgagagacag gctaattttt tagggaagat ctggccttcc 1320
tacaaggaaa ggccagggaa ttttcttcag agcagaccag agccaacagc cccaccagaa 1380
gagagcttca ggtctggggt agagacaaca actccccctc agaagcagga gccgatagac 1440
aaggaactgt atcctttaac ttccctcaga tcactctttg gcaacgaccc ctcgtcacaa 1500
taaagatagg ggggcaacta aaggaagctc tattagatac aggagcagat gatacagtat 1560
tagaagaaat gagtttgcca ggaagatgga aaccaaaaat gataggggga attggaggtt 1620
ttatcaaagt aagacagtat gatcagatac tcatagaaat ctgtggacat aaagctatag 1680
gtacagtatt agtaggacct acacctgtca acataattgg aagaaatctg ttgactcaga 1740
ttggttgcac tttaaatttt cccattagcc ctattgagac tgtaccagta aaattaaagc 1800
caggaatgga tggcccaaaa gttaaacaat ggccattgac agaagaaaaa ataaaagcat 1860
tagtagaaat ttgtacagaa atggaaaagg aagggaaaat ttcaaaaatt gggcctgaga 1920
atccatacaa tactccagta tttgccataa agaaaaaaga cagtactaaa tggaggaaat 1980
tagtagattt cagagaactt aataagagaa ctcaagactt ctgggaagtt caattaggaa 2040

```
taccacatcc cgcagggtta aaaaagaaaa aatcagtaac agtactggat gtgggtgatg   2100
catatttttc agttccctta gatgaagact tcaggaagta tactgcattt accataccta   2160
gtataaacaa tgagacacca gggattagat atcagtacaa tgtgcttcca cagggatgga   2220
aaggatcacc agcaatattc caaagtagca tgacaaaaat cttagagcct tttaaaaaac   2280
aaaatccaga catagttatc tatcaataca tgaacgattt gtatgtagga tctgacttag   2340
aaatagggca gcatagaaca aaaatagagg agctgagaca acatctgttg aggtggggac   2400
ttaccacacc agacaaaaaa catcagaaag aacctccatt cctttggatg ggttatgaac   2460
tccatcctga taaatggaca gtacagccta tagtgctgcc agaaaaagac agctggactg   2520
tcaatgacat acagaagtta gtggggaaat tgaataccgc aagtcagatt tacccaggga   2580
ttaaagtaag gcaattatgt aaactcctta gaggaaccaa agcactaaca gaagtaatac   2640
cactaacaga agaagcagag ctagaactgg cagaaaacag agagattcta aaagaaccag   2700
tacatggagt gtattatgac ccatcaaaag acttaatagc agaaatacag aagcaggggc   2760
aaggccaatg gacatatcaa atttatcaag agccatttaa aaatctgaaa acaggaaaat   2820
atgcaagaat gaggggtgcc cacactaatg atgtaaaaca attaacagag gcagtgcaaa   2880
aaataaccac agaaagcata gtaatatggg gaaagactcc taaatttaaa ctacccatac   2940
aaaaggaaac atgggaaaca tggtggacag agtattggca agccacctgg attcctgagt   3000
gggagtttgt taatacccct cctttagtga aattatggta ccagttagag aaagaaccca   3060
tagtaggagc agaaaccttc tatgtagatg gggcagctaa cagggagact aaattaggaa   3120
aagcaggata tgttactaac aaaggaagac aaaaggttgt ccccctaact aacacaacaa   3180
atcagaaaac tcagttacaa gcaatttatc tagctttgca ggattcagga ttagaagtaa   3240
acatagtaac agactcacaa tatgcattag gaatcattca agcacaacca gataaaagtg   3300
aatcagagtt agtcaatcaa ataatagagc agttaataaa aaaggaaaag gtctatctgg   3360
catgggtacc agcacacaaa ggaattggag gaaatgaaca agtagataaa ttagtcagtg   3420
ctggaatcag gaaaatacta tttttagatg gaatagataa ggcccaagat gaacattag    3479
```

<210> SEQ ID NO 5
<211> LENGTH: 2244
<212> TYPE: DNA
<213> ORGANISM: Artificial Sequence
<220> FEATURE:
<223> OTHER INFORMATION: MVA/HIV 71C Env

<400> SEQUENCE: 5

```
atgagagtga aggggatact gaggaattat cgacaatggt ggatatgggg catcttaggc     60
ttttggatgt taatgatttg taatggaaac ttgtgggtca cagtctatta tggggtacct    120
gtgtggaaag aagcaaaaac tactctattc tgtgcatcaa atgctaaagc atatgagaaa    180
gaagtacata atgtctgggc tacacatgcc tgtgtaccca cagaccccaa cccacaagaa    240
atggttttgg aaaacgtaac agaaaatttt aacatgtgga aaaatgacat ggtgaatcag    300
atgcatgagg atgtaatcag cttatgggat caaagcctaa agccatgtgt aaagttgacc    360
ccactctgtg tcactttaga atgtagaaag gttaatgcta cccataatgc taccaataat    420
ggggatgcta cccataatgt taccaataat gggcaagaaa tacaaaattg ctctttcaat    480
gcaaccacag aaataagaga taggaagcag agagtgtatg cacttttcta tagacttgat    540
atagtaccac ttgataagaa caactctagt aagaacaact ctagtgagta ttatagatta    600
```

ataaattgta atacctcagc cataacacaa gcatgtccaa aggtcagttt tgatccaatt 660
cctatacact attgtgctcc agctggttat gcgattctaa agtgtaacaa taagacattc 720
aatgggacag gaccatgcaa taatgtcagc acagtacaat gtacacatgg aattaagcca 780
gtggtatcaa ctcagctatt gttaaacggt agcctagcag aaggagagat aataattaga 840
tctgaaaatc tgacagacaa tgtcaaaaca ataatagtac atcttgatca atctgtagaa 900
attgtgtgta caagacccaa caataataca agaaaaagta taaggatagg gccaggacaa 960
acattctatg caacaggagg cataataggg aacatacgac aagcacattg taacattagt 1020
gaagacaaat ggaatgaaac tttacaaagg gtgggtaaaa aattagtaga acacttccct 1080
aataagacaa taaaatttgc accatcctca ggaggggacc tagaaattac aacacatagc 1140
tttaattgta gaggagaatt cttctattgc agcacatcaa gactgtttaa tagtacatac 1200
atgcctaatg atacaaaaag taagtcaaac aaaaccatca caatcccatg cagcataaaa 1260
caaattgtaa acatgtggca ggaggtagga cgagcaatgt atgcccctcc cattgaagga 1320
aacataacct gtagatcaaa tatcacagga atactattgg tacgtgatgg aggagtagat 1380
tcagaagatc cagaaaataa taagacagag acattccgac ctggaggagg agatatgagg 1440
aacaattgga gaagtgaatt atataaatat aaagcggcag aaattaagcc attgggagta 1500
gcacccactc cagcaaaaag gagagtggtg gagagagaaa aaagagcagt aggattagga 1560
gctgtgttcc ttggattctt gggagcagca ggaagcacta tgggcgcagc gtcaataacg 1620
ctgacggtac aggccagaca attgttgtct ggtatagtgc aacagcaaag caatttgctg 1680
agggctatcg aggcgcaaca gcatctgttg caactcacgg tctggggcat taagcagctc 1740
cagacaagag tcctggctat cgaaagatac ctaaaggatc aacagctcct agggctttgg 1800
ggctgctctg gaaaactcat ctgcaccact aatgtacctt ggaactccag ttggagtaac 1860
aaatctcaaa cagatatttg ggaaaacatg acctggatgc agtgggataa agaagttagt 1920
aattacacag acacaatata caggttgctt gaagactcgc aaacccagca ggaaagaaat 1980
gaaaaggatt tattagcatt ggacaattgg aaaaatctgt ggaattggtt tagtataaca 2040
aactggctgt ggtatataaa aatattcata atgatagtag gaggcttgat aggcttaaga 2100
ataatttttg ctgtgctttc tatagtgaat agagttaggc agggatactc acctttgtcg 2160
tttcagaccc ttaccccaaa cccaagggga cccgacaggc tcggaagaat cgaagaagaa 2220
ggtggagggc aagacagaga ctaa 2244

<210> SEQ ID NO 6
<211> LENGTH: 3419
<212> TYPE: DNA
<213> ORGANISM: Artificial Sequence
<220> FEATURE:
<223> OTHER INFORMATION: MVA/HIV 71C GagPol

<400> SEQUENCE: 6
atgggtgcga gagcgtcaat attaagaggg ggaaaattag ataaatggga aaagattagg 60
ttaaggccag ggggaaagaa acactatatg ctaaaacacc tagtatgggc aagcagggag 120
ctggaaagat ttgcacttaa ccctggcctt ttagagacat cagaaggctg taaacaaata 180
ataaaacagc tacaaccagc tcttcagaca ggaacagagg aacttaggtc attattcaat 240
gcagtagcaa ctctctattg tgtacatgca gacatagagg tacgagacac caaagaagca 300
ttagacaaga tagaggaaga acaaaacaaa agtcagcaaa aaacgcagca ggcaaaagag 360
gctgacaaaa aggtcgtcag tcaaaattat cctatagtgc agaatcttca agggcaaatg 420

-continued

```
gtacaccagg cactatcacc tagaactttg aatgcatggg taaaagtaat agaagaaaaa    480
gcctttagcc cggaggtaat acccatgttc acagcattat cagaaggagc caccccacaa    540
gatttaaaca ccatgttaaa taccgtgggg ggacatcaag cagccatgca aatgttaaaa    600
gataccatca atgaggaggc tgcagaatgg gatagattac atccagtaca tgcagggcct    660
gttgcaccag gccaaatgag agaaccaagg ggaagtgaca tagcaggaac tactagtaac    720
cttcaggaac aaatagcatg gatgacaagt aacccaccta ttccagtggg agatatctat    780
aaaagatgga taattctggg gttaaataaa atagtaagaa tgtatagccc tgtcagcatt    840
ttagacataa gacaagggcc aaaggaaccc tttagagatt atgtagaccg gttctttaaa    900
actttaagag ctgaacaagc ttcacaagat gtaaaaaatt ggatggcaga caccttgttg    960
gtccaaaatg cgaacccaga ttgtaagacc attttaagag cattaggacc aggagctaca   1020
ttagaagaaa tgatgacagc atgtcaagga gtgggaggac ctagccacaa agcaagagtg   1080
ttggctgagg caatgagcca aacaggcagt accataatga tgcagagaag caattttaaa   1140
ggctctaaaa gaactgttaa atgcttcaac tgtggcaagg aagggcacat agctagaaat   1200
tgcagggccc ctaggaaaaa aggctgttgg aaatgtggaa aggaaggaca ccaaatgaaa   1260
gactgtgctg agaggcaggc taattttta gggaaaattt ggccttccca caaggggagg   1320
ccagggaatt tccttcagaa caggccagag ccaacagccc caccagcaga gagcttcagg   1380
ttcgaggaga caacccctgc tccgaagcag gagctgaaag acagggaacc cttaacctcc   1440
ctcaaatcac tctttggcag cgaccccttg tctcaataaa aatagggggc cagataaagg   1500
aggctctctt agacacagga gcagatgata cagtattaga agaaatgaat ttgccaggaa   1560
aatggaaacc aaaaatgata ggaggaattg gaggttttat caaagtaaga cagtatgatc   1620
aaatacttat agaaatttgt ggaaaaaagg ctataggtac agtattagta ggacccacac   1680
ctgtcaacat aattggaaga aatatgctga ctcagattgg atgcacgcta aattttccaa   1740
ttagtcccat tgaaactgta ccagtaaaat taaagccagg aatggatggc ccaaaggtta   1800
aacaatggcc attgacagag gagaaaataa aagcattaac agcaatttgt gatgaaatgg   1860
agaaggaagg aaaaattaca aaaattgggc ctgaaaatcc atataacact ccaatattcg   1920
ccataaaaaa gaaggacagt actaagtgga gaaaattagt agatttcaga gaacttaata   1980
aaagaactca agacttctgg gaagttcaat taggaatacc acacccagca gggttaaaaa   2040
agaaaaaatc agtgacagta ctagatgtgg gggatgcata tttttcagtt cctttagatg   2100
aaagctttag gaggtatact gcattcacca tacctagtag aaacaatgaa acaccaggga   2160
ttagatatca atataatgtg cttccacaag gatggaaagg atcaccagca atattccaga   2220
gtagcatgac aaaaatctta gagcccttta gagcacaaaa tccagaaata gtcatctatc   2280
aatatatgaa tgacttgtat gtaggatctg acttagaaat agggcaacat agagcaaaga   2340
tagaggaatt aagagaacat ctattaaggt ggggatttac cacaccagac aagaaacatc   2400
agaaagaacc cccatttctt tggatggggt atgaactcca tcctgacaaa tggacagtac   2460
agcctataca gctgccagaa aaggagagct ggactgtcaa tgatatacag aagttagtgg   2520
gaaaattaaa cacggcaagc cagatttacc cagggattaa agtaagacaa ctttgtagac   2580
```

-continued tccttagagg ggccaaagca ctaacagaca tagtaccact aactgaagaa gcagaattag 2640
aattggcaga gaacagggaa attctaaaag aaccagtaca tggagtatat tatgaccctt 2700
caaaagactt gatagctgaa atacagaaac agggacatga ccaatggaca tatcaaattt 2760
accaagaacc attcaaaaat ctgaaaacag ggaagtatgc aaaaatgagg actgcccaca 2820
ctaatgatgt aaaacggtta acagaggcag tgcaaaaaat agccttagaa agcatagtaa 2880
tatggggaaa gattcctaaa cttaggttac ccatccaaaa agaaacatgg gagacatggt 2940
ggactgacta ttggcaagcc acctggattc ctgagtggga atttgttaat actcctcccc 3000
tagtaaaatt atggtaccag ctagagaagg aacccataat aggagtagaa actttctatg 3060
tagatggagc agctaatagg gaaaccaaaa taggaaaagc agggtatgtt actgacagag 3120
gaaggcagaa aattgtttct ctaactgaaa caacaaatca gaagactcaa ttacaagcaa 3180
tttatctagc tttgcaagat tcaggatcag aagtaaacat agtaacagac tcacagtatg 3240
cattaggaat tattcaagca caaccagata agagtgaatc agggttagtc aaccaaataa 3300
tagaacaatt aataaaaaag gaaagggtct acctgtcatg ggtaccagca cataaaggta 3360
ttggaggaaa tgaacaagta gacaaattag taagtagtgg aatcaggaga gtgctatag 3419

<210> SEQ ID NO 7
<211> LENGTH: 6
<212> TYPE: DNA
<213> ORGANISM: Artificial Sequence
<220> FEATURE:
<223> OTHER INFORMATION: end of promoter

<400> SEQUENCE: 7 taaata 6

<210> SEQ ID NO 8
<211> LENGTH: 52
<212> TYPE: DNA
<213> ORGANISM: Artificial Sequence
<220> FEATURE:
<223> OTHER INFORMATION: intervening sequence

<400> SEQUENCE: 8
agcccgggga tcctctagag tcgacctgca ggcatgctcg agcggccgca cc 52

<210> SEQ ID NO 9
<211> LENGTH: 11
<212> TYPE: DNA
<213> ORGANISM: Artificial Sequence
<220> FEATURE:
<223> OTHER INFORMATION: intervening sequence

<400> SEQUENCE: 9
agcccgggac c 11

<210> SEQ ID NO 10
<211> LENGTH: 9
<212> TYPE: DNA
<213> ORGANISM: Artificial Sequence
<220> FEATURE:
<223> OTHER INFORMATION: start of Env

<400> SEQUENCE: 10 atgagagtg 9

<210> SEQ ID NO 11
<211> LENGTH: 35

<212> TYPE: DNA
<213> ORGANISM: Artificial Sequence
<220> FEATURE:
<223> OTHER INFORMATION: intervening sequence

<400> SEQUENCE: 11
agcccgggga tcctctagag tcgagcggcc gcacc 35

<210> SEQ ID NO 12
<211> LENGTH: 70
<212> TYPE: DNA
<213> ORGANISM: Artificial Sequence
<220> FEATURE:
<223> OTHER INFORMATION: synthetic m2H5 promoter

<400> SEQUENCE: 12
aaaaaatgaa aaactattct aatttattag agagtattga tatattcata gaatttttcg 60
catataaata 70

<210> SEQ ID NO 13
<211> LENGTH: 4
<212> TYPE: PRT
<213> ORGANISM: Artificial Sequence
<220> FEATURE:
<223> OTHER INFORMATION: Endocytosis motif
<220> FEATURE:
<221> NAME/KEY: VARIANT
<222> LOCATION: 2, 3
<223> OTHER INFORMATION: Xaa = Any Amino Acid

<400> SEQUENCE: 13

Tyr Xaa Xaa Leu
1

<210> SEQ ID NO 14
<211> LENGTH: 36
<212> TYPE: DNA
<213> ORGANISM: Artificial Sequence
<220> FEATURE:
<223> OTHER INFORMATION: synthetic primer

<400> SEQUENCE: 14
cagcaggaat tcgttggtgg tcgccatgga tggtgt 36

<210> SEQ ID NO 15
<211> LENGTH: 30
<212> TYPE: DNA
<213> ORGANISM: Artificial Sequence
<220> FEATURE:
<223> OTHER INFORMATION: synthetic primer

<400> SEQUENCE: 15
ggggggggta cctaccagcc accgaaagag 30

<210> SEQ ID NO 16
<211> LENGTH: 60
<212> TYPE: DNA
<213> ORGANISM: Artificial Sequence
<220> FEATURE:
<223> OTHER INFORMATION: synthetic primer

<400> SEQUENCE: 16
ggggggctgc agtttggaaa gttttatagg ggggggctgc agtttggaaa gttttatagg 60

<210> SEQ ID NO 17
<211> LENGTH: 27

-continued

```
<212> TYPE: DNA
<213> ORGANISM: Artificial Sequence
<220> FEATURE:
<223> OTHER INFORMATION: synthetic primer

<400> SEQUENCE: 17

ggggggaagc ttaactagtt tctggtg                                    27
```